US011124841B2

(12) United States Patent
Oliver et al.

(10) Patent No.: US 11,124,841 B2
(45) Date of Patent: Sep. 21, 2021

(54) METHODS AND COMPOSITIONS FOR IDENTIFYING AND TREATING PATIENTS WITH SMALL CELL LUNG CANCER

(71) Applicant: UNIVERSITY OF UTAH RESEARCH FOUNDATION, Salt Lake City, UT (US)

(72) Inventors: Trudy Oliver, Salt Lake City, UT (US); Martin Sos, Salt Lake City, UT (US); Rob Wechsler-Reya, Salt Lake City, UT (US)

(73) Assignee: University Of Utah Research Foundation, Salt Lake City, UT (US)

( * ) Notice: Subject to any disclaimer, the term of this patent is extended or adjusted under 35 U.S.C. 154(b) by 98 days.

(21) Appl. No.: 16/335,368

(22) PCT Filed: Oct. 27, 2017

(86) PCT No.: PCT/US2017/058782
§ 371 (c)(1),
(2) Date: Mar. 21, 2019

(87) PCT Pub. No.: WO2018/081575
PCT Pub. Date: May 3, 2018

(65) Prior Publication Data
US 2020/0010901 A1 Jan. 9, 2020

Related U.S. Application Data

(60) Provisional application No. 62/444,968, filed on Jan. 11, 2017, provisional application No. 62/414,362, filed on Oct. 28, 2016.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

FOREIGN PATENT DOCUMENTS

| EP | 3531830 A1 | 9/2019 |
|---|---|---|
| WO | WO-2018/081575 A1 | 5/2018 |

OTHER PUBLICATIONS

Hamanaka et all. Human Pathology. 2014. 45: 1045-1056) (Year: 2014).*
Borromeo et al Cell Reports. Aug. 2016. Supplemental Information only, p. 1-10, vol. 16. (Year: 2016).*
Helfrich et al (J. Thoracic Oncology. Sep. 2015. 10(9) Supplement2, p. S363, Abstract MINI27.14 (Year: 2015).*
Melichar et al Lancet Oncology. Feb. 2015. 16: 395-405 (Year: 2015).*
Adi F. Gazdar et al. The Comparative Pathology of Genetically Engineered Mouse Models for Neuroendocrine Carcinomas of the Lung, Journal of Thoracic Oncology, vol. 10, No. 4, Apr. 1, 2015 (Apr. 1, 2015), pp. 553-564.
Arvanitis et al. Conditional transgenic models define how MYC initiates and maintains tumorigensis. Elsevier, Seminars in Cancer Biology, Saunders Scientific Publications, Phila vol. 16, No. 4, Aug. 1, 2006 (Aug. 1, 2006), pp. 313-317.
Bragelmann et al. Family matters: How MYC family oncogenes impact small cell lung cancer, Cell Cycle, vol. pub inv16, No. 16, Jul. 24, 2017 (Jul. 24, 2017), pp. 1489-1498.
Dong-Wook Kim et al. Genetic requirement for Mycl and efficacy of RNA Pol I inhibition in mouse models of small cell lung cancer, Genes & Development, Jun. 1, 2016 (Jun. 1, 2016), pp. 1289-1299.
Ekaterina A Semenova et al., Review Origins, genetic landscape, and emerging therapies of small cell lung cancer, gene & development 29 (14), Jul. 15, 2015 (Jul. 15, 2015), pp. 1447-1462, P055684960, DOI: 10.1101/gad.263145 Retrieved from the Internet: URL:https://www.ncbi.nlm.nih.gov/pmc/artic les/PMC4526731/pdf/1447.pdf [retrieved on Apr. 9, 2020].
Extended European Search Report was dated Jul. 27, 2020 by the European Patent Office Application No. 17865057.8 PCT/US2017/058782, filed on Oct. 27, 2017 and published as WO 2018/081575 on May 3, 2018 (Applicant—University of Utah Research Foundation) (19 Pages).
Francesco Paolo Fiorentino et al. Growth suppression by MYC inhibition in small cell lung cancer cells with TP53 and RB1 inactivation, Oncotarget, vol. 7, No. 21, May 24, 2016 (May 24, 2016).
Hollern et al. A mouse model with T58A mutations in Myc reduces the dependence on Kras mutations and has similarities to claudin-low human breast cancer, Oncogene, Mar. 7, 2013, vol. 32, No. 10, Apr. 23, 2012 (Apr. 23, 2012), pp. 1296-1304.
Ivo J Huijbers et al. Rapid target gene validation in complex cancer mouse models using re-derived embryonic stem cells, EMBO Molecular Medicine, vol. 6, No. 2, Jan. 8, 2014 (Jan. 8, 2014) , pp. 212-225.
Kee-Beom Kim, et al. Recent progress in mapping the emerging landscape of the small-cell lung cancer genome, Experimental and Molecular Medicine, vol. 51, No. 12, Dec. 1, 2019 (Dec. 1, 2019), pp. 1-13.
Kwon-Sik Park et al. Characterization of the cell of origin for small cell lung cancer, Cell Cycle, vol. 10, No. 16, Aug. 15, 2011 (Aug. 15, 2011), pp. 2806-2815.
Martin L Sos et al. A framework for identification of actionable cancer genome dependencies in small cell lung cancer, Proceedings of the National Academy of Sciences, US, vol. 109, No. 42, Oct. 16, 2012 (Oct. 16, 2012), pp. 17034-17039.
Milind D. Chalishazar et al. MYC-Driven Small-Cell Lung Cancer is Metabolically Distinct and Vulnerable to Arginine Depletion, Clinical Cancer Research, vol. 25, No. 16, Jun. 4, 2019 (Jun. 4, 2019), pp. 5107-5121.

(Continued)

*Primary Examiner* — Carla J Myers
(74) *Attorney, Agent, or Firm* — Ballard Spahr LLP

(57) ABSTRACT

Described herein are methods and compositions useful in detecting, diagnosing and treating small cell lung cancer. Transgenic animal models and cell lines are disclosed for the study of a small cell lung cancer subtype. Methods of screening and identifying active agents for the treatment of a small cell lung cancer subtype as well as methods of identifying patients susceptible to treatment with aurora kinase inhibitors are also provided.

7 Claims, 60 Drawing Sheets

Specification includes a Sequence Listing.

(56) References Cited

OTHER PUBLICATIONS

Mollaoglu Gurkan et al. MYC Drives Progression of Small Cell Lung Cancer to a Variant Neuroendocrine Subtype with Vulnerability to Aurora Kinase Inhibition, Cancer Cell, Cell Press, US, vol. 31, No. 2, Jan. 12, 2017 (Jan. 12, 2017), pp. 270-285.

Paul A. Bunn et al. Small Cell Lung Cancer: Can Recent Advances in Biology and Molecular Biology Be Translated into Improved Outcomes? Journal of Thoracic Oncology, vol. 11, No. 4, Apr. 1, 2016 (Apr. 1, 2016), pp. 453-474.

Stephen J McCormack et al. Myc/p53 interactions in transgenic mouse mammary development, tumorigenesis and chromosomal instability, Oncogene, vol. 16, No. 21, May 1, 1998 (May 1, 1998), pp. 2755-2766.

Takashi Kohno et al. Comparisons between Mouse and Human Studies Will Help the Prevention, Diagnosis, and Treatment of the Deadliest Type of Lung Cancer, Journal of Thoracic Oncology, vol. 10, No. 4, Apr. 1, 2015 (Apr. 1, 2015), pp. 551-552.

Borromeo et al. ASCL1 and NEUROD1 Reveal Heterogeneity in Pulmonary Neuroendocrine Tumors and Regulate Distinct Genetic Programs. Cell Reports, Aug. 2, 2016, vol. 16, No. 5, pp. 1259-1272.

Ehrhardt et al. Development of pulmonary bronchiolo-alveolar adenocarcinomas in transgenic mice overexpressing murine c-myc and epidermal growth factor in alveolar type II pneumocytes. British Journal of Cancer, 2001, vol. 84, No. 6, pp. 813-818.

Sutherland et al. Cell of Origin of Small Cell Lung Cancer: Inactivation of Trp53 and Rb1 in Distinct Cell Types of Adult Mouse Lung. Cancer Cell, Jun. 14, 2011, vol. 19, No. 6, pp. 754-764.

Wang et al. Phosphorylation regulates c-Myc's oncogenic activity in the mammary gland. Cancer Res. Feb. 1, 2011, vol. 71, No. 3, pp. 925-936.

International Search Report and Written Opinion were dated Mar. 13, 2018 by the International Searching Authority for International Application No. PCT/US2017/058782, filed on Oct. 27, 2017 and published as WO 2018/081575 on May 3, 2018 (Applicant—University of Utah Research Foundation) (14 Pages).

International Preliminary Report on Patentability was dated Apr. 30, 2019 by the International Searching Authority for International Application No. PCT/US2017/058782, filed on Oct. 27, 2017 and published as WO 2018/081575 on May 3, 2018 (Applicant—University of Utah Research Foundation) (9 Pages).

* cited by examiner

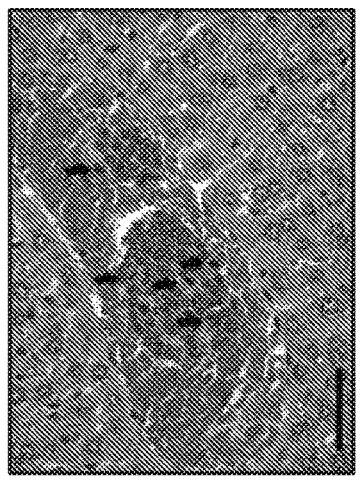
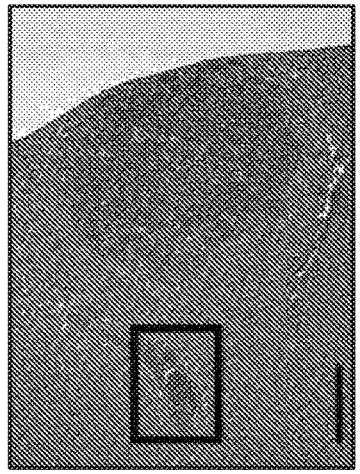
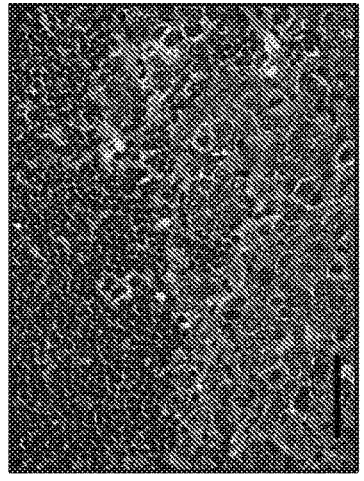
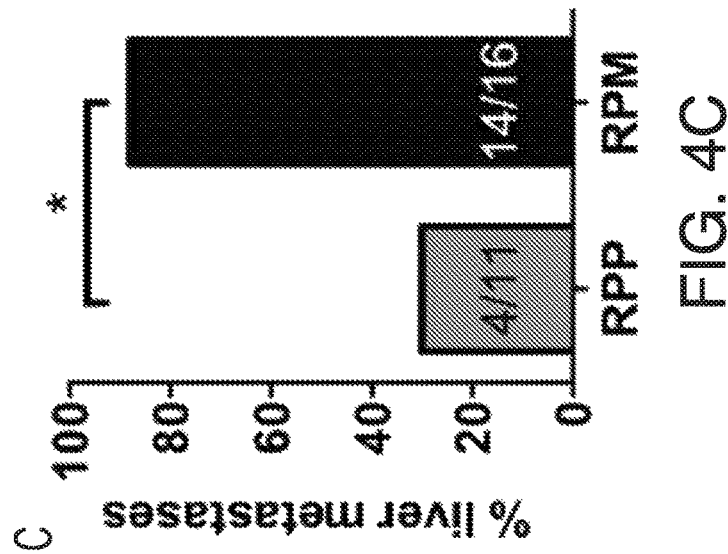
FIG. 4A
FIG. 4B
FIG. 4C

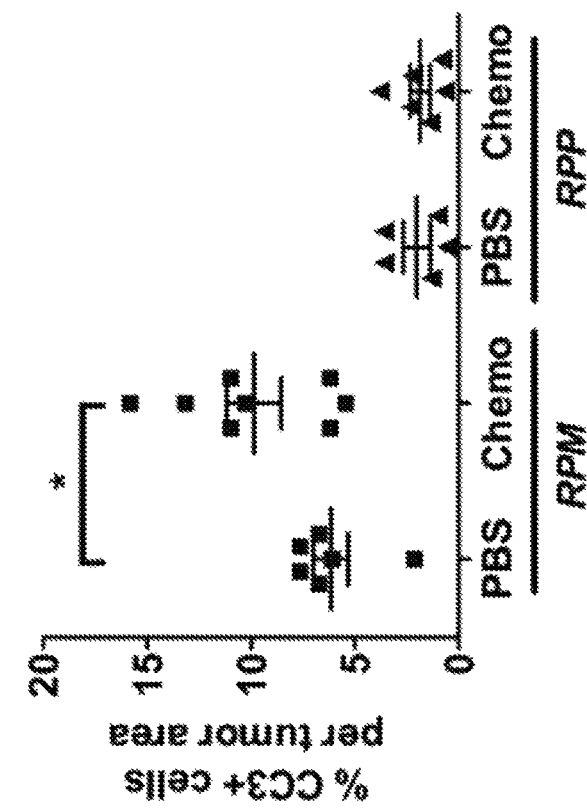
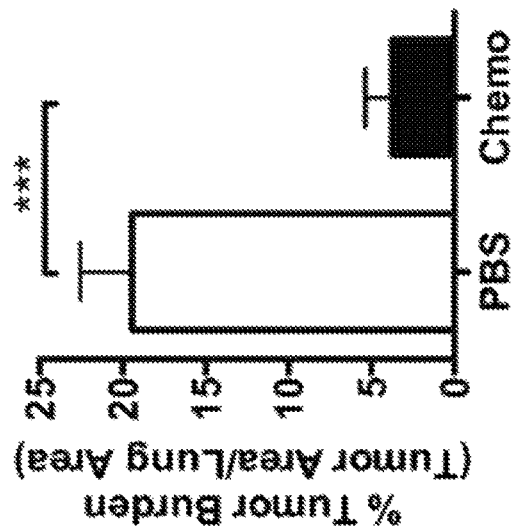
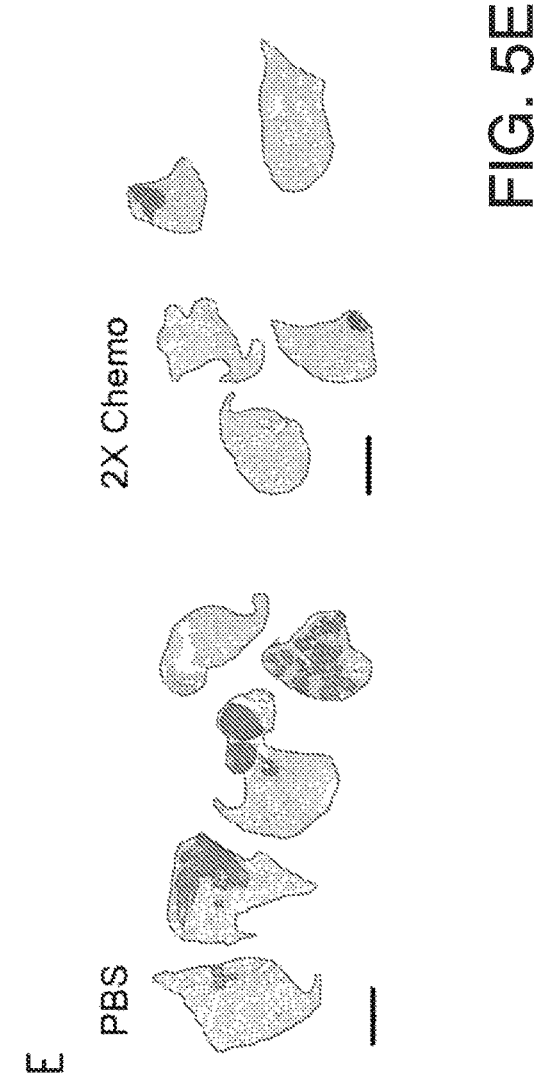
FIG. 5D
FIG. 5E

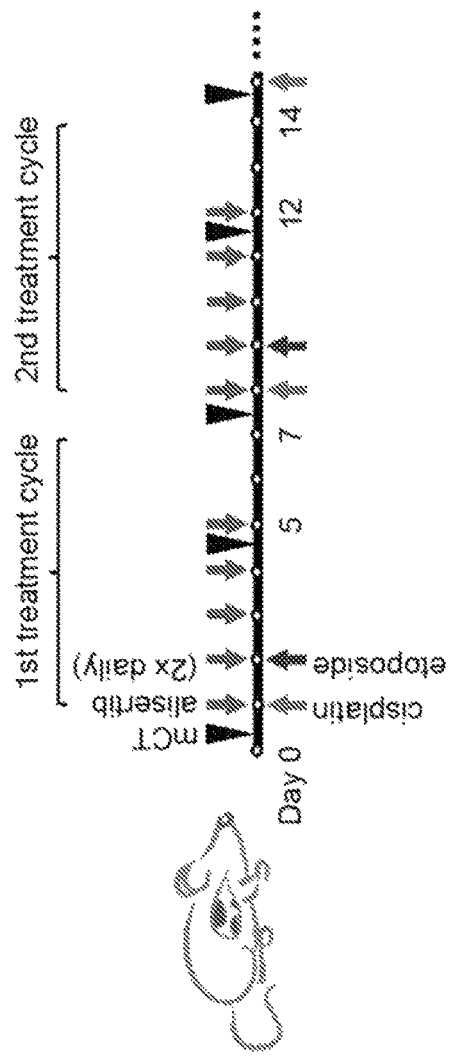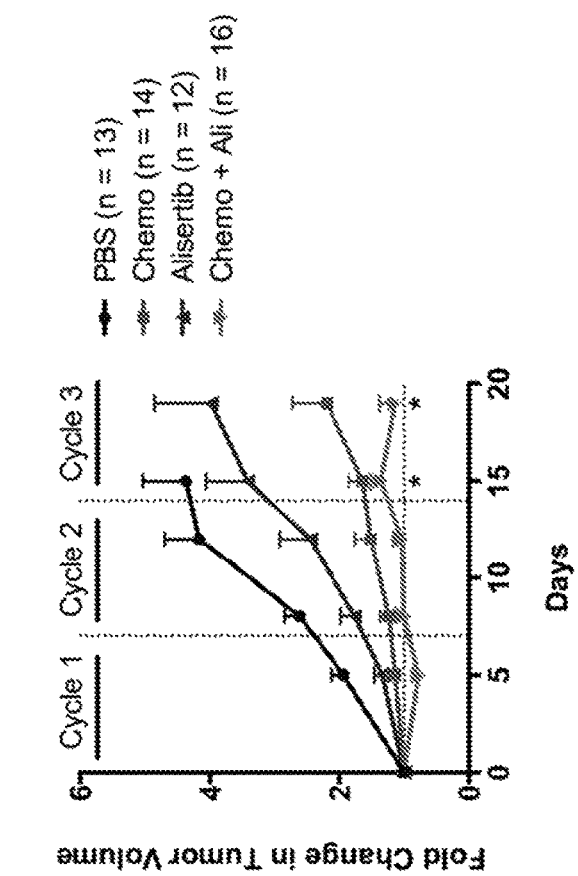
FIG. 7A
FIG. 7B

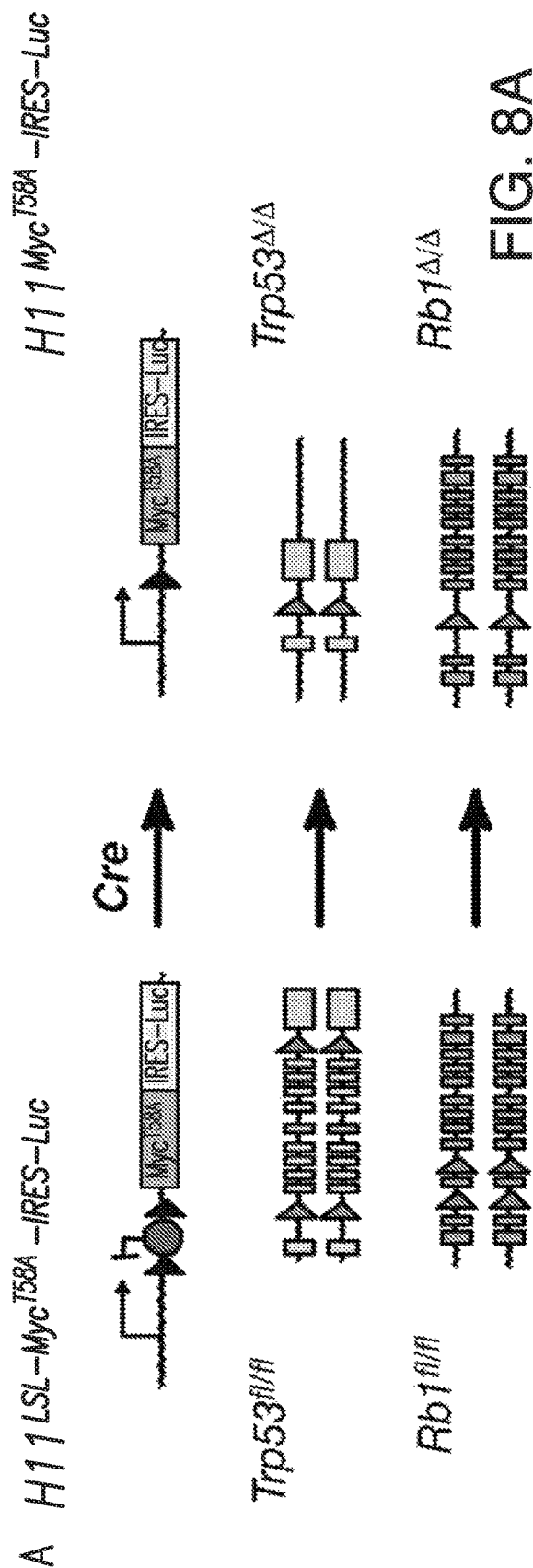
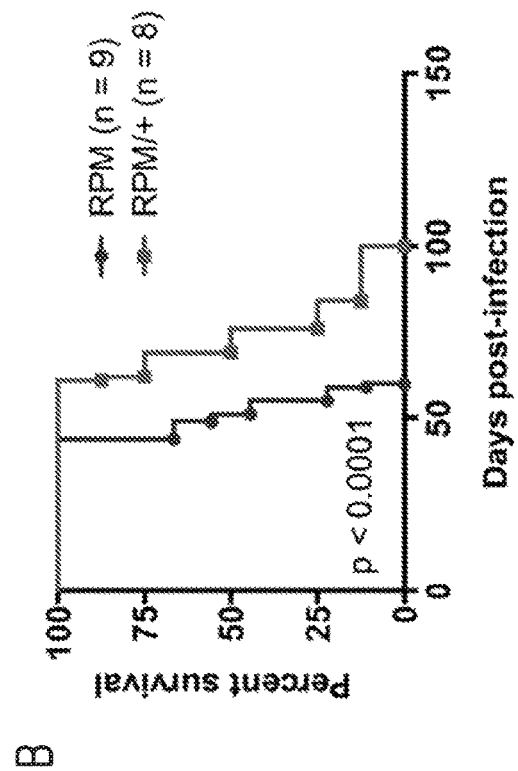
FIG. 8A
FIG. 8B

H

I

J

D

E

F

PB115

GLC1

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
aacttcccgc cgccgttgtt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
caacgggcca caactcctca                                              20

<210> SEQ ID NO 3
<211> LENGTH: 22
<212> TYPE: DNA
<213> ORGANISM: Artificial Sequence
<220> FEATURE:
<223> OTHER INFORMATION: Synthetic construct

<400> SEQUENCE: 3
tggaggagga caaactggtc ac                                           22

<210> SEQ ID NO 4
<211> LENGTH: 22
<212> TYPE: DNA
<213> ORGANISM: Artificial Sequence
<220> FEATURE:
<223> OTHER INFORMATION: Synthetic construct

<400> SEQUENCE: 4
ttccctttct gcttcatctt gc                                           22

<210> SEQ ID NO 5
<211> LENGTH: 19
<212> TYPE: DNA
<213> ORGANISM: Artificial Sequence
<220> FEATURE:
<223> OTHER INFORMATION: Synthetic construct

<400> SEQUENCE: 5
gaagcagcac gacttcttc                                               19

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
cctgagacag atcagcaaca a                                            21

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
cctaccctct caacgacagc                                          20

<210> SEQ ID NO 8
<211> LENGTH: 20
<212> TYPE: DNA
<213> ORGANISM: Artificial Sequence
<220> FEATURE:
<223> OTHER INFORMATION: Artificial Sequence

<400> SEQUENCE: 8
ctctgacctt ttgccaggag                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
cgacttcacc aactggttct                                          20

<210> SEQ ID NO 10
<211> LENGTH: 19
<212> TYPE: DNA
<213> ORGANISM: Artificial Sequence
<220> FEATURE:
<223> OTHER INFORMATION: Synthetic construct

<400> SEQUENCE: 10
ccgtgaatga ttggagtgc                                           19

<210> SEQ ID NO 11
<211> LENGTH: 19
<212> TYPE: DNA
<213> ORGANISM: Artificial Sequence
<220> FEATURE:
<223> OTHER INFORMATION: Synthetic construct

<400> SEQUENCE: 11
gctctgccaa gatggagag                                           19

<210> SEQ ID NO 12
<211> LENGTH: 19
<212> TYPE: DNA
<213> ORGANISM: Artificial Sequence
<220> FEATURE:
<223> OTHER INFORMATION: Synthetic construct

<400> SEQUENCE: 12
ctgtcgcttg acttgcttg                                           19

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
acctcgggac tcaacacctc                                          20

<210> SEQ ID NO 14
<211> LENGTH: 18
<212> TYPE: DNA
<213> ORGANISM: Artificial Sequence
<220> FEATURE:
<223> OTHER INFORMATION: Synthetic construct

<400> SEQUENCE: 14
ctgaggcccg taggaatc                                                 18

<210> SEQ ID NO 15
<211> LENGTH: 19
<212> TYPE: DNA
<213> ORGANISM: Artificial Sequence
<220> FEATURE:
<223> OTHER INFORMATION: Synthetic construct

<400> SEQUENCE: 15
ctccttctcc aatcagatg                                                19

<210> SEQ ID NO 16
<211> LENGTH: 19
<212> TYPE: DNA
<213> ORGANISM: Artificial Sequence
<220> FEATURE:
<223> OTHER INFORMATION: Synthetic construct

<400> SEQUENCE: 16
caagactggg cacctagtg                                                19

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
gtgtggttac aggcgaggat                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
gatgacatct cggcctttgt                                               20

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
gtcttcccct ccatcgtgg                                                19

<210> SEQ ID NO 20
<211> LENGTH: 20
<212> TYPE: DNA
<213> ORGANISM: Artificial Sequence
<220> FEATURE:
<223> OTHER INFORMATION: Synthetic construct

<400> SEQUENCE: 20
gatgcctctc ttgctctggg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
acggcactcc tagtctggaa                                              20

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
ccacgtcaat ctcttcacct t                                            21

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
cctagtgctg catgaggaga                                              20

<210> SEQ ID NO 24
<211> LENGTH: 23
<212> TYPE: DNA
<213> ORGANISM: Artificial Sequence
<220> FEATURE:
<223> OTHER INFORMATION: Synthetic construct

<400> SEQUENCE: 24
tcttcctcat cttcttgctc ttc                                          23

<210> SEQ ID NO 25
<211> LENGTH: 24
<212> TYPE: DNA
<213> ORGANISM: Artificial Sequence
<220> FEATURE:
<223> OTHER INFORMATION: Synthetic construct

<400> SEQUENCE: 25
ggcatagagg tctttacgga tgtc                                         24

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
tattggcaac gagcggttcc                                              20

<210> SEQ ID NO 27

<211> LENGTH: 439
<212> TYPE: PRT
<213> ORGANISM: Artificial Sequence
<220> FEATURE:
<223> OTHER INFORMATION: Synthetic construct

<400> SEQUENCE: 27

Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Asn Phe Tyr
            20                  25                  30

His Gln Gln Gln Ser Glu Leu Gln Pro Pro Ala Pro Ser Glu Asp
        35                  40                  45

Ile Trp Lys Lys Phe Glu Leu Leu Pro Ala Pro Pro Leu Ser Pro Ser
50                  55                  60

Arg Arg Ser Gly Leu Cys Ser Pro Ser Tyr Val Ala Val Ala Thr Ser
65                  70                  75                  80

Phe Ser Pro Arg Glu Asp Asp Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Thr Ser Ser Asp Ser Thr Ala Phe Ser Pro Ser Ser Asp Ser Leu
210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
            260                 265                 270

Pro Ala Lys Arg Ser Glu Ser Gly Ser Ser Pro Ser Arg Gly His Ser
        275                 280                 285

Lys Pro Pro His Ser Pro Leu Val Leu Lys Arg Cys His Val Ser Thr
290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335

Ser Asn Asn Arg Lys Cys Ser Ser Pro Arg Ser Ser Asp Thr Glu Glu
            340                 345                 350

Asn Asp Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
370                 375                 380

```
Glu Asn Asn Glu Lys Ala Pro Lys Val Val Ile Leu Lys Lys Ala Thr
385                 390                 395                 400

Ala Tyr Ile Leu Ser Ile Gln Ala Asp Glu His Lys Leu Thr Ser Glu
                405             410                 415

Lys Asp Leu Leu Arg Lys Arg Arg Glu Gln Leu Lys His Lys Leu Glu
            420             425                 430

Gln Leu Arg Asn Ser Gly Ala
        435
```

METHODS AND COMPOSITIONS FOR IDENTIFYING AND TREATING PATIENTS WITH SMALL CELL LUNG CANCER

CROSS REFERENCE TO RELATED APPLICATIONS

This application is the National Stage Entry under 35 U.S.C. § 371 of International PCT Application No. PCT/US2017/058782, filed Oct. 27, 2017, which claims the benefit of the filing dates of U.S. Provisional Application Nos. 62/414,362, filed Oct. 28, 2016, and 62/444,968, filed Jan. 11, 2017. The content of these earlier filed applications is hereby incorporated by reference in its entirety.

STATEMENT REGARDING FEDERALLY FUNDED RESEARCH

This invention was made with government support under grant number CA187457 awarded by the National Institutes of Health. The government has certain rights in the invention.

REFERENCE TO SEQUENCE LISTING

The Sequence Listing submitted herewith as a text file named "21101_0340U3_Sequence_Listing.txt," created on Jul. 10, 2019, and having a size of 9,234 bytes is hereby incorporated by reference pursuant to 37 C.F.R. § 1.52(e)(5).

BACKGROUND

Small cell lung cancer (SCLC) comprises about 14% of all lung cancers and leads to about 30,000 deaths each year in the United States. The average survival time for patients with SCLC is about 10 months, with a two-year survival rate of 6% (Kalemkerian et al., 2013; Pietanza et al., 2015). The standard systemic therapy for SCLC is platinum-based chemotherapy with etoposide, which has not changed for nearly 40 years. While 60-80% of patients respond to chemotherapy, tumors rapidly develop resistance and become cross-resistant to multiple therapies. SCLC is also highly metastatic with 50-80% of patients harboring metastases at the time of autopsy (Elliott et al., 1987). These dismal statistics highlight the need for a greater understanding of the disease and for new therapeutic approaches (Bunn et al., 2016).

Comprehensive genomic analyses of SCLC have reported loss of function alterations in RB1 and TP53 in 90-100% of SCLCs (George et al., 2015; Peifer et al., 2012; Rudin et al., 2012). Amplification of MYC family transcription factors including MYC, MYCL and MYCN, also occur in about 20% of tumors and are mutually exclusive (Peifer et al., 2012; Sos et al., 2012). Genomic amplifications in MYC have been identified in 6-25% of primary human tumors (Gazzeri et al., 1991; George et al., 2015) and in 30-50% of SCLC cell lines (Johnson et al., 1992; Sos et al., 2012). MYC amplification has been associated with poor outcome, tumor progression and treatment resistance, but how MYC impacts these processes has yet to be tested in vivo (Brennan et al., 1991; Johnson et al., 1987; Sos et al., 2012).

BRIEF DESCRIPTION OF THE DRAWINGS

FIG. 1A is survival curve showing mice infected with $10^8$ PFU of Cgrp-Cre. **p<0.0001. FIG. 1B is a representative bioluminescent image of uninfected (WT) or Cgrp-Cre infected RPM mice at 69 days post-infection with $10^6$ PFU virus. Units represent relative light units. FIG. 1C is a brightfield image of dissected lung from RPM mouse with tumor in the airway indicated by black arrow at 8 weeks post-infection. FIG. 1D is a 3D rendering of microCT data with lungs in gray, tumor in dark gray and major airways in black. FIG. 1E shows MicroCT images in indicated planes from WT or RPM mice at 39 and 44 days post Cgrp-Cre, respectively. A line surrounds the heart. FIG. 1F shows representative H&E staining at 3 weeks post-infection; scale bar is 1 mm. FIG. 1G shows H&E of perivascular and perilymphatic spread; scale bar is 250 µm. FIGS. 1H-I shows H&E of classic (H) and variant (I) SCLC morphology; scale bars are 50 µm. FIGS. 1J-M shows immunocytochemistry and quantification of pHH3 (J, K) or CC3 (L, M) in indicated tumor models. Scale bars are 50 µm. Error bars indicate mean+/−SEM.  p<0.0001; * p=0.001. See also FIGS. 8A-N.

FIG. 2A shows hierarchical cluster analysis of NE markers from mouse SCLC tumors by RNA-seq or expression array (indicated by #). FIG. 2B shows the expression of ASCL1 and NEUROD1 in mouse lung tumors grouped according to FIG. 2A. Proportions of MYC-high samples are indicated by pie charts (lower panel). FIG. 2C shows Gene Set Enrichment Analysis (GSEA) from RPM vs RPR2 tumors with normalized enrichment scores (NES) and p values for NEUROD1$^{high}$ and ASCL1$^{high}$ signatures. FIG. 2D shows immunohistochemistry and automated quantification of the percent positive cells per tumor area for indicated antibodies. Scale bars are 50 µm. Two-tailed unpaired t tests, ** p<0.0001; * p<0.001, * p<0.01; ns=not significant. FIG. 2E shows an immunoblot of mouse lung tumor lysates with NEUROD1 antibodies and source; HSP90 is loading control. Control human SCLC cell lines are − (H1963) and + (H82). See also FIGS. 9A-C.

FIG. 3A shows unsupervised hierarchical cluster analysis of NE markers from human SCLC patient samples and cell lines by RNA-seq. MYC expression (high or low), type of sample (cell line or tumor) and origin of data set (Rudin et al. or Cologne) indicated above the heatmap. FIG. 3B shows the expression of ASCL1 and NEUROD1 in human SCLCs and cell lines grouped by NE marker expression according to panel 3A. Proportions of MYC-high (white) vs. MYC-low (black) samples are indicated by pie charts (lower panel). FIG. 3C Gene Set Enrichment Analysis (GSEA) from MYC-high or MYC-low human SCLC with normalized enrichment scores (NES) and p values for NEUROD$^{high}$ and ASCL$^{high}$ signatures. FIG. 3D shows immunocytochemistry (IHC) serial sections from RPM lung tumor samples from early (in situ) and late (invasive) lesions stained with indicated antibodies, representative of expression patterns in panel 3E. Scale bars are 50 pm. FIG. 3E shows tumors grouped based on automated quantification of IHC staining as ASCL1 or NEUROD1 high or low. Proportions of tumors with each pattern (n=26 total in situ lesions; n=41 invasive lesions) are indicated. Two-tailed unpaired t tests, ** p<0.0001; * p<0.001; ns=not significant. See also FIGS. 10A-H.

FIGS. 4A-F show that Myc-driven tumors are metastatic similar to the human disease. FIG. 4A is representative H&E stain of metastatic liver lesions. Area in black box of middle panel is magnified in right panel. Black arrows indicate mitotic figures in blood vessel. Scale bars in panels from left to right are: 500, 200 and 50 µm. FIG. 4B shows the H&E of mediastinal lymph node metastases. Scale bar (right panel) is 50 µm. FIG. 4C shows the quantification of liver metastases in indicated mice using contingency table with Fisher's exact test, two-tailed, p=0.0115. Number of mice with liver metastases out of total number of mice indicated within bars. FIG. 4D is a representative immunocytochemistry (IHC) for indicated antibodies in indicated metastatic tissues. Scale bar is 50 µm. FIG. 4E is a representative IHC for NFIB in primary lung tissue from indicated mice. Scale bar is 50 µm. FIG. 4F shows ChIP-seq analysis of MYC genomic targets in three independent RPM cell lines.

FIGS. 5A-G show that Myc-driven small cell lung cancer (SCLC) is responsive to chemotherapy, but relapses. FIG. 5A shows H&E stained lung tumor tissue in the absence (PBS) or presence of a single dose of Chemo (7 mg/kg cisplatin+10 mg/kg etoposide) and representative immunocytochemistry (IHC) for indicated antibodies. Scale bar is 50 µm. FIGS. 5B-D show automated quantification of IHC for percent positive cells per tumor area for pH2AX (B), BrdU (C) or CC3 (D) from indicated mice as in A. Dots are average per animal. * $p<0.0003$,  $p<0.003$, * $p<0.05$. FIG. 5E shows H&E of whole sections from RPM mice treated with PBS or 2 doses of chemotherapy (2× Chemo). Lung outlined in black, tumor shown in dark grey. Scale bar is 4 mm. Automated quantification of percent tumor burden; n=7 mice per treatment group. * $p<0.0007$. FIG. 5F is a representative microCT image and quantification of total tumor burden from animals in panel E at indicated times. Tumors are pseudo-colored grey for visualization; air space is black. Error bars indicate mean+/−SEM. * $p<0.0008$; ** $p<0.0001$. FIG. 5G shows the results of Kaplan-Meier survival analysis of RPM mice treated with 5 mg/kg cisplatin and 10 mg/kg etoposide indicated by dashed vertical lines. ** $p<0.0001$. See also FIGS. 11A-I.

FIG. 6A shows a heatmap of median $GI_{50}$ values for indicated human SCLC cell lines treated with indicated drugs for 72-96 hrs. FIG. 6B shows the statistical significance of increased drug responses in panel 6A tested for each compound (one-sided t-tests, p-values adjusted according to Bonferroni-Holm). FIGS. 6C-F show the $GI_{50}$-values of cells treated with cisplatin (C), etoposide (D), alisertib (E) or barasertib (F) in triplicate for 96 hrs. Mean+/−SEM of n=4-7 experiments. FIG. 6G shows the mean $GI_{50}$ drug responses of SCLC cell lines grouped according to MYC status. Statistical significance calculated by two-sided t-tests with Bonferoni-Holm correction for multiple testing. FIG. 6H shows immunoblot of whole cell lysates from cell lines treated for 48 hr with indicated concentrations of alisertib. HSP90 serves as loading control.

FIGS. 7A-G show that aurora kinase inhibition combined with chemotherapy significantly prolongs survival of mice with Myc-driven SCLC. FIG. 7A is a schematic for in vivo drug studies in RPM mice. Black arrowheads indicate microCT imaging. Gray downward arrows indicate alisertib (Ali) treatment (20 mg/kg, twice daily); gray upward arrows indicate cisplatin (5 mg/kg) or etoposide (10 mg/kg). Days indicated as white dots on X-axis. FIG. 7B shows the fold change in tumor burden in indicated cohorts of RPM mice. Error bars represent SEM for Chemo vs. Chemo+Ali, * $p<0.05$ at indicated time points. FIG. 7C shows representative microCT images from RPM mice pseudo-colored with tumors (gray) and normal tissue/airway (black). FIG. 7D is a waterfall plot of percent total tumor volume change from Day 0-19 (or last scan before death) of individual RPM mice treated as in A for three cycles. Partial response and stable disease indicated with gray shading. Two-tailed unpaired t tests, p<*0.023, <0.002, **<0.0001. FIG. 7E shows the immunocytochemistry for indicated antibodies in each treatment group analyzed at the time of death as in panel G. Scale bar is 50 µm. FIG. 7F shows the quantification of average positive cells per tumor area for individual tumors, * p<0.02, *<0.0008, <0.0001. ns=not significant. FIG. 7G shows the Kaplan-Meier survival analysis from RPM mice treated as in A with Day 0 as start of treatment. Dashed lines indicate cisplatin treatment as in A. Log-rank (Mantel-Cox) test, p<0.009, *<0.0006, **<0.0001, ns=not significant. See also FIG. 12.

FIGS. 8A-N show the generation and validation of Myc-driven $Rb1^{fl/fl}$ $Trp53^{fl/fl}$ mouse model of small cell lung cancer (SCLC). FIG. 8A shows a cartoon diagram of LSL-MycT58A-IRES-Luciferase allele in the H11 locus, combined with Trp53 and Rb1 conditional alleles before and after Cre expression. Cartoon triangles represent LoxP sites. Rectangles indicate exons. FIG. 8B shows a survival curve following Cgrp-Cre infection in homozygous RPM or MYC-heterozygous (RPM/+) mice. FIGS. 8K-N shows representative IHC (K) and manual quantification for SPC (L), CCSP (M) or NKX2-1 (N) in lung tumor tissue from indicated mice. Scale bars in Panel K are 50 µm. Dashed line in dot plots indicate negative staining. Error bars represent mean+/−SEM. **** p<0.0001, ns=not significant.

FIG. 9A shows the copy number variation by DNA sequencing from indicated RPM tumors and cell lines. Chromosome 4 is depicted with Mycl and Nfib location indicated by black arrows and yellow lines. 3151T1 (RP) cell line serves as positive (+) control. Scale bar indicates copy number. FIG. 9B shows quantitative real-time RT-PCR of Myc and Mycl expression from freshly harvested tumors of indicated genotypes. Each dot represents one tumor. ** p<0.0001; * p<0.001. FIG. 9C shows representative immunocytochemistry and quantification of ASCL1 and NEUROD1 in serial lung tumor sections from indicated mice. Scale bar is 50 µm. Number of tumors analyzed indicated in bars. ns=not significant.

FIG. 10A depicts an unsupervised hierarchical clustering based on neuroendocrine (NE) marker expression of published gene expression data for 65 human SCLC cell lines (Polley et al, 2016) demonstrating three subgroups. Annotation (top) indicates cell lines specific to Polley et al. (black) and those also present in our cell line panel (gray). Annotated classification of cell lines as high/low MYC (black/white) was performed as described in Suppl. Methods. FIG. 10 B shows the expression of ASCL1 and NEUROD1 in Polley et al. cell lines divided according to subgroups (A-C) derived from cluster analysis in FIG. 10A. Fraction of MYC high/low cell lines per group indicated as pie charts (lower panel). Significance was calculated with two-tailed t-tests. ns=not significant,  p<0.01,  p<0.0001. FIG. 10C is a representative immunocytochemistry (IHC) of CGRP and NCAM1 from RPM mice. Scale bar is 50 µm. FIG. 10D shows representative IHC and quantification of UCHL1 in lung tumor tissue from indicated mice. Scale bar is 50  p<0.002, **** p<0.0001. FIG. 10 E shows overexpression of MYC or MYCT58A in 3151T1 (RP) cells reduces SYP protein levels. HSP90 serves as loading control. FIG. 10F shows MYC, ASCL1, SYP and NCAM1 expression assessed in human SCLC cell lines GLC1, GLC2, H82 after control (shGFP) or MYC knockdown by qRT-PCR performed in two independent experiments per cell line. Bars represent average $2^{-ddCt}$ values with SEM across cell lines. p-values are calculated with two-tailed t-test. ns=not significant, * p<0.05. FIG. 10G shows SYP protein levels increase upon MYC knockdown in GLC1 and GLC2 cells. Representative immunoblot of whole cell lysates of control (shGFP) or MYC knockdown (shMYC) cells with indicated antibodies. HSP90 serves as a loading control. Graph depicts the average with standard deviation (SD) of SYP protein levels in GLC1 and GLC2 upon MYC knockdown in three independent experiments. SYP signal was normalized to HSP90 and the control (shGFP). FIG. 10H shows ChIP-Seq analysis of MYC genomic targets in three independent RPM cell lines. Ptma serves as positive control. Binding of Myc was not detected near the NeuroD1 gene.

FIG. 11A shows the IC50 of MYC-high vs. MYC-low human SCLC cell lines (n=65 lines) treated with indicated drugs obtained from Polley et al, JNCI, 2016. Wilcoxon (Mann-Whitney) p-values indicated in figure. FIG. 11B is a brightfield image of PB115 cells demonstrating loosely aggregated clusters (derived from RPM mice infected with Cgrp-Cre) in culture; scale bar is 50 µm. FIG. 11C shows the immunoblot analysis for indicated antibodies with indicated cell lines. Black arrow indicates correct band for RB1. ACTIN serves as loading control. PB115 and PB120 are homozygous RPM. PB124 and PB119 are RPMLSL/+. AD=adenocarcinoma. See FIG. 6 for full genotypes. FIG. 11D shows the analysis of doubling time relative to alisertib sensitivity (measured by GI50) by Pearson correlation coefficient. FIG. 11E showed GLC2 cells treated with increasing amounts of alisertib. Whole cell lysates analyzed by immunoblot for indicated antibodies. HSP90 serves as a loading control. FIG. 11F shows an immunoblot as in (E) of GLC2 cells treated with 1 µM alisertib or barasertib for the indicated time points. FIG. 11G AURKA and AURKB knockdown in GLC2 cells. Graph depicts relative cell viability normalized to control (shGFP) as average of three independent experiments with mean+/-SD. Representative immunoblot of AURKA and AURKB after knockdown. HSP90 serves as a loading control. FIG. 11H shows DNA content measured by PI staining of indicated mouse cell lines treated with the indicated concentrations of alisertib (48 hr) or DMSO control as measured by flow cytometry. Representative of two independent experiments. See FIG. 6 for full genotypes. FIG. 11I is an immunoblot of MYC levels following addition of cycloheximide (CHX) at indicated time points after treatment with 1 µM alisertib or DMSO for 24 hr in PB115 (mouse RPM) or GLC1(human, MYC-high) cells. HSP90 serves as loading control. Graph depicts average with SEM of MYC protein relative to HSP90 normalized to 0 min time-point in three independent experiments. Significance was calculated for each time point by two-tailed paired t-tests. ns=not significant. * denotes an unspecific cross-reactive band.

FIG. 12A shows the weight of mice over course of 20 days of treatment with PBS vehicle control (n=5), alisertib (20 mg/kg twice daily, 5 days on, 2 days off, n=5), chemotherapy (5 mg/kg cisplatin+10 mg/kg etoposide, once weekly, n=7), or the combination of alisertib+chemotherapy (n=7). FIG. 12B shows the fold change in total tumor volume growth for individual RPM animals treated as in FIG. 7A with average fold change for each treatment group presented in FIG. 7B. Last volume for each mouse indicates last image captured before sacrifice. FIG. 12C shows representative H&E images of tumors from alisertib-treated RPM mice following two weeks of treatment at 20 mg/kg twice daily. Black arrows indicate aberrant mitoses involving lagging or detached chromosomes. Circles highlight cells with abnormal quantities of DNA compared to neighboring cells. Scale bar is 50 µm. Quantification of abnormal mitoses from lung tumor tissue from RPM mice (n=4) per treatment group with n=4 random 40× fields analyzed per animal. Error bars represent SEM. **** p<0.0001. Representative serial sections taken from lung tumor tissue of alisertib-treated animals stained with antibodies to ASCL1 or NEUROD1 illustrates that large abnormal cells are NEUROD1+. FIG. 11D shows a bar graph of indicated human cell lines GLC2 (MYC), GLC1 (MYC), and GLC8 (MYCN) treated with DMSO or 10 nM alisertib in combination with 0.1 µM etoposide or cisplatin for 96 hr. Averages with SD of the three independent experiments performed in duplicate. Significance analyzed by student's t-test, ns=not significant, * p<0.05, ** p<0.01.

SUMMARY

Figure 1A:
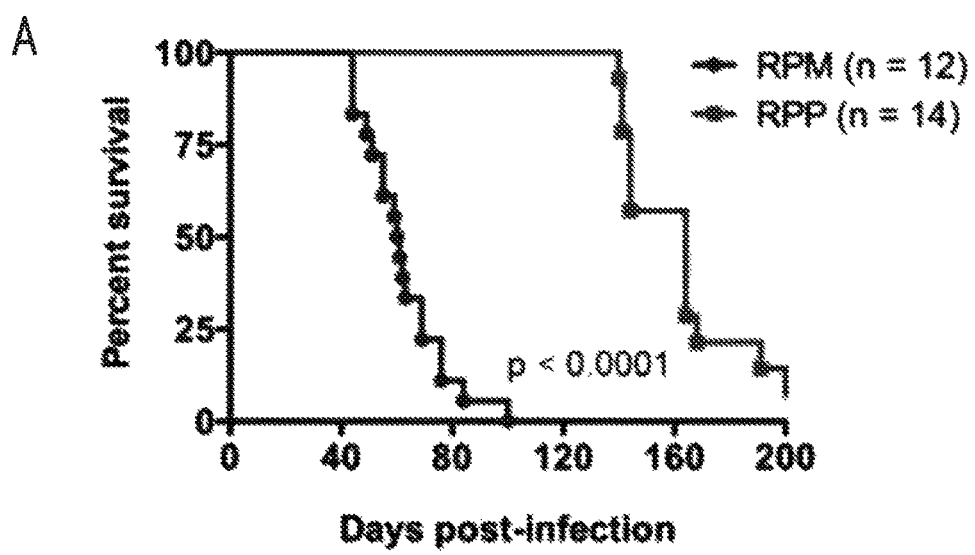
FIGS. 1A-M show that Myc promotes rapid small cell lung cancer (SCLC) in cooperation with Rb1 and Trp53 loss.

Disclosed herein is transgenic mouse comprising: a. genome wherein both alleles of endogenous Rb1 and Trp53 genes are ablated; and b. a transgene expressing an exogenous Myc gene operably linked to a regulatory sequence which directs expression of the exogenous Myc gene in lung cells, wherein the exogenous Myc gene is expressed in said transgenic mouse.

Disclosed herein are methods of screening for a biologically active agent effective for the treatment of small cell lung cancer, the method comprising administering a candidate agent to a transgenic mouse comprising: a. a genome wherein both alleles of endogenous Rb1 and Trp53 genes are ablated; and b. a transgene expressing an exogenous Myc gene operably linked to a regulatory sequence which directs expression of the exogenous gene in lung cells, wherein agents that increase survival or reduce tumor size are identified as effective for the treatment of small cell lung cancer.

Disclosed herein are methods of screening for a biologically active agent for the treatment of small cell lung cancer, the methods comprising: a. determining the expression of aurora kinase in a transgenic mouse cell line comprising: i. a genome wherein both alleles of endogenous Rb1 and Trp53 genes are ablated; and ii. a transgene expressing an exogenous Myc gene operably linked to a regulatory sequence which directs expression of the exogenous gene in lung cells, b. contacting a biologically active agent with the transgenic mouse cell line; and c. determining the expression of aurora kinase in the transgenic mouse cell line after step (b), correlating the level of aurora kinase in the transgenic mouse cell line of step (a) with the level of aurora kinase in the transgenic mouse cell line of step (c), wherein a decrease in the level of aurora kinase in step (c) compared to step (a) indicates that the biologically active agent is likely to be effective for the treatment of small cell lung cancer.

Disclosed herein are methods of detecting a variant subtype of small cell lung cancer in a subject, the method comprising: a. obtaining a sample from a human subject; b. determining the level of (i) NEUROD1, (ii) Myc or Mycl, and (iii) ASCL1 in the subject's sample; and c. comparing the levels of (i) NEUROD1, (ii) Myc or Mycl and (iii) ASCL1 of the subject's sample to a sample from a human subject that does not have small cell lung cancer, wherein an increased level of NEUROD1, an increased level of Myc or a decreased level of Mycl and a decreased level of ASCL1 in the subject's sample indicates that the subject has a variant subtype of small cell lung cancer.

Disclosed herein are methods of treating a patient with a variant small cell lung cancer, the method comprising: a. identifying a patient in need of treatment; and b. administering to the patient a therapeutically effective amount of an aurora kinase inhibitor.

Disclosed herein are methods of predicting a small cell lung cancer patient's responsiveness to an aurora kinase inhibitor therapy, the method comprising: a. obtaining a sample from the patient; b. determining the level of (i) NEUROD1, (ii) Myc or Mycl, and (iii) ASCL1 in the patient's sample, or any panel of neuroendocrine genes or EPCAM; and c. comparing the levels of (i) NEUROD1, (ii) Myc or Mycl and (iii) ASCL1 of the patient's sample to a sample from a human subject that does not have small cell lung cancer, or any panel of neuroendocrine genes or EPCAM, wherein an increased level of NEUROD1, an increased level of Myc and a decreased level of ASCL1 or EPCAM or other neuronendocrine genes in the patient's sample indicates that the subject is likely to respond to an aurora kinase inhibitor therapy.

Disclosed herein are methods of predicting a small cell lung cancer patient's responsiveness to a BCL-2 inhibitor therapy, the method comprising: a. obtaining a sample from the patient; b. determining the level of (i) NEUROD1, (ii) Myc or Mycl, and (iii) ASCL1 in the patient's sample, or any panel of neuroendocrine genes or EPCAM; and c. comparing the levels of (i) NEUROD1, (ii) Myc or Mycl and (iii) ASCL1 of the patient's sample to a sample from a human subject that does not have small cell lung cancer, or any panel of neuroendocrine genes or EPCAM, wherein a decreased level of NEUROD1 or Myc, an increased level of Mycl, or an increased level of ASCL1 or EPCAM or other neuroendocrine genes in the patient's sample indicates that the subject is likely to respond to a BCL-2 inhibitor therapy.

Disclosed herein are methods of predicting the success of an aurora kinase inhibitor therapy in a patient with small cell lung cancer, the method comprising: a. obtaining a sample from the patient; b. determining the level of (i) NEUROD1, (ii) Myc or Mycl, and (iii) ASCL1 in the patient's sample, or any panel of neuroendocrine genes or EPCAM; and c. comparing the levels of (i) NEUROD1, (ii) Myc or Mycl and (iii) ASCL1 of the patient's sample to a sample from a human subject that does not have small cell lung cancer, or any panel of neuroendocrine genes or EPCAM, wherein an increased level of NEUROD1, an increased level of Myc and a decreased level of Lmyc, ASCL1, EPCAM or other neuroendocrine genes in the patient's sample indicates that the aurora kinase inhibitor therapy will be successful in the patient.

Disclosed herein are methods of predicting the success of a BCL-2 inhibitor therapy in a patient with small cell lung cancer, the method comprising: a. obtaining a sample from the patient; b. determining the level of (i) NEUROD1, (ii) Myc or Mycl, and (iii) ASCL1 in the patient's sample, or any panel of neuroendocrine genes or EPCAM; and c. comparing the levels of (i) NEUROD1, (ii) Myc or Mycl and (iii) ASCL1 of the patient's sample to a sample from a human subject that does not have small cell lung cancer, or any panel of neuroendocrine genes or EPCAM, wherein a decreased level of NEUROD1 or MYC, an increased level of MYCL or ASCL1 or EPCAM or other neuroendocrine genes in the patient's sample indicates that the BCL-2 inhibitor therapy will be successful in the patient.

DETAILED DESCRIPTION

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components. The term sample can also refer to a "cancer sample" or "sample of the cancer" or the like. The sample can be obtained via biopsy such as needle biopsy, surgical biopsy, etc. A cancer sample includes, for example, a specimen of cancers, parts of a cancer, cancer cells derived from a cancer (including cancer cell lines derived from a cancer and are grown in cell culture) and also the cancer mass as a whole, cell lines, cells and/or tissue derived from a subject that are suspected of being cancerous or suspected of comprising cancerous cells. Thus, it is possible that the cancer sample may also comprise non-cancerous cells.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step. The term "cancer patient" can refer to a subject having a cancer described herein, including a subject diagnosed to suffer from a cancer, but also includes a subject, for example, during or after therapy.

As used herein, the term "comprising" can include the aspects "consisting of" and "consisting essentially of." "Comprising can also mean "including but not limited to."

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

The terms "alter" or "modulate" can be used interchangeable herein referring, for example, to the expression of a nucleotide sequence in a cell means that the level of expression of the nucleotide sequence in a cell after applying a method as described herein is different from its expression in the cell before applying the method.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100%, or more, or any amount of promotion in between compared to native or control levels. In an aspect, the increase or promotion is 10-20, 20-30, 30-40, 40-50, 50-60, 60-70, 70-80, 80-90, or 90-100% as compared to native or control levels. In an aspect, the increase or promotion is 0-25, 25-50, 50-75, or 75-100%, or more, such as 200, 300, 500, or 1000% more as compared to native or control levels. In an aspect, the increase or promotion can be greater than 100 percent as compared to native or control levels, such as 100, 150, 200, 250, 300, 350, 400, 450, 500% or more as compared to the native or control levels.

As used herein, the term "determining" can refer to measuring or ascertaining a quantity or an amount or a change in activity. For example, determining the amount of a disclosed polypeptide in a sample as used herein can refer to the steps that the skilled person would take to measure or ascertain some quantifiable value of the polypeptide in the sample. The art is familiar with the ways to measure an amount of the disclosed polypeptides and disclosed nucleotides in a sample.

As used herein, the terms "disease" or "disorder" or "condition" are used interchangeably referring to any alternation in state of the body or of some of the organs, interrupting or disturbing the performance of the functions and/or causing symptoms such as discomfort, dysfunction, distress, or even death to the person afflicted or those in contact with a person. A disease or disorder or condition can also related to a distemper, ailing, ailment, malady, disorder, sickness, illness, complaint, affection.

As used herein, the term "normal" refers to an individual, a sample or a subject that does not have cancer or does not have small cell lung cancer.

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "expression vector" is herein to refer to vectors that are capable of directing the expression of genes to which they are operatively-linked. Common expression vectors of utility in recombinant DNA techniques are often in the form of plasmids. Recombinant expression vectors can comprise a nucleic acid as disclosed herein in a form suitable for expression of the acid in a host cell. In other words, the recombinant expression vectors can include one or more regulatory elements or promoters, which can be selected based on the host cells used for expression that is operatively linked to the nucleic acid sequence to be expressed.

The term "sequence of interest" or "gene of interest" can mean a nucleic acid sequence (e.g., a therapeutic gene), that is partly or entirely heterologous, i.e., foreign, to a cell into which it is introduced.

The term "sequence of interest" or "gene of interest" can also mean a nucleic acid sequence, that is partly or entirely homologous to an endogenous gene of the cell into which it is introduced, but which is designed to be inserted into the genome of the cell in such a way as to alter the genome (e.g., it is inserted at a location which differs from that of the natural gene or its insertion results in "a knockout"). For example, a sequence of interest can be cDNA, DNA, or mRNA.

The term "sequence of interest" or "gene of interest" can also mean a nucleic acid sequence that is partly or entirely complementary to an endogenous gene of the cell into which it is introduced.

A "sequence of interest" or "gene of interest" can also include one or more transcriptional regulatory sequences and any other nucleic acid, such as introns, that may be necessary for optimal expression of a selected nucleic acid. A "protein of interest" means a peptide or polypeptide sequence that is expressed from a sequence of interest or gene of interest.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

As used herein, the terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription.

Suitable promoters can be derived from genes of the host cells where expression should occur or from pathogens for this host cells (e.g., tissue promoters or pathogens like viruses). If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem. The term "tissue specific" as it applies to a promoter refers to a promoter that is capable of directing selective expression of a nucleotide sequence or gene of interest to a specific type of tissue in the relative absence of expression of the same nucleotide sequence or gene of interest in a different type of tissue.

The phrase "at least" preceding a series of elements is to be understood to refer to every element in the series. For example, "at least one" includes one, two, three, four or more.

As used herein, the term "transgene" describes genetic material that has been or will be or is about to be inserted into the genome of a cell (e.g., a mammalian cells for implantation into a living animal).

As used herein, the term "transformation" refers to a permanent or transient genetic change induced in a cell following incorporation of exogenous DNA to the cell.

As used herein, the phrase "transgenic animal" refers to a non-human animal, generally, a mammal (e.g., mouse, rat, rabbit, etc.) having a non-endogenous (e.g., heterologous) nucleic acid sequence present as an extrachromosomal element in a portion of its cell or stably integrated into its germ line DNA (e.g., in the genomic sequence of most or all of its cells). The phrase "transgenic animal" also includes the founder transgenic non-human animal and progeny of the founders as well as cells, cell lines and tissues from such animals in which one or more of the cells of the animal includes one or more transgenes.

As used herein, "knock-out" of a gene means an alteration in the sequence of the gene or sequence associated with the gene that results in a decrease of function of the target gene. For example, the knock-out or ablation of gene can lead the expression of the target gene below detectable levels or where with expression level is present at insignificant levels.

As used herein, the phrase "variant small cell lung cancer" or "variant subtype" or small cell lung cancer variant subtype" or the like refers to a particular histopathology including but not limited to slightly larger cells than typical classic small cell lung cancer, single, centrally-located prominent nucleoli, well-defined eosinophilic cytoplasm.

"Small cell lung cancer classic subtype" can have the following expression profile: low NEUROD1, high ASCL1, high EPCAM, high neuroendocrine gene (s), high MYCL or MYCN, and low MYC. The classic phenotype can predict whether a subject will respond to a BCL2 inhibitor.

"Small cell lung cancer variant subtype" can have the following expression profile: high NEUROD1, low ASCL1, low EPCAM, low neuroendocrine gene(s), low MYCL or MYCN, and high MYC. The variant phenotype can predict whether a subject will respond to an aurora kinase inhibitor (e.g., alisertib).

MYCL (also known as LMYC, MYCL1, L-MYC) refers to L-myc-1 proto-oncogene protein, and is a protein encoded by the MYCL1 gene.

MYC (also known as MYCC and c-MYC) is a protein that is involved in cell cycle progression, apoptosis and cellular transformation.

MYCN (also known as N-Myc and NMYC) refers to N-myc proto-oncogene protein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, certain changes and modifications may be practiced within the scope of the appended claims.

Introduction

Small cell lung cancer (SCLC) has historically been treated therapeutically as a homogeneous disease without molecular stratification. SCLC has a dismal prognosis with no targeted therapies approved for treatment. Tumors uniformly lack RB1 and TP53 and frequently acquire genomic amplifications of a MYC family member including MYC, MYCL or MYCN. Described herein is a novel, MYC-driven genetically engineered mouse model (GEMM) that recapitulates key features of human SCLC. This model mimics a human SCLC subtype characterized by "variant" morphology, high NEUROD1 and low expression of neuroendocrine genes. Targeted drug screening revealed that MYC-driven SCLC is sensitive to Aurora kinase inhibitors, which improves chemotherapy response in vivo. Aurora kinase inhibition with first-line chemotherapy can be a novel therapeutic approach for MYC-driven SCLC.

Models for SCLC have been generated including cell lines, genetically engineered mouse models (GEMMs), and xenografts derived from patient tumors (PDX) or circulating tumor cells (CDX) (Gazdar et al., 2015; Hodgkinson et al., 2014). Human SCLC cell lines have been characterized as classic or variant, with variant lines exhibiting faster doubling times, frequent MYC amplification, reduced neuroendocrine marker expression and loosely aggregated morphology (Carney et al., 1985; Gazdar et al., 1985; Johnson et al., 1992; Johnson et al., 1996). Patients for which cell lines harbor MYC amplifications demonstrate poor survival compared to those without (Brennan et al., 1991; Johnson et al., 1987). The relationship of cell line morphology to human tumors and the factors that drive these phenotypes are not well understood; this is partly because biopsies from SCLC are small, infrequent and often derived from chemo-naïve patients. The classification of SCLC includes mixed or "combined" forms of SCLC (Travis et al., 2015), and it has been observed that about 10-20% of SCLCs may lack expression of diagnostic neuroendocrine markers (George et al., 2015; Rekhtman, 2010; Travis, 2009), but these phenotypes currently do not impact therapeutic decisions. Examples of neuroendocrine markers include but are limited to ASCL1, NEUROD1, SYP, INSM1, CHGA, SCG2, GRP, NCAM1, UCHL1 (PGP9.5), NSE and CALCA/B (CGRP alpha/beta).

Molecular signatures of tumor heterogeneity in SCLC have been discovered at the level of gene expression and methylation patterns, including an inverse relationship between the neurogenic transcription factors, Achaete-Scute Homologue 1 (ASCL1) and Neuronal Differentiation 1 (NEUROD1) (Borromeo et al., 2016; Poirier et al., 2013; Poirier et al., 2015). ASCL1, but not NEUROD1, is required for tumorigenesis in a mouse model of classic SCLC indicating that ASCL1 is a key driver of at least this subset of tumors (Borromeo et al., 2016). In contrast, NEUROD1$^{high}$ signatures are associated with variant morphology and MYC amplifications in human cell lines (Borromeo et al., 2016; Poirier et al., 2013). Mouse models, however, have not yielded variant, NEUROD1+ tumors, which has cast doubt on the relevance of this molecular subset (Borromeo et al., 2016; Bunn et al., 2016).

Conditional mouse models of SCLC are based on simultaneous loss of Rb1 and Trp53 in the mouse lung. Mice develop SCLC with long latency (e.g., 10-15 months) and tumors frequently harbor Mycl amplifications similar to human SCLC (Calbo et al., 2011; Dooley et al., 2011; Meuwissen et al., 2003). Mycl overexpression in Rb1$^{fl/fl}$; Trp53$^{fl/fl}$ mice using a chimeric model accelerates lung tumor formation, demonstrating that Mycl is a SCLC driver (Huijbers et al., 2014; Semenova et al., 2015). In cooperation with Rb1 and Trp53 loss, deletion of the Rb1 family member Rbl2 (p130) or the Pten tumor suppressor shortens tumor latency but mice also develop variable histological subtypes (Cui et al., 2014; Gazdar et al., 2015; McFadden et al., 2014; Schaffer et al., 2010). These mouse models of high-grade neuroendocrine lung carcinomas have been classified histopathologically as classic SCLC, large cell neuroendocrine carcinoma (LCNEC) or non-small cell lung cancer with neuroendocrine features (NSCLC-NE), but to date none has demonstrated variant SCLC pathology (Bunn et al., 2016; Gazdar et al., 2015). Described herein is a new GEMM of SCLC and use integrated genomic and transcriptomic analyses of human and murine SCLC that can be used to determine the impact of MYC on clinical features of SCLC tumorigenesis and therapeutic response in vivo.

Loss of the tumor suppressors RB1 and TP53 and MYC amplification are frequent oncogenic events in small cell lung cancer (SCLC). The results described herein show that Myc expression cooperates with Rb1 and Trp53 loss in the mouse lung to promote aggressive, highly metastatic tumors that are initially sensitive to chemotherapy followed by relapse, similar to human SCLC. Importantly, Myc drives a neuroendocrine-low "variant" subset of SCLC with high NEUROD1 expression corresponding to transcriptional profiles of human SCLC. Targeted drug screening reveals that SCLC with high MYC expression can be vulnerable to Aurora kinase inhibition, which combined with chemotherapy strongly suppresses tumor progression and increases survival. These data identify molecular features for patient stratification and uncover a novel targeted treatment approach for MYC-driven SCLC.

Small Cell Lung Cancer

Common symptoms of small cell lung cancer (SCLC) include but are not limited to couch, dyspnea, weight loss and debility. SCLC can also present in some patients with metastatic disease including but not limited to the liver, lymph nodes, adrenal glands, bone and brain. Most cases of SCLC present in advanced stages, most patients are diagnosed based on small biopsy and cytology specimens. Two types of SCLC are recognized that include many different types of cells. One subtype referred to as "variant" subtype can be characterized by the following genotypic profile: a high (e.g., increased) NEUROD1 expression and low (e.g., reduced) expression of neuroendocrine genes (e.g., ASCL1) with MYC amplification. For example, the SCLC variant subtype can have the following genotypic expression profile: high NEUROD1, low ASCL1, low EPCAM, low neuroendocrine gene, low MYCL or MYCN, and high MYC as well as predict whether a subject will respond to certain therapeutic therapies, including treatment with, for instance, alisertib, an aurora kinase inhibitor. The other subtype referred to as "classic" subtype can be characterized by the expression of ASCL1 with Mycl-amplifications. For example, the SCLC classic subtype can have the following genotypic expression profile: low NEUROD1, high ASCL1, high EPCAM, high neuroendocrine gene, high MYCL or MYCN, and low MYC as well as predict whether a subject will respond to certain therapeutic therapies, including treatment with, for instance, a BCL2 inhibitor.

Figure 1B:
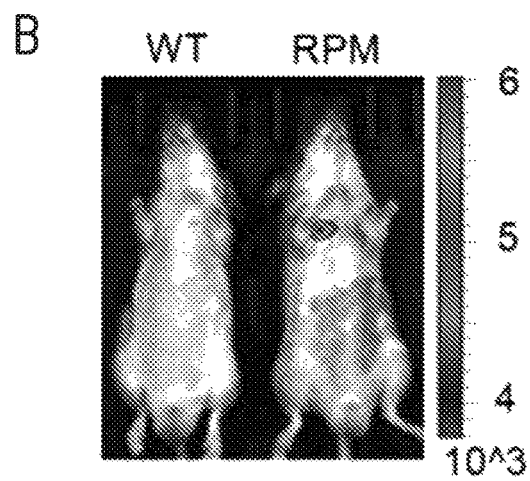
Figure 1C:
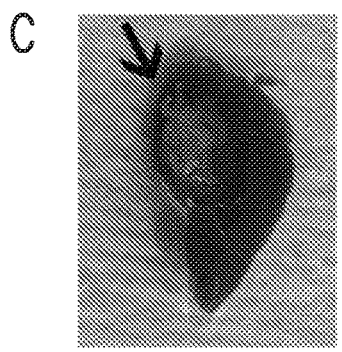
Figure 1D:
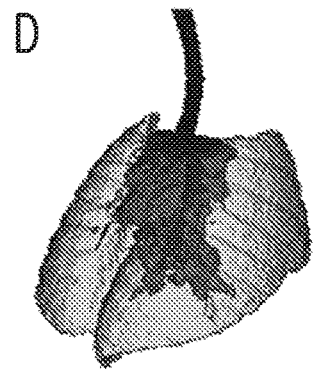
Figure 1E:
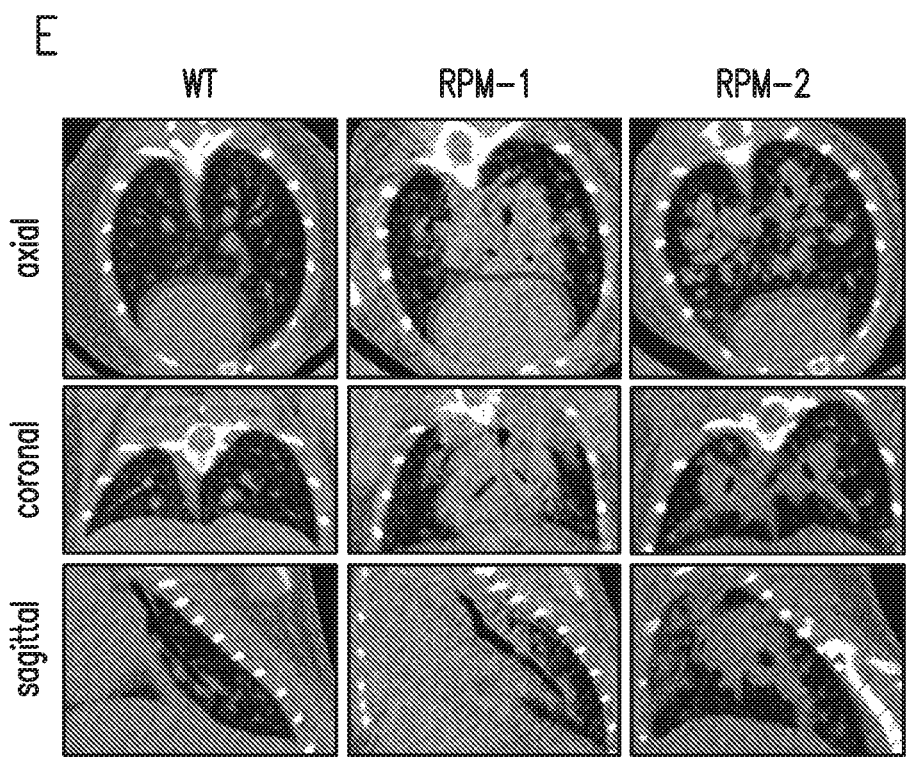
Figure 1F:
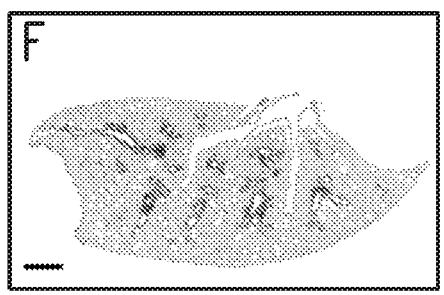
Figure 1G:
Figure 1H:
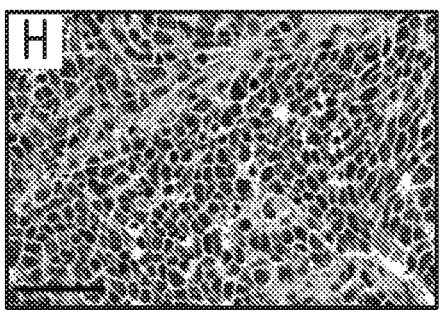

Classic and variant refer to histopathological appearance as viewed in H&E stained sections. Typical "classic" SCLC includes small cells, scant ill-defined cytoplasm, finely granular nuclear chromatin and inconspicuous nucleoli (Travis, 2012) (FIG. 1H). Variant SCLC consists of slightly larger cells with single, centrally located prominent nucleoli and well-defined eosinophilic cytoplasm, similar to what has been described as the variant form of SCLC. The data described herein shows that "variant" histopathology also correlates with NEUROD1 expression, and relatively low levels of most other neuroendocrine markers including, for example, ASCL1. In addition, there is a tight correlation with high MYC expression and/or amplifications with the variant subtype so all of these parameters can serve as signatures.

Methods

Disclosed herein is a transgenic mouse and methods of producing a transgenic mouse. Disclosed herein are non-human transgenic animal models useful for screening drugs or candidate drugs and diagnosing patient populations. In an aspect, the transgenic mouse comprises a genome wherein both alleles of endogenous Rb1 and Trp53 genes are ablated; and a transgene expressing an exogenous Myc gene operably linked to a regulatory sequence (or element) which permits expression of the Myc gene upon exposure to Cre recombinase in lung cells, wherein the exogenous Myc gene is expressed in said transgenic mouse. In an aspect, the exogenous Myc gene comprises a T58A mutation. In an aspect, the exogenous Myc gene comprises a wildtype Myc gene. A transgene can be used to transform a cell so that a genetic change can be present in the induced cell following incorporation of exogenous DNA. A permanent genetic change can be induced in a cell following incorporation of exogenous DNA, for example, into the genome of the cell. Vectors for stable integration include but are not limited to plasmids, retroviruses, other animal viruses, etc.

As used herein, the term "regulatory element" or "regulatory sequence" refers to promoters, promoter enhancers, internal ribosomal entry sites (IRES) and other elements that are capable of controlling expression (e.g., transcription termination signals, including but not limited to polyadenylation signals and poly-U sequences). Regulatory elements can direct constitutive expression. Regulatory element can also refer to enhancer elements. In an aspect, the regulatory sequence can be a neuroendocrine promoter. In an aspect, the neuroendocrine promoter can be calcitonin gene-related peptide. Generally, any constitutive promoter can be operably linked to a nucleotide sequence encoding a RNA-directed nuclease. Specific gene specific promoters can be used. Such promoters allow cell specific expression or expression tied to specific pathways. Any promoter that is active in mammalian cells can be used. Any promoter that can control the expression of Cre recombinase in lung tissue or lung cells can be used. In an aspect, Cre recombinase can be driven by a neuroendocrine promoter. Examples of promoters include but are not limited to neuroendocrine promoter, surfactant protein C, club cell secretory protein, keratin 5 and cytomegalovirus. Examples of promoters that can be useful for gene expression include, but are not limited to, Rous sarcoma virus (RSV), SV40, herpes thymidine kinase promoter, β-lactamase promoter, the tac promoter, Gal 4 promoter, alcohol dehydrogenase promoter, phosphoglycerol kinase promoter, elongation factor-1 alpha promoter, cytomegalovirus promoter, and alkaline phosphatase promoter. Examples of promoters for controlling transcription from vectors in mammalian host cells can be obtained from various sources, for example, but not limited to the genomes of viruses such as polyoma, Simian Virus 40 (SV40), adenovirus, retroviruses, hepatitis-B virus and most preferably cytomegalovirus, or from heterologous mammalian promoters (e.g., beta actin promoter). Additionally, promoters from the host cell or related species can also be used.

Transgenic knock-outs can have partial or complete loss of function in one or both alleles of an endogenous gene. In an aspect, retinoblastoma (Rb1), a tumor suppressor gene, and Trp53, tumor protein 53, also, a tumor suppressor gene, can be knocked out or ablated. The knock-out can be achieved by a variety of mechanisms, including introduction of a disruption of the coding sequence, deletion of the coding sequence. "Knock-outs" can also include conditional knock-outs, for example, where alteration of a target gene or target genes occurs upon exposure of the animal to a substance that promotes target gene alteration, introduction of an enzyme that promotes recombination at the target gene site or other method for directing the target gene alteration.

Myc (also referred to as MYCC, c-Myc) is a regulator gene that codes for a transcription factor, and is known to have a direct role in the control of DNA replication. The exogenous Myc gene can be a human gene; it can also be a wild-type gene or a genetically manipulated sequence, for example, having deletions, substitutions or insertions in the coding or non-coding regions. The introduced sequence can encode a Myc polypeptide or can utilize the Myc promoter operably linked to a reporter gene. When the introduced gene is a coding sequence, it can be operably linked to promoter that can be constitutive or inducible, and other regulatory sequences required for expression into the host animal. In an aspect, the Myc gene can be a mutant Myc gene. In an aspect, the mutant Myc gene encodes a protein wherein a threonine to alanine substitution is at amino acid 58 (SEQ ID NO: 27). In an aspect, cre-recombinase can regulate MycT58A allele. An example of an amino acid with a T58A mutation can be the sequence of Accession Number NP 001170825.1. An example of an amino acid with a T58A mutation can be the sequence of (SEQ ID NO: 27)
MPLNVNFTNRNYDLDYDSVQPYFICDEEENFYHQQQQSELQPPAPSEDIW KKFELLP<u>A</u>PPLSPSRRSGLCSPSYVAVATSFSPREDDDGGGGNFSTADQL

EMMTELLGGDMVNQSFICDPDDETFIKNIIQDCMWSGFSAAAKLVSEKL

ASYQAARKDSTSLSPARGHSVCSTSSLYLQDLTAAASECIDPSVVFPYPL

NDSSSPKSCTSSDSTAFSPSSDSLLSSESSPRASPEPLVLHEETPPTTSS

DSEEEQEDEEEIDVVSVEKRQTPAKRSESGSSPSRGHSKPPHSPLVLKRC

HVSTHQHNYAAPPSTRKDYPAAKRAKLDSGRVLKQISNNRKCSSPRSSDT

EENDKRRTHNVLERQRRNELKRSFFALRDQIPELENNEKAPKVVILKKAT

AYILSIQADEFIKLTSEKDLLRKRREQLKHKLEQLRNSGA.

DNA constructs for homologous recombination can comprise at least a portion of the Myc gene with the desired genetic modification and can include regions of homology to the target locus. DNA constructs for random integration do not need to include regions of homology to mediate recombination. Methods for generating cells having targeted gene modifications through homologous recombination are known in the art.

In general, a transgenic animal is produced by the integration of a given transgene into the genome in a manner that permits the expression of the transgene. Methods for producing transgenic animals are known in the art.

In an aspect, the transgenic mouse disclosed herein can serve as a model of human SCLC. In an aspect, the transgenic mouse model disclosed herein can be the SCLC variant subtype.

In an aspect, the transgenic mouse can display between about 5 and 7 weeks of age, one or more centrally located lung tumors associated with small cell lung cancer (SCLC). In an aspect, the SCLC can be a SCLC subtype. In an aspect, the SCLC subtype can be a variant SCLC subtype. In an aspect, the transgenic mouse can express reduced expression of the neurogenic transcription factor ASCL1 and increased expression of NEUROD1. In an aspect, the transgenic mouse can express more MYC than MYCL. In an aspect, the expression level can be measured in the lung tumors obtained from the transgenic mouse. The expression levels of any of the genes or proteins described herein from the transgenic non-human animal or any cells derived thereof can be measured and subsequently compared to the expression level in a wild-type or otherwise healthy or normal non-human animal or cell or cell line.

Vectors can include plasmids, cosmids, and viruses (e.g., bacteriophage, animal viruses, and plant viruses), and artificial chromosomes (e.g., YACs). Vectors can comprise targeting molecules. A targeting molecule is one that directs the desired nucleic acid to a particular organ, tissue, cell, or other location in a subject's body. A vector, generally, brings about replication when it is associated with the proper control elements (e.g., a promoter, a stop codon, and a polyadenylation signal). Examples of vectors that are routinely used in the art include plasmids and viruses. The term "vector" includes expression vectors and refers to a vector containing a nucleic acid sequence coding for at least part of a gene product capable of being transcribed. A variety of ways can be used to introduce an expression vector into cells. In an aspect, the expression vector comprises a virus or an engineered vector derived from a viral genome. As used herein, "expression vector" is a vector that includes a regulatory region. A variety of host/expression vector combinations can be used to express the nucleic acid sequences disclosed herein. Examples of expression vectors include but are not limited to plasmids and viral vectors derived from, for example, bacteriophages, retroviruses (e.g., lentiviruses), and other viruses (e.g., adenoviruses, poxviruses, herpesviruses and adeno-associated viruses). Vectors and expression systems are commercially available and known to one skilled in the art.

A detectable marker or label can be introduced into the locus, where upregulation of expression can result in a detected change in the phenotype. Any of the vectors disclosed herein can also include a detectable marker or label. Such detectable labels can include but are limited to a tag sequence designed for detection (e.g., purification or localization) of an expressed polypeptide. Tag sequences include, for example, green fluorescent protein, glutathione S-transferase, polyhistidine, c-myc, hemagglutinin, or Flag™ tag, and can be fused with the encoded polypeptide and inserted anywhere within the polypeptide, including at either the carboxyl or amino terminus. The label can comprise any detectable moiety, including, for example, fluorescent labels, radioactive labels, and electronic labels.

The DNA sequences encoding the Myc gene can be cDNA or genomic DNA or a fragment thereof. In an aspect, the DNA sequence can be MYC T58A cDNA. In an aspect, the DNA sequence encodes the wild type MYC. In an aspect, the gene or genes described herein can be introduced into an appropriate vector for integration into the host. Examples of vectors include but are not limited to viruses. In an aspect, a virus comprising Cre recombinase operably linked to any promoter can be delivered to lung or lung cells. Cre recombinase can be used to carry out site specific recombination events. For example, the mouse Myc wild-type Gene (Gene ID #17869) produces multiple transcripts with the accession numbers below: NM_010849.4→NP_034979.3, myc proto-oncogene protein isoform a; NM_001177354.1→NP_001170825.1, myc proto-oncogene protein isoform b; NM_001177353.1→NP_001170824.1; myc proto-oncogene protein isoform c; and NM_001177352.1→NP_001170823.1, myc proto-oncogene protein isoform b.

Disclosed herein are cell lines or primary cell cultures. In an aspect, the cell lines or primary cell cultures can be derived from the transgenic mouse described herein. In an aspect, cells or cell lines can be isolated from the transgenic animal. In an aspect, the cells or primary cell cultures are mammalian cells (e.g., mouse cell lines) that harbor an exogenous Myc gene. In an aspect, the Myc gene can be a mutant Myc gene. In an aspect, the mutant Myc gene comprises a T28A mutation. In an aspect, the Myc gene can be a wild-type gene. In an aspect, the cell lines or primary cell cultures comprise inactivated tumor suppressor genes. In an aspect, the inactivated tumor suppressor genes can be Rb1 and Trp53. In an aspect, the cell line can express one or more neuroendocrine biomarkers. Examples of neuroendocrine markers (e.g., gene panel) include but are limited to ASCL1, NEUROD1, SYP, INSM1, CHGA, SCG2, GRP, NCAM1, UCHL1 (PGP9.5), NSE and CALCA/B (CGRP alpha/beta). In an aspect, the cell line can express NEUROD1. In an aspect, the cell line does not express NEUROD1. In an aspect, the cell line can express low levels of one or more of the neuroendocrine markers (e.g., gene panel) disclosed herein. In an aspect, the cell line can express low levels of ASCL1. In an aspect, the cell line does not express or exhibits a reduced expression of ASCL1 compared to a reference cell line. In an aspect, the cell line can express high levels of MYC. In an aspect, the cell line can express high levels of NEUROD1. In an aspect, the cell line can be a model of SCLC variant subtype. In an aspect, the cell line can lack expression of ASCL1, NEUROD1 and/or most neuroendocrine markers disclosed herein. In an aspect, the cell line described herein can represent a subclass of human tumors, and for, example can lack expression of ASCL1 and NEUROD1, and have high MYC expression levels.

The cells lines described herein can be used for a variety of purposes including, but not limited to surveying human tissue or human circulating tumor cells and the like.

ASCL1 (also referred to as achaete-scute homolog 1) is a transcription factor involved in neuronal development and neuroblast formation.

NEUROD1 (also referred to as neurogenic differentiation 1, and sometimes called (32) is a transcription factor of the NeuroD-type.

SYP (also referred to as synaptophysin) encodes major synaptic vesicle protein p38 that is a synaptic vesicle glycoprotein.

INSM1 (also referred to as insulinoma-associated protein 1) is an intronless gene that serves as a biomarker for differentiating human lung tumors.

CHGA (also referred to as chromogranin A or CgA or parathyroid secretory protein 1) is a member of the granin family of neuroendocrine secretory proteins.

SCG2 (also referred to as secretogranin II and chromogranin C) is a gene that encodes a neuroendocrine secretory protein.

GRP (also referred to as pro-gastrin releasing peptide or ProGRP) encodes a regulatory human peptide involved in the release of gastrin.

NCAM1 (also referred to as neural cell adhesion molecule or CD56) is involved in cell adhesion, neurite outgrowth, synaptic plasticity and learning and memory.

UCHL1 (also referred to ubiquitin carboxy-terminal hydrolase L1 and PGP9.5) encodes a deubiquitinating enzyme.

NSE (also known as neuron specific enolase) is a phosphopyruvate hydratase encoded in humans by the ENO2 gene.

CALCA/B (also referred to as calcitonin gene-related peptide (CGRP)) exists in two form, alpha and beta.

The transgenic mouse models described herein can also be used to test the role of other genes in SCLC by using viruses, for example, to manipulate the gene or genes of interest or by crossing to another genetically engineered mouse. The tumors produced in the transgenic mouse models described herein can be harvested and further analyzed. Similarly, the circulating tumor cells present in the circulatory system of the transgenic mouse models described herein can also be removed and analyzed.

The transgenic mouse models described herein can be used to study all tumor-related process including but not limited to tumor microenvironment, tumor immunology, metastases, tumor progression, tumor initiation, gene function, tumor genomics, etc.

Methods of Screening

Disclosed herein are methods of screening for a biologically active agent for the treatment of small cell lung cancer. Also, disclosed herein are methods for identifying biologically active agents or compounds (e.g., peptides, cyclic peptides, peptidomimetics, small molecules, small organic molecules, or other drugs) which effect (e.g., modulate, inhibit, reduce, prevent or reduce or increase) the outcome of SCLC or one or more of the signs and symptoms of SCLC. In an aspect, the method comprises: administering a candidate agent with a transgenic mouse comprising: a genome wherein both alleles of endogenous Rb1 and Trp53 genes are ablated; and a transgene expressing an exogenous Myc gene operably linked to a regulatory sequence which directs expression of the exogenous gene in lung cells, wherein agents that increase survival or reduce tumor size are identified as effective for the treatment of small cell lung cancer. In an aspect, NEUROD1 can be expressed in the transgenic mouse. In an aspect, Mycl may not be expressed (e.g., is negative) or is reduced or is expressed at a low level in the transgenic mouse. In an aspect, ASCL1 can be expressed. The changes in survival and/or tumor size can be compared to animals administered a placebo. Agents or compounds identified as described herein can be used in an animal model to determine the mechanism of action, efficacy, toxicity or side effects of treatment with said agents or compounds.

Test compounds can be formulated into pharmaceutical compositions by admixture with pharmaceutically acceptable non-toxic excipients or carriers and administered to transgenic non-human animals described herein by any route of administration. For example, parenteral routes such as subcutaneous, intramuscular, intravascular, intradermal, intranasal, inhalation, intrathecal, or intraperitoneal administration, and enteral routes such as sublingual, oral, or rectal administration can be used.

Disclosed herein are methods of screening for a biologically active agent effective for the treatment of SCLC. In an aspect, the method comprises using the transgenic mouse disclosed herein. In an aspect, the transgenic mouse comprises a genome wherein both alleles of endogenous Rb1 and Trp53 genes are ablated; a transgene expressing an exogenous Myc gene comprising a T58 mutation operably linked to a regulatory sequence which directs expression of the exogenous Myc gene in lung cells, wherein the exogenous Myc gene is expressed in said transgenic mouse.

Also described herein, are in vitro screening methods. Disclosed herein are methods of screening for a biologically active agent effective for the treatment of small cell lung cancer. In an aspect, the method comprises: contacting a candidate agent with a transgenic mouse cell line comprising: a genome wherein both alleles of endogenous Rb1 and Trp53 genes are ablated; and a transgene expressing an exogenous Myc gene operably linked to a regulatory sequence which directs expression of the exogenous gene in lung cells, wherein agents that inhibit aurora kinase relative to an untreated sample of the transgenic cell line are identified as effective for the treatment of small cell lung cancer. In an aspect, the cells can be contacted with the candidate agent for about between 72 to 96 hours. In an aspect, the cells can be contacted with the candidate agent for 1, 2, 3, 4, 5, 10, 15, 20, 25, 30, 40, 50, 60, 70, 80, 90, 100, 200 hours or any time period in between. Agents or compounds identified as described herein can be used in an animal model to determine the mechanism of action, efficacy, toxicity or side effects of treatment with said agents or compounds.

Disclosed herein are methods of screening for a biologically active agent for the treatment of SCLC. In an aspect, the method comprises: a. determining the expression of aurora kinase in a transgenic mouse cell line comprising: a genome wherein both alleles of endogenous Rb1 and Trp53 genes are ablated; and a transgene expressing an exogenous Myc gene operably linked to a regulatory sequence which directs expression of the exogenous gene in lung cells; b.

contacting a biologically active agent with the transgenic mouse cell line; c. determining the expression of aurora kinase in the transgenic mouse cell line after step (b). The method can further comprises the step of correlating the level of aurora kinase in the transgenic mouse cell line of step (a) with the level of aurora kinase in the transgenic mouse cell line of step (c), wherein a decrease in the level of aurora kinase in step (c) compared to step (a) indicates that the biologically active agent is likely to be effective for the treatment of SCLC.

Disclosed herein are methods of detecting small cell lung cancer in a subject. In an aspect, the methods described herein can detect SCLC. In an aspect, the SCLC can be the classic SCLC. For example, the data and findings disclosed herein shows, in part, a correlation of EPCAM expression with the classic SCLC subtype. Thus, EPCAM expression can be used to correlate with ASCL1 expression and low neuroendocrine gene expression, and correspondingly is very low or negative in MYC-driven SCLC. Since EPCAM is a surface marker, it can also be used as a biomarker for classic SCLC.

In an aspect, the methods described herein can detect a clinical subtype of SCLC. In an aspect, the SCLC can be variant subtype. In an aspect, the method comprises obtaining a sample from a human subject; and detecting the presence or absence of one or more neuroendocrine biomarkers and Myc family of transcription factors in the sample. In an aspect, the presence of NEUROD1 and the absence of Mycl can be detected. In an aspect, expression level of NEUROD1 can be increased and the expression level of Mycl can be reduced. The expression level of the sample can be compared to a reference sample. A variety of methods can be used to detect one or more neuroendocrine biomarkers and Myc family of transcription factors in a sample. In an aspect, the detection can be determined using RNA-sequence data analysis or polymerase chain reaction. In an aspect, the sample can be a blood or lung tissue sample.

In an aspect, the method can include the step of determining the level of NEUROD1, Myc or Mycl, and ASCL1 in the subject's sample. In an aspect, the method can include determining the level of one or more of the neuroendocrine genes disclosed herein. In an aspect, the method can include determining the level of EPCAM. In an aspect, the method can include determining the level of any one of the biomarkers disclosed herein including but not limited to NEUROD1, Myc, Mycl, ASCL1, EPCAM and one or more additional neuroendocrine genes disclosed herein or a combination thereof. The method can further include the step of comparing the levels of, for example, NEUROD1, Myc or Mycl, and ASCL1 (or any of NEUROD1, Myc, Mycl, ASCL1, EPCAM and one or more additional neuroendocrine genes disclosed herein or a combination thereof) of the subject's sample to a sample from a human subject that does not have SCLC. In an aspect, an increased level of NEUROD1, an increased level of Myc or Mycl and a decreased level of ASCL1 in the subject's sample indicates that the subject has a variant subtype of SCLC.

In an aspect, the level of NEUROD1, Myc or Mycl, and ASCL1 (or any of NEUROD1, Myc, Mycl, ASCL1, EPCAM and one or more additional neuroendocrine genes disclosed herein or a combination thereof) can be determined using RNA-sequence data analysis or polymerase chain reaction.

In an aspect, the method can further comprise treating the subject with an aurora kinase inhibitor or a BCL-2 inhibitor.

Procedures for the extraction and collection of a sample of a subject's lung tissue or blood can be done by methods known in the art. Lung tissue obtained via biopsy is standard practice. Frozen tissue specimens can also be used. The sample can be whole cells or cell organelles. Cells can be collected by scraping the tissue, processing the tissue sample to release individual cells or isolating the cells from a bodily fluid. The sample can be fresh tissue, dry tissue, cultured cells or tissue. The sample can be unfixed or fixed. Any part of the lung can be obtained and assessed using the methods described herein.

As used herein, the term "expression," when used in the context of determining or detecting the expression or expression level of one or more genes, can refer to determining or detecting transcription of the gene (i.e., determining mRNA levels) and/or determining or detecting translation of the gene (e.g., determining or detecting the protein produced). To determine the expression level of a gene means to determine whether or not a gene is expressed, and if expressed, to what relative degree. The expression level of one or more genes disclosed herein can be determined directly (e.g., immunoassays, mass spectrometry) or indirectly (e.g., determining the mRNA expression of a protein or peptide). Examples of mass spectrometry include ionization sources such as EI, CI, MALDI, ESI, and analysis such as Quad, ion trap, TOF, FT or combinations thereof, spectrometry, isotope ratio mass spectrometry (IRMS), thermal ionization mass spectrometry (TIMS), spark source mass spectrometry, Multiple Reaction Monitoring (MRM) or SRM. Any of these techniques can be carried out in combination with prefractionation or enrichment methods. Examples of immunoassays include immunoblots, Western blots, Enzyme linked Immunosorbant Assay (ELISA), Enzyme immunoassay (EIA), radioimmune assay. Immunoassay methods use antibodies for detection and determination of levels of an antigen are known in the art. The antibody can be immobilized on a solid support such as a stick, plate, bead, microbead or array.

Expression levels of one or more of the genes described herein can be also be determined indirectly by determining the mRNA expression for the one or more genes in a tissue sample. RNA expression methods include but are not limited to extraction of cellular mRNA and Northern blotting using labeled probes that hybridize to transcripts encoding all or part of the gene, amplification of mRNA using gene-specific primers, polymerase chain reaction (PCR), and reverse transcriptase-polymerase chain reaction (RT-PCR), followed by quantitative detection of the gene product by a variety of methods; extraction of RNA from cells, followed by labeling, and then used to probe cDNA or olignonucleotides encoding the gene, in situ hybridization; RNA-sequencing; and detection of a reporter gene.

Methods to measure protein expression levels include but are not limited to Western blot, immunoblot, ELISA, radioimmunoassay, immunoprecipitation, surface plasmon resonance, chemiluminescence, fluorescent polarization, phosphorescence, immunohistochemical analysis, microcytometry, microarray, microscopy, fluorescence activated cell sorting (FACS), and flow cytometry. The method can also include specific protein property-based assays based including but not limited to enzymatic activity or interaction with other protein partners. Binding assays can also be used, and are well known in the art. For instance, a BIAcore machine can be used to determine the binding constant of a complex between two proteins. Other suitable assays for determining or detecting the binding of one protein to another include, immunoassays, such as ELISA and radioimmunoassays. Determining binding by monitoring the change in the spectroscopic can be used or optical properties of the proteins can be determined via fluorescence, UV absorption, circular dichroism, or nuclear magnetic resonance (NMR). Alternatively, immunoassays using specific antibody can be used to detect the expression on of a particular protein on a tumor cell.

As used herein, the term "reference," "reference expression," "reference sample," "reference value," "control," "control sample" and the like, when used in the context of a sample or expression level of one or more genes or proteins refers to a reference standard wherein the reference is expressed at a constant level among different (i.e., not the same tissue, but multiple tissues) tissues, and is unaffected by the experimental conditions, and is indicative of the level in a sample of a predetermined disease status (e.g., not suffering from SCLC). The reference value can be a predetermined standard value or a range of predetermined standard values, representing no illness, or a predetermined type or severity of illness.

Reference expression can be the level of the one or more genes described herein in a reference sample from a subject, or a pool of subjects, not suffering from SCLC or from a predetermined severity or type of SCLC. In an aspect, the reference value is the level of one or more genes disclosed herein in the tissue of a subject, or subjects, wherein the subject or subjects is not suffering from SCLC.

Determining the expression level of one or more genes disclosed herein can include determining whether the gene is upregulated or increased as compared to a control or reference sample, downregulated or decreased (e.g., low) compared to a control or reference sample, or unchanged compared to a control or reference sample. As used herein, the terms, "upregulated" and "increased expression level" or "increased level of expression" refers to a sequence corresponding to one or more genes disclosed herein that is expressed wherein the measure of the quantity of the sequence exhibits an increased level of expression (e.g., high) when compared to a reference sample or "normal" control. For example, the terms, "upregulated" and "increased expression level" or "increased level of expression" refers to a sequence corresponding to one or more genes disclosed herein that is expressed wherein the measure of the quantity of the sequence exhibits an increased level of expression of one or more of protein(s) and/or mRNA when compared to the expression of the same mRNA(s) from a reference sample or "normal" control. An "increased expression level" refers to an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. As used herein, the terms "downregulated," "decreased level 5 of expression," or "decreased expression level" refers to a sequence corresponding to one or more genes disclosed herein that is expressed wherein the measure of the quantity of the sequence exhibits a decreased level of expression when compared to a reference sample or "normal" control. For example, the terms, "downregulated," "decreased level of expression," or "decreased expression level" refers to a sequence corresponding to one or more genes disclosed herein that is expressed wherein the measure of the quantity of the sequence exhibits a decreased level of expression of one or more protein(s) and/or mRNA when compared to the expression of the same mRNA(s) from a reference sample or "normal" control. A "decreased level of expression" refers to a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more.

Disclosed herein are methods of diagnosing a patient with small cell lung cancer. In an aspect, the method comprises: obtaining a sample from a human subject; detecting whether one or more neuroendocrine biomarkers or Myc family of transcription factors is present in the sample; and diagnosing the subject with small cell lung cancer when the presence of one or more neuroendocrine biomarkers or Myc family of transcription factors is detected. In an aspect, the presence of NEUROD1 and the absence of Mycl can be detected. In an aspect, the sample can be a blood or lung tissue sample. In an aspect, the detection can be determined using RNA-sequence data analysis or polymerase chain reaction.

Signature pattern(s) of increased (higher) or decreased (lower) sample expression levels of one or more of genes when compared to the reference expression levels of one or more of genes can be observed and indicate SCLC and/or the subtype of SCLC in a subject.

In an aspect, decreased expression level of NEUROD1 and MYC, and increased expression level of ASCL1, EPCAM, one or more neuroendocrine genes, MYCL or MYCN indicate the classic SCLC subtype.

In an aspect, increased expression level of NEUROD1 and MYC, and decreased expression level of ASCL1, EPCAM, one or more neuroendocrine genes, MYCL or MYCN indicate the variant SCLC subtype.

The expression level of one or more genes described herein can be a measure of one or more genes, for example, per unit weight or volume. In an aspect, the expression level can be a ratio (e.g., the amount of one or more genes in a sample relative to the amount of the one or more markers of a reference value).

The methods described herein can further comprise the step of assaying the lung tissue sample from the subject to detect the presence of other molecular features of SCLC and/or a SCLC subtype.

In an aspect, the lung tissue sample can be SCLC. In an aspect, the lung tissue sample can be a tumor. In an aspect, the lung tissue sample and/or tumor can be a SCLC subtype. In an aspect, the SCLC subtype can be the variant subtype. The SCLC variant subtype can be characterized by high levels of MYC, which may be from genomic amplification or high levels of MYC mRNA. In an aspect, the SCLC variant subtype can also have low ASCL1 and/or MYCL expression and low expression of other neuroendocrine markers described herein. In an aspect, the lung tissue sample can also have high expression of NEUROD1. The SCLC variant subtype also can have variant histopathology. In an aspect, the SCLC subtype can have an increased likelihood to be sensitive to Aurora kinase inhibition.

In an aspect, the SCLC subtype can be the classic subtype. The SCLC classic subtype can be characterized by high levels of MYCL. In an aspect, the SCLC classic subtype can also express high levels of MYCN. Further, the SCLC classic subtype can be genomic amplifications in MYCL or high levels of MYCL mRNA. SCLC classic subtype tumors can also have high expression of ASCL1 and other neuroendocrine markers described herein. The SCLC classic subtype can have classic histopathology. In an aspect, the SCLC class subtype can have high expression of EPCAM. and/or high expression of BCL2. In an aspect, the SCLC classic subtype can have an increased likelihood of being responsive to BCL2 inhibitors.

Methods of Treating

Disclosed herein are methods of treating a subject or patient. In an aspect, the subject or patient is a human.

Disclosed herein are methods of identifying a patient with small cell lung cancer in need of treatment. In an aspect, the method comprises identifying a patient having high expression of NEUROD1 or MYC and lacking expression of Mycl or ASCL1; and administering to the patient a therapeutically effective amount of an aurora kinase inhibitor. In an aspect, the patient can be a human patient. In an aspect, the method can further comprise the step of administering one or more chemotherapeutic agents. In an aspect, the expression of NEUROD1, MYC, Mycl, ASCL1, and EPCAM can be determined using RNA-sequence data analysis or polymerase chain reaction.

Any of the methods of detecting gene or protein expression can be used to identify a patient in need of treatment. In an aspect, the treatment can be the administration of a therapeutically effective amount of an aurora kinase inhibitor.

Disclosed herein are methods of treating a patient with small cell lung cancer. In an aspect, the method comprises identifying a patient in need of treatment; and administering to the patient a therapeutically effective amount of an aurora kinase inhibitor. In an aspect, the patient can be a human patient. In an aspect, the method can further comprise the step of administering one or more chemotherapeutic agents.

Disclosed herein are methods of treating a patient with a variant small cell lung cancer. In an aspect, the method comprises identifying a patient in need of treatment; and administering to the patient a therapeutically effective amount of an aurora kinase inhibitor. In an aspect, the patient with variant SCLC has an increased level of NEUROD1, an increased level of Myc or a decreased level of Mycl, and a decreased level of ASCL1 compared to a reference sample. In an aspect, the level of NEUROD1, Myc or Mycl, and ASCL1 (or any of NEUROD1, Myc, Mycl, ASCL1, EPCAM and one or more additional neuroendocrine genes disclosed herein) or a combination thereof can be determined and compared.

Aurora kinase is an enzyme involved in cell proliferation, and is a known target in the treatment of a variety of cancers. Three aurora kinase genes have been identified, A, B, and C with A and B have been shown to play a role in oncogenesis. Examples of aurora kinase inhibitors include but are not limited to ZM447439, hesperidin, VX-680, alisertib (MLN8237), barasertib (AZD1152-HQPA) or derivatives thereof.

Changes in biomarker expression or amplification can be used to indicate that a subject may be sensitive to the administration of an aurora kinase inhibitor. In an aspect, increased or high expression of MYC, MYC amplification and/or NEUROD1 can indicate a SCLC variant (e.g., cMYC) and/or an aurora kinase inhibitor sensitivity in a patient with SCLC. In an aspect, decreased or low expression of ASCL1, one or more neuroendocrine panel of genes described herein and/or EPCAM can indicate a SCLC variant (e.g., cMYC) and/or an aurora kinase inhibitor sensitivity in a patient with SCLC. In an aspect, a combination of increased or high expression of MYC, MYC amplification and/or NEUROD1; and decreased or low expression of ASCL1, one or more neuroendocrine panel of genes described herein and/or EPCAM can indicate a SCLC variant (e.g., cMYC) and/or an aurora kinase inhibitor sensitivity in a patient with SCLC. Any of these changes in biomarker expression or amplification described herein can be combined with histopathological changes that indicate a variant morphology to indicate a SCLC variant (e.g., cMYC) and/or an aurora kinase inhibitor sensitivity in a patient with SCLC.

EPCAM is also known as epithelial cell adhesion molecule involved in many cellular functions including but not limited to cell signaling, migration, proliferation and differentiation. EPCAM may play role in the development of tumors and in metastasis of carcinomas. EPCAM expression can be upregulated in cancer. Blood flows through the lungs and, thus, can contain malignant cells. In an aspect, EPCAM can serve as a biomarker for SCLC, and differentiating lung cancer subtypes.

In an aspect, EPCAM can be highly expressed in MYCL-associated, classic SCLC. In an aspect, EPCAM protein expression can be highly correlated with all of the SCLC classic subtype signatures including but not limited to ASCL1 and high expression of one or more neuroendocrine genes disclosed herein. In an aspect, EPCAM can be low or negative in MYC-associated, SCLC variant subtype. In an aspect, EPCAM low or negative tumors can indicate sensitivity in a patient to aurora kinase inhibition. In an aspect, BCL2 expression can highly correlate with the MYCL-associated, SCLC classic subtype and all of its signatures including but not limited to ASCL1 expression. In an aspect, low BCL2 expression can indicate sensitivity in a patient to aurora kinase inhibition.

Methods of Determining Success of Therapies

Disclosed herein are methods of predicting a small cell lung cancer patient's responsiveness to an aurora kinase inhibitor therapy. In an aspect, the method comprises obtaining a sample from the patient; determining the level of (i) NEUROD1, (ii) Myc or Mycl, and (iii) ASCL1 in the patient's sample; comparing the levels of (i) NEUROD1, (ii) Myc or Mycl and (iii) ASCL1 of the patient's sample to a sample from a human subject that does not have small cell lung cancer. An increased level of NEUROD1, an increased level of Myc and a decreased level of ASCL1 in the patient's sample indicates that the subject is likely to respond to an aurora kinase inhibitor therapy. In an aspect, the level of NEUROD1, Myc or Mycl, and ASCL1 (or any of NEUROD1, Myc, Mycl, ASCL1, EPCAM and one or more additional neuroendocrine genes disclosed herein) or a combination thereof can be determined and compared.

Disclosed herein are methods of SCLC's patient's responsiveness to a BCL-2 inhibitor therapy. In an aspect, the method comprises obtaining a sample from the patient; determining the level of (i) NEUROD1, (ii) Myc or Mycl, and (iii) ASCL1 in the patient's sample; comparing the levels of (i) NEUROD1, (ii) Myc or Mycl and (iii) ASCL1 of the patient's sample to a sample from a human subject that does not have small cell lung cancer. A decreased level of NEUROD1 or Myc and an increased level of Mycl or an increased level of ASCL1 in the patient's sample indicates that the BCL-2 inhibitor therapy will be successful in the patient. In an aspect, the level of NEUROD1, Myc or Mycl, and ASCL1 (or any of NEUROD1, Myc, Mycl, ASCL1, EPCAM and one or more additional neuroendocrine genes disclosed herein) or a combination thereof can be determined and compared. In an aspect, an increased level of EPCAM or one or more of the neuroendocrine genes disclosed herein in the patient's sample indicates that the BCL-2 inhibitor therapy will be successful in the patient.

Disclosed herein are methods of predicting the success of an aurora kinase inhibitor therapy in a patient with SCLC. In an aspect, the method comprises obtaining a sample from the patient; determining the level of (i) NEUROD1, (ii) Myc or Mycl, and (iii) ASCL1 in the patient's sample; comparing the levels of (i) NEUROD1, (ii) Myc or Mycl and (iii) ASCL1 of the patient's sample to a sample from a human subject that does not have small cell lung cancer. An increased level of NEUROD1, an increased level of Myc and a decreased level of ASCL1 and a decreased level of Mycl in the patient's sample indicates that the aurora kinase inhibitor therapy will be successful in the patient. In an aspect, the level of NEUROD1, Myc or Mycl, and ASCL1 (or any of NEUROD1, Myc, Mycl, ASCL1, EPCAM and one or more additional neuroendocrine genes disclosed herein) or a combination thereof can be determined and compared. In an aspect, a decreased level of EPCAM or one more of the neuroendocrine genes disclosed herein in the patient's sample indicates that the aurora kinase inhibitor therapy will be successful in the patient.

Disclosed herein are methods of predicting the success of a BCL-2 inhibitor therapy in a patient with SCLC. In an aspect, the method comprises obtaining a sample from the patient; determining the level of (i) NEUROD1, (ii) Myc or Mycl, and (iii) ASCL1 in the patient's sample; comparing the levels of (i) NEUROD1, (ii) Myc or Mycl and (iii) ASCL1 of the patient's sample to a sample from a human subject that does not have small cell lung cancer. An decreased level of NEUROD1 or Myc, and an increased level of Mycl or ASCL1 in the patient's sample indicates that the BCL-2 inhibitor therapy will be successful in the patient. In an aspect, the level of NEUROD1, Myc or Mycl, and ASCL1 (or any of NEUROD1, Myc, Mycl, ASCL1, EPCAM and one or more additional neuroendocrine genes disclosed herein) or a combination thereof can be determined and compared. In an aspect, an increased level of EPCAM or one more of the neuroendocrine genes disclosed herein in the patient's sample indicates that the BCL-2 inhibitor therapy will be successful in the patient.

EXAMPLES

Example 1: Myc Promotes Rapid SCLC in Cooperation with Rb1 and Trp53 Loss

Figures 8C, 8D:
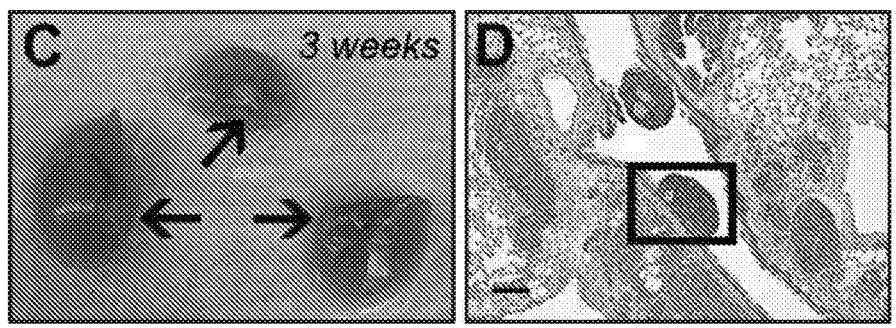
FIG. 8C shows a brightfield image of dissected lungs from RPM mice with tumors in the airway indicated by black arrows at 3 weeks post-infection.
FIGS. 8D-E are representative H&E images of 3-week classic lesion. Area in black box magnified in panel E. Scale bars are 100 and 50 µm, respectively.

Knock-in Lox-Stop-Lox (LSL)-Myc$^{T58A}$-IRES-Luciferase mice that carry a Cre recombinase regulatable Myc$^{T58A}$ allele in the H11 locus (FIG. 8A) were generated. These mice were crossed to Rb1$^{fl/fl}$Trp53$^{fl/fl}$ animals to generate Rb1$^{fl/fl}$Trp53$^{fl/fl}$Myc$^{LSL/LSL}$ (RPM) mice. At six weeks of age, mice were infected intratracheally with adenoviruses carrying Cre driven by a neuroendocrine Calcitonin gene-related peptide (Cgrp) promoter. Cgrp-expressing cells have been demonstrated to be the predominant cell of origin in Rb1$^{fl/fl}$Trp53$^{fl/fl}$ (RP) mouse models of SCLC (Sutherland et al., 2011). As a comparison, Rb1$^{fl/fl}$Trp53$^{fl/fl}$Pten$^{fl/fl}$ (RPP) animals were infected with Cgrp-Cre viruses, which develop SCLC within 5-8 months (Cui et al., 2014; Gazdar et al., 2015; McFadden et al., 2014). Within five weeks of viral infection, some RPM mice began to exhibit labored breathing, which necessitated sacrifice. RPM mice had significantly increased mortality compared to RPP mice (median survival of 60 days vs. 164 days, respectively) (FIG. 1A). Compared to RPM mice, heterozygous RPM$^{LSL/+}$ mice had a slightly longer median survival of 81 days (FIG. 8B). As the RPM mice carry a luciferase allele, animals were monitored using bioluminescent imaging and the majority (n=8 of 11) exhibited a signal in the chest area without obvious signs of metastases (FIG. 1B). Upon sacrifice, lungs were dissected and large tumors were found in the upper central airway, usually involving the main bronchi (FIG. 1C).

Figure 1I:
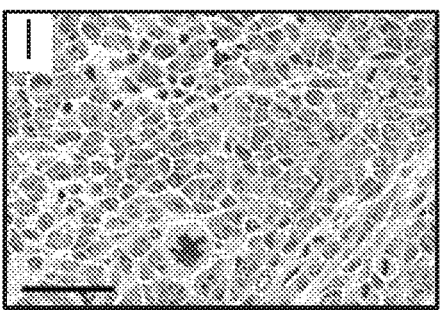
Figures 8E, 8F:
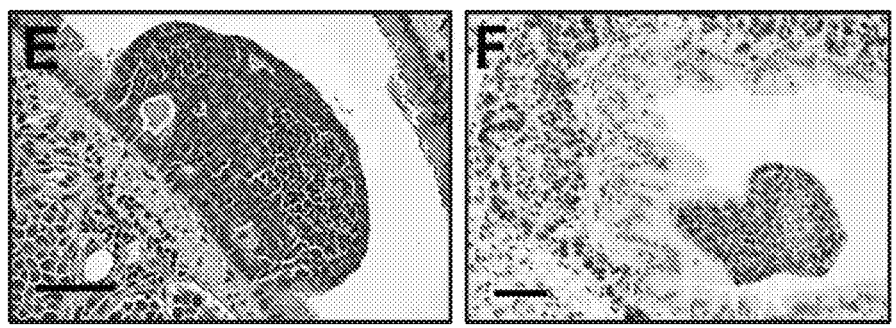
FIG. 8F shows Ki-67 immunocytochemistry (IHC) from 3-week tumor; scale bar is 50 µm.

A separate cohort of RPM mice were imaged between 5-7 weeks post Cgrp-Cre infection using low dose micro-computed tomography (microCT) imaging. In contrast to adenocarcinomas that develop in the distal and peripheral lung (Jackson et al., 2001; Oliver et al., 2010), RPM tumors were centrally located, exhibiting a donut-like pattern of density at major bronchi and large bronchioles (FIGS. 1D and 1E). To visualize tumors at earlier stages of development, a cohort of mice were sacrificed at 1-4 weeks post-infection (FIGS. 1F and 8C-F). Small proliferating (Ki67+) lesions were evident in or around the airways as early as 2-3 weeks (FIG. 8F). By 5-6 weeks post-infection, lung tumors exhibited massive lymphatic invasion and perivascular and peribronchial spread (FIG. 1G). Three board-certified pathologists (AFG, BLW, MES) classified all tumors as SCLC. While the overall appearances were consistent with human SCLC, tumors appeared to contain two populations of cells with distinct morphologies. One population had the features of typical "classic" SCLC, with small cells, scant ill-defined cytoplasm, finely granular nuclear chromatin and inconspicuous nucleoli (Travis, 2012) (FIG. 1H). The other population consisted of slightly larger cells with single, centrally located prominent nucleoli and well-defined eosinophilic cytoplasm, similar to what has been described as the variant form of SCLC (Gazdar et al., 1985) (FIG. 1I). Individual tumors consisted of one of these forms or a mixture of both. A recent review on the pathology of murine neuroendocrine lung cancers failed to identify the variant form in these models (Gazdar et al., 2015). Of interest, LCNEC or NSCLC tumor components were not noted in RPM animals, although they have been described in other GEMMs (Gazdar et al., 2015).

Figure 1J:
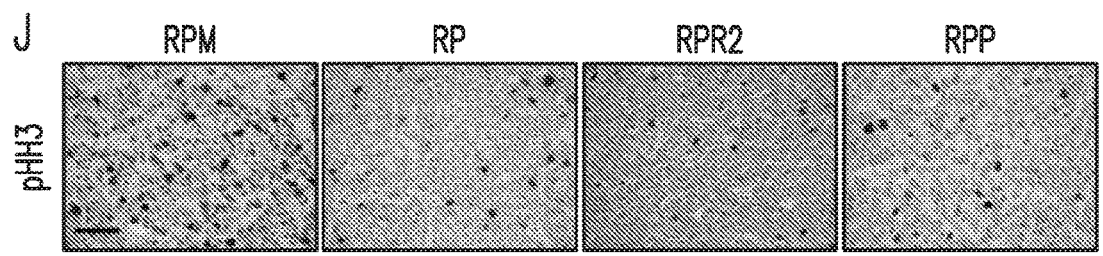
Figure 1L:
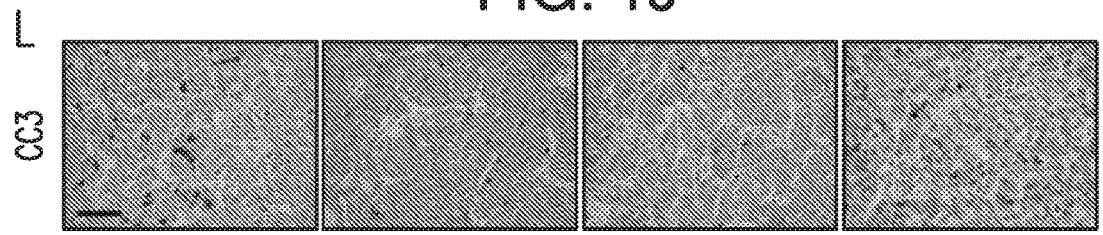
Figure 1K:
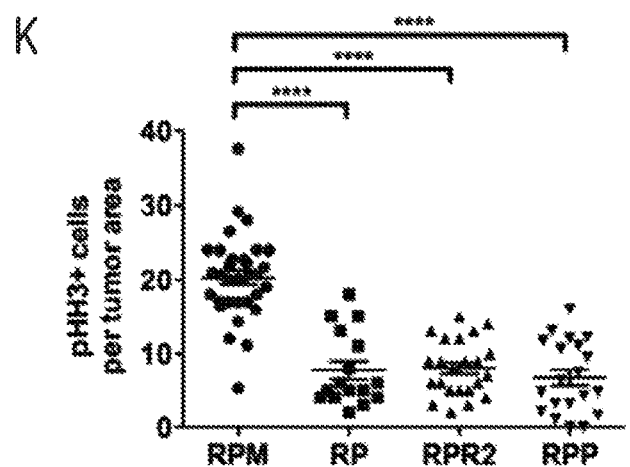
Figure 1M:
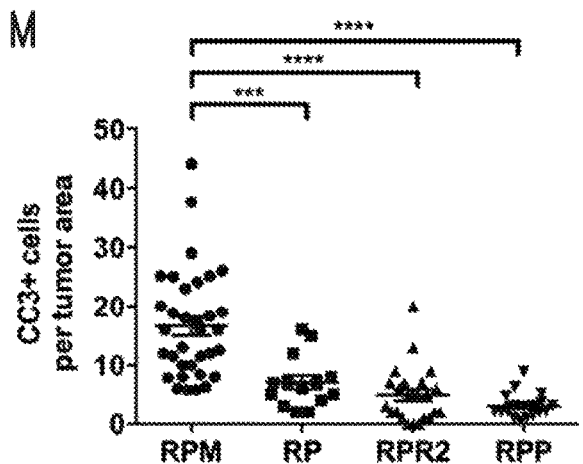
Figure 8G:
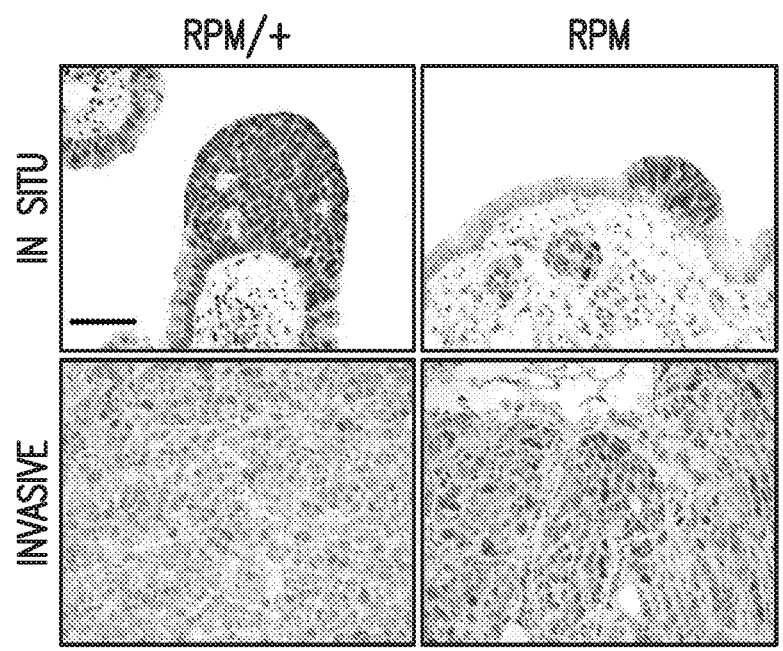
FIG. 8G is a representative MYC IHC at indicated stages of tumor development. Scale bar is 50 µm.
Figure 8H:
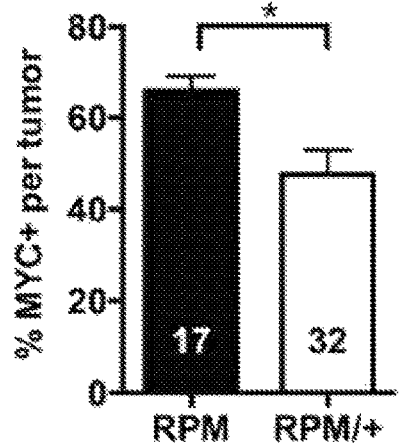
FIG. 8H shows quantification of MYC IHC from indicated genotypes. * p=0.0224.
Figure 8I:
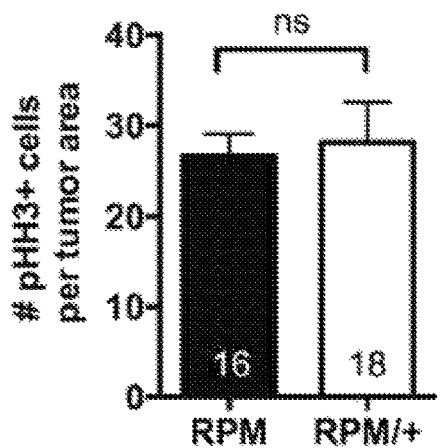
FIG. 8I shows quantification of pHH3 IHC in indicated mice.
Figure 8J:
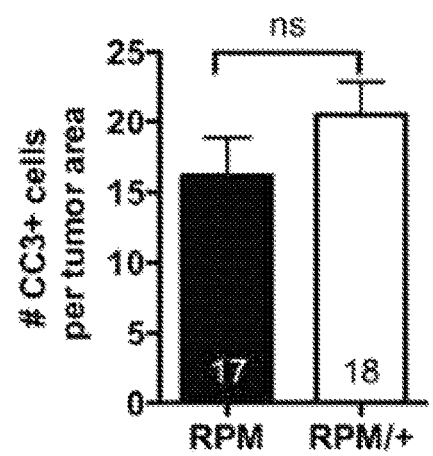
FIG. 8J shows quantification of CC3 IHC in indicated mice. Number of tumors analyzed indicated in bar graph for H-J.
Figure 8K:
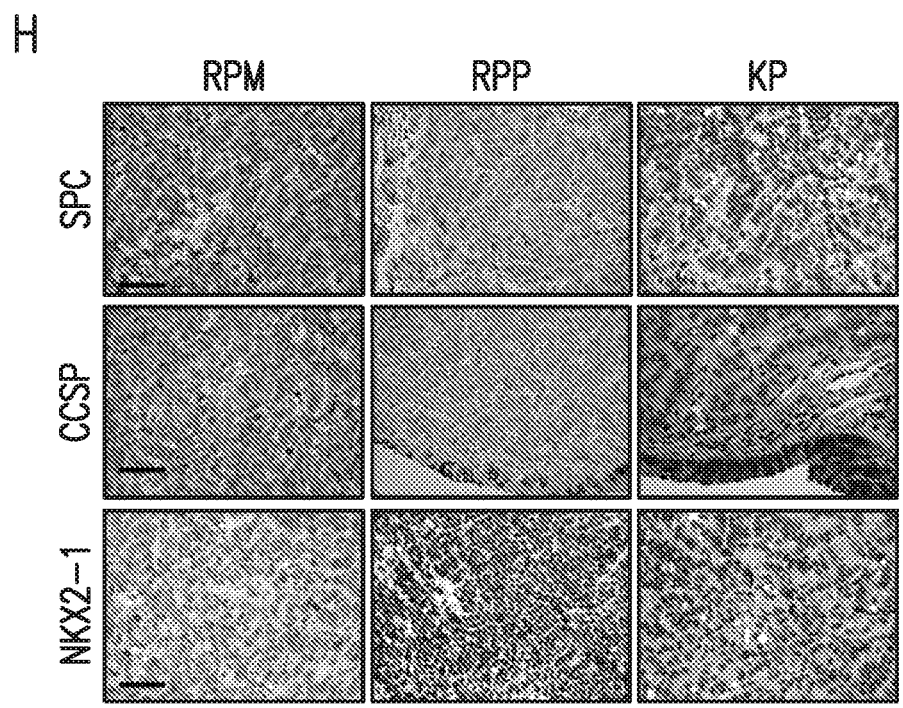
Figure 8L:
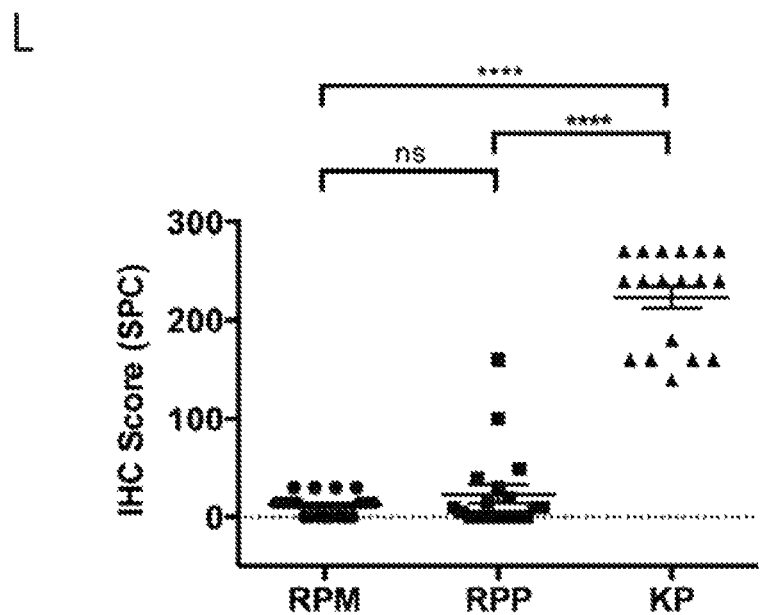
Figure 8M:
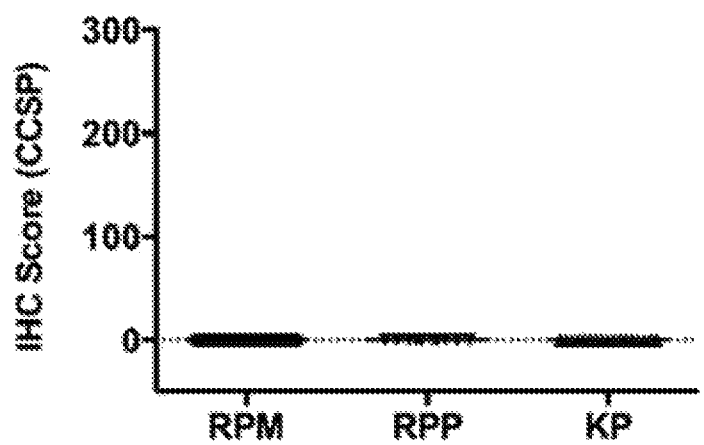
Figure 8N:
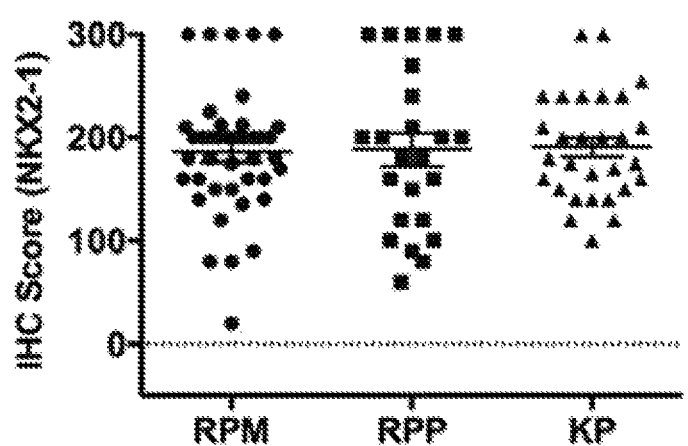

Because human SCLC can be highly proliferative and apoptotic (Travis, 2012), cell proliferation and apoptosis in RPM tumors were examined at 6-8 weeks post-infection. Consistent with their rapid development, RPM tumors had significantly higher levels of proliferation as measured by phospho-histone H3 (pHH3) levels compared to RP, Rb1$^{fl/fl}$Trp53$^{fl/fl}$Rbl2$^{fl/fl}$ (RPR2) and RPP tumors (FIGS. 1J and 1K). In the absence of any treatment, RPM tumors exhibited areas of necrosis; the Azzopardi phenomenon was not observed as noted in other GEMMS (Gazdar et al., 2015). RPM tumors exhibited significantly more apoptotic cells than other SCLC models as measured by immunohistochemistry (IHC) for cleaved caspase-3 (CC3) (FIGS. 1L and 1M). Compared to homozygous RPM tumors, RPM$^{LSL/+}$ tumors displayed subtly reduced levels of MYC (FIGS. 8G and 8H) but did not have statistically different levels of pHH3 or CC3 (FIGS. 8I and 8J). RPM tumors were uniformly negative for alveolar (i.e. SFTPC/SPC) and club cell (i.e. SCGB1A1/CCSP) markers (FIGS. 8K-M). NKX2-1, also known as TTF1, is expressed in the vast majority of adenocarcinomas and SCLCs and RPM RPP and LSL-Kras$^{G12D/+}$;p53$^{fl/fl}$ (KP) tumors expressed nuclear NKX2-1 as expected (FIGS. 8K and 8N). These data demonstrate that Myc accelerates tumor formation predominantly exhibiting variant histopathology.

Mice. Mice were housed in an environmentally controlled room. p53$^{fl/fl}$ mice were generated by A. Berns (Meuwissen et al., 2003) and p53$^{fl/fl}$Rb1$^{fl/fl}$ mice were provided by T. Jacks (Sage et al., 2000). Rb1$^{fl/fl}$Trp53$^{fl/fl}$Pten$^{fl/fl}$ mice were provided by D. MacPherson (Cui et al., 2014). At 6-8 weeks of age, anesthetized mice were infected with $10^7$ or $10^8$ plaque-forming units of Ad5-Cgrp-Cre viruses (University of Iowa) by intratracheal instillation as described elsewhere (Jackson et al., 2001). Viruses were administered in a Biosafety Level 2+ room according to Institutional Biosafety Committee guidelines. Both male and female mice were equally divided between treatment groups for all experiments.

The Myc transgenic mouse was generated by inserting the attB-CAG-loxP-Stop-loxP-MycT58A-IRES-Luciferase-WPRE-pA cassette (transgene cassette) into the H11 locus on chromosome 11 using integrase-mediated TARGATT technology by Applied Stemcell Inc. The transgene cassette was inserted site-specifically at the H11 locus mediated by φC31 integrase. For generation of LSL-MycT58A mice, homozygous H11 P3 mice (FVB strain) were used as embryo donors. A mix of transgene plasmid DNA and φC31 mRNA were microinjected into 107 H11 P3 zygotes and implanted into four CD1 recipient mothers. One positive founder was identified and used in all subsequent experiments. Intercrossed RPM mice were maintained on a mixed background strain consisting of 129/Ola, 129/Sv and C57B6/FVB. Genotyping of LSL-MycT58A mice was performed using the following primer sequences: Myc-F 5'-AACTTCCCGCCGCCGTTGTT-3'(SEQ ID NO: 1), Myc-R 5'-CAACGGGCCACAACTCCTCA-3'(SEQ ID NO: 2), H11-WT-F 5'-TGGAGGAGGACAAACTGGT-CAC-3'(SEQ ID NO: 3) and H11-WT-R 5'-TTCCCTTTCTGCTTCATCTTGC-3' (SEQ ID NO: 4). Myc transgene product is ~420 bp, and the H11 wild type product is ~321 bp.

Mice were given freshly prepared cisplatin (Sigma, St. Louis, Mo., USA) in PBS on Day 1, etoposide (in 70% PEG in water, Sigma, St Louis, Mo., USA) on Day 2 or PBS by intraperitoneal (i.p.) injection. Alisertib (MLN8237, ApexBio, dissolved in 10% 2-hydroxy-beta-cyclo-dextrin and 1% sodium bicarbonate) was given 20 mg/kg twice daily by oral gavage on a schedule of 5 days on, 2 days off. For BrdU labeling experiments, BrdU (Sigma) was injected i.p. (30 mg/kg in PBS) 24 hr before sacrifice. For survival studies, endpoints include but are not limited to: difficulty breathing, eating or moving, obvious signs of pain or weight loss greater than 20% of initial body weight. Mice in the survival studies were sacrificed as a result of primary lung tumor burden or toxicity, but no animals were sacrificed due to distant metastatic disease.

MicroCT and Bioluminescent Imaging. Mice were scanned for 34 sec under isoflurane anesthesia using a small animal Quantum FX microCT (PerkinElmer) at 45 µm resolution, 90 kV with 160 µA current. Images were acquired using PerkinElmer Quantum FX software and processed with Analyze 11.0 (AnalyzeDirect). For bioluminescent imaging, mice were shaved and given 150 mg/kg D-luciferin potassium salt (Regis Technologies) i.p. and imaged on a Xenogen IVIS Spectrum instrument (PerkinElmer).

Scans were calibrated for Hounsfield Units (HU) by determining the mean value of "Bed" and "Air" for representative scans through the region of interest (ROI) tool and matching those values to their known HU (40 HU and −1000 HU, respectively) using the "Image Algebra" tool. Every image was then applied a 3×3×3 Median Filter from the "Spatial Filters" window. Thresholds of "Air" vs. "Dense Tissue" were established using the ROI and histogram tools. Every image was processed and normalized using the "Image Algebra" tool, followed by a 3×3×3 Median Filter from the "Spatial Filters" window. For Total Tumor Burden Analyses, the object map was created using the previously established thresholds; adjustments were made manually using "Spline Edit", "Draw" and "Nudge Edit" tools. The object map was then morphed using the "Morphology" tool. The object map was made binary by using the threshold morphing tool. Then, the map was dilated 3 times using 5×5×5 Jack-shaped structuring elements. The holes were then filled on every 2D-orientation. The map was finally brought back to its original size using the "Erode" tool 3 times using 5×5×5 Jack-shaped structuring elements. The volumetric analyses were then performed in the ROI window using the pre-established thresholds and non-airspace was calculated using the formula: Non-airspace=1−(VolAir/ROIVol). For individual tumors, the 3D segmentation was performed semiautomatically using Analyze 11.0 "object extract tool". Adjustments were made manually using the "Spline Edit", "Draw" and "Nudge Edit" tools. The tumor segmentation was then processed using the semi-automatic tools "fill holes" and the object was propagated and smoothed in the axial, transverse and coronal planes. Volume quantification was obtained using the ROI tool as for total tumor burden analyses.

Immunohistochemistry. Lungs were inflated with PBS or formalin, fixed overnight in neutral buffered formalin, and transferred to 70% ethanol. Paraffin embedded lung lobes were sectioned at 4 µm and stained with H&E for tumor pathology or with antibodies as described previously (Mukhopadhyay et al., 2014).

Sections were dewaxed, rehydrated and subjected to high temperature antigen retrieval, 20 min boiling in a pressure cooker in 0.01 M citrate buffer, pH 6.0. Slides were blocked in 3% H2O2 for 15 min, blocked in 5% goat serum in PBS/0.1% Tween-20 (PBS-T) for 1 hr, and stained overnight in blocking buffer with primary antibodies. A HRP conjugated secondary antibody (Vector Laboratories) was used at 1:200 dilution in PBS-T, incubated for 45 min at room temperature, followed by DAB staining (Vector Laboratories). All staining was performed with Sequenza coverplate technology. Mouse on Mouse (M.O.M.) Basic Kit (Vector Laboratories) was used for staining with BrdU and Ki67 mouse primary antibodies. Tris buffered saline with Tween-20 (TBS-T) was used instead of PBS-T for phospho-protein antibodies. The primary antibodies include: Myc (Santa Cruz sc-764) 1:150; SPC (Millipore AB3786) 1:2000; CCSP (Millipore 07-623) 1:2000; NKX2-1 (Abcam ab76013) 1:250; UCHL1 (Sigma HPA005993) 1:250; BrdU (BD Biosciences 347580) 1:200; Ki-67 (BD Pharmingen #556003) 1:300; phospho-Histone H3 (Ser10) (Cell Signaling Technology #9701) 1:100; cleaved-Caspase3 (Asp175) (Cell Signaling Technology #9661) 1:300; phospho-H2AX (Ser139) (Cell Signaling Technology #9718) 1:120; CGRP (Sigma C8198) 1:250; ASCL1 (BD Pharmingen 556604) 1:100; NEUROD1 (Abcam ab109224) 1:150; NCAM1 (Chemicon International AB5032) 1:200; NFIB (Sigma HPA003956) 1:250.

Immunocytochemistry (IHC) analysis was performed either manually using digital images of stained tissues captured by Zeiss Axio Scope.A1 microscope and analyzed using AxioVision SE64 software or by automated methods using Aperio Technologies Scanscope software. In both cases, whole slides containing 3-5 lung lobes per animal were analyzed. For manual quantification, IHC Score (S) was calculated by multiplying the percentage of positive cells (P; 0-100%) by the intensity (I; 0-3). Formula: S=P×I; Range=0-300.

For automated image analysis, IHC-stained slides were digitally scanned with the Aperio AT2 Scanscope and whole slides images were quantitatively analyzed with image analysis nuclear algorithm using Halo digital imaging analysis software (Indica Labs, NM, USA). Tumor regions were manually annotated and image analysis algorithms were applied only to tumor regions. The nuclear algorithm applied distinguishes cells based on the expression profiles as positive and negative as well as intensity. Results are expressed as percent positive cells per tumor area. Tumor burden was calculated by dividing the total tumor area by the total lung area from all lung sections and converting the results to percentage values ("tumor burden").

For quantification of liver and lymph node metastases, we took four step sections (100 microns apart) from H&E stained tissue and quantified the number of animals with obvious metastases.

Statistical Analyses. GraphPad Prism was used to perform statistical analyses. Survival analyses were analyzed using log-rank (Mantel-Cox) test. Error bars represent mean+/−SEM unless otherwise indicated. For the statistical analysis of the IHC stains or tumor burden, column analysis was performed by Student's unpaired t test with p-value <0.05 considered statistically significant. For box-and-whisker plots, boxes show 25th, median and 75th quantile; whiskers extend to 1.5× interquartile range above/below the highest/lowest quartiles.

Example 2: MYC Promotes Neuroendocrine-Low SCLC with NEUROD1 Expression

Figure 9A:
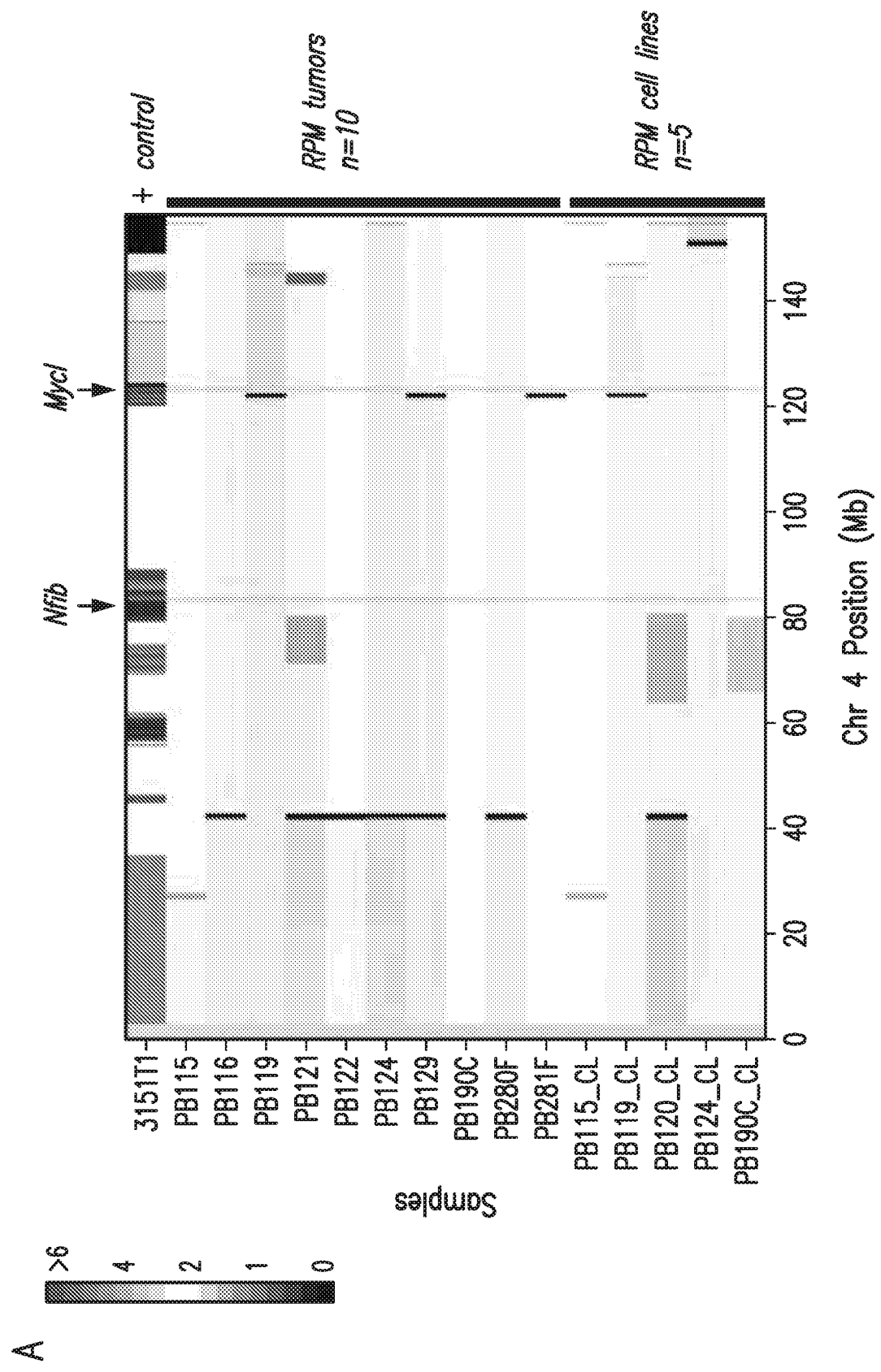
FIGS. 9A-C show MYC promotes neuroendocrine-low SCLC with high NEUROD1 expression.
Figure 9B:
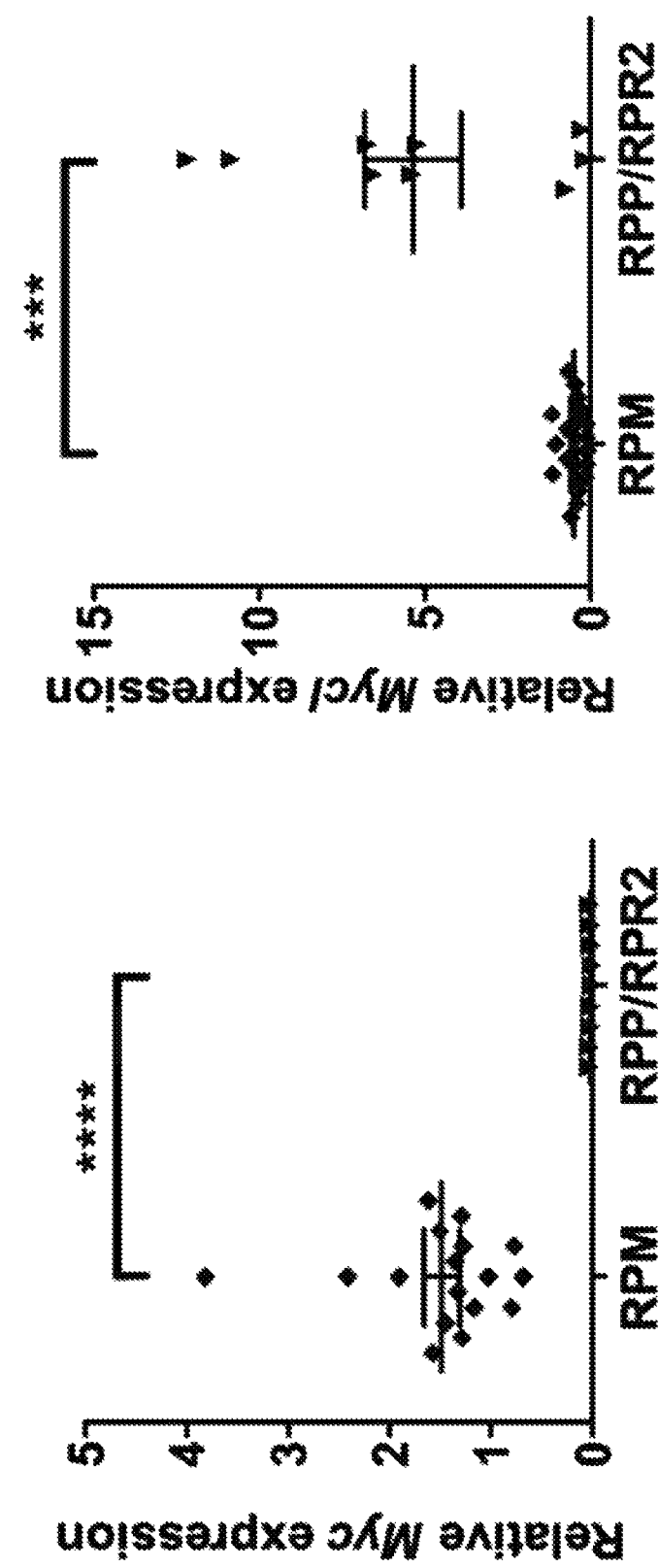

Neuroendocrine differentiation is considered a hallmark of classic SCLC. Previous mouse models recapitulate the classic phenotype and are frequently associated with Mycl-amplifications (Calbo et al., 2011). In contrast, variant SCLC was previously reported to express low levels of neuroendocrine markers (Carney et al., 1985). Interestingly, RPM tumors recapitulate variant SCLC morphology and lack Mycl amplifications (FIG. 9A). RPM tumors expressed significantly more Myc and less Mycl than tumors from RPP and RPR2 models (FIG. 9B).

Figure 2A:
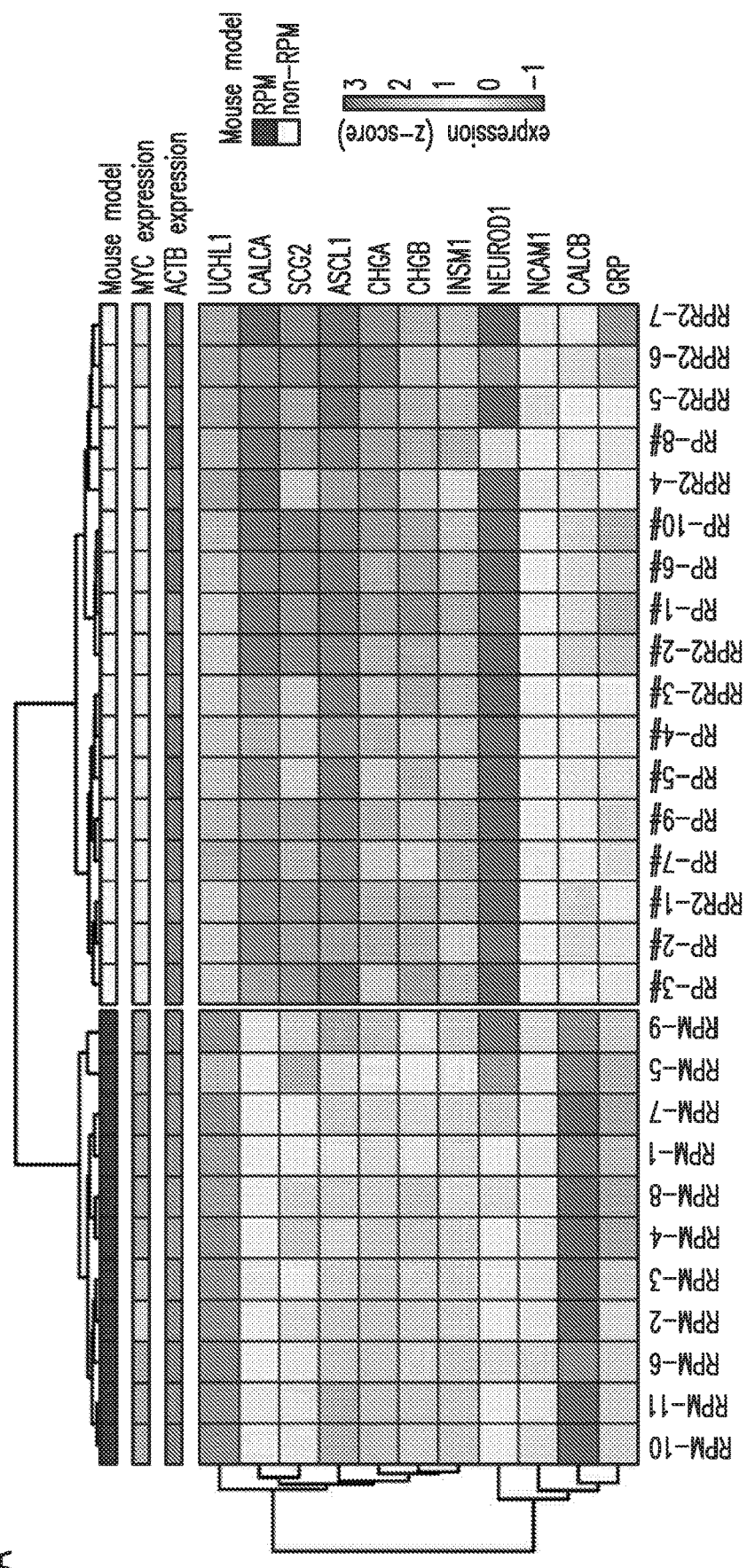
FIGS. 2A-E show that MYC promotes neuroendocrine-low small cell lung cancer (SCLC) with NEUROD1 expression in vivo.
Figure 2B:
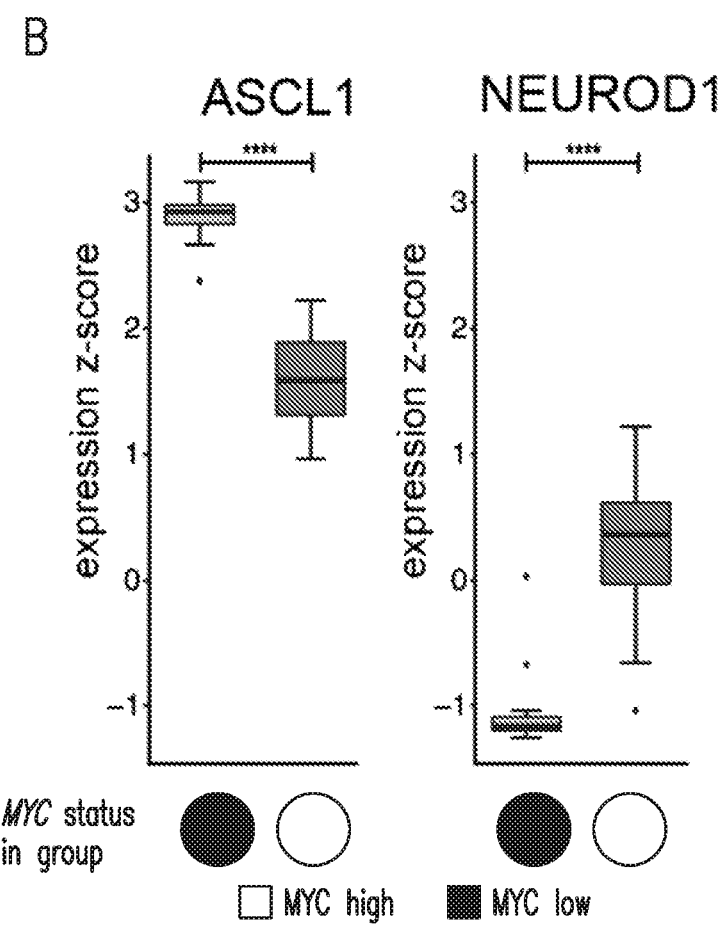
Figure 2C:
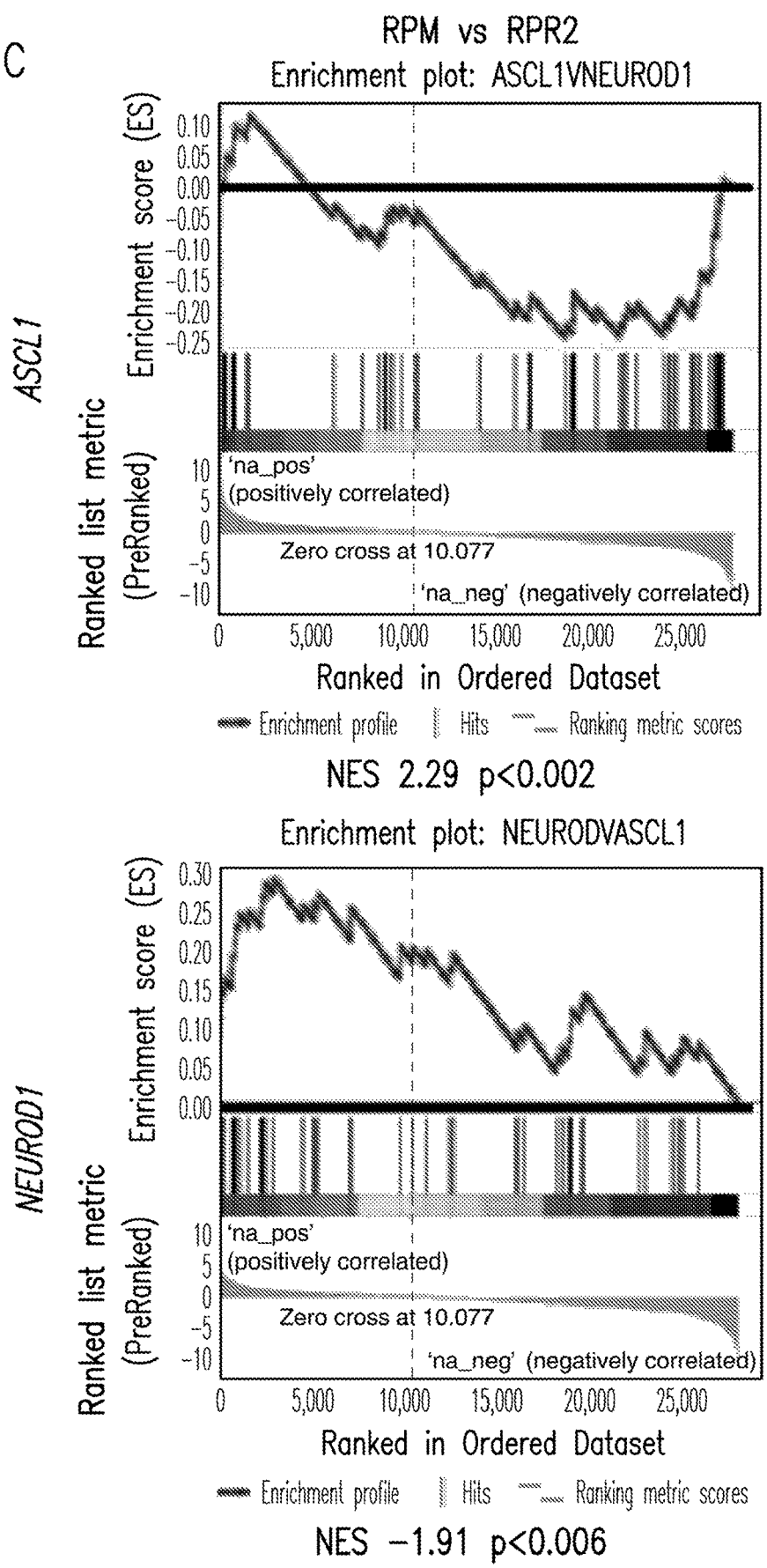

To determine whether MYC is associated with attenuation of neuroendocrine differentiation in vivo, hierarchical clustering analyses was performed for neuroendocrine markers that overlapped between published microarray data derived from RP (n=10) and RPR2 tumors (n=3) (Schaffer et al., 2010), as well as RNA-seq data that was generated for additional RPR2 tumors (n=4) and RPM tumors (n=11) (FIG. 2A). RPM tumors clustered independently from RP and RPR2 tumors and exhibited lower expression of the majority of neuroendocrine genes. Interestingly, RPM tumors had significantly reduced expression of the neurogenic transcription factor Ascl1 but high expression of NeuroD1 (FIG. 2B). Previous studies described distinct tumorigenic functions of ASCL1 and NEUROD1 in SCLC (Borromeo et al., 2016; Poirier et al., 2013; Poirier et al., 2015) and the association between high MYC expression and neuroendocrine differentiation was explored in the SCLC model described herein. First, the mouse tumor RNA-seq data was analyzed using Gene Set Enrichment Analysis (GSEA). NEUROD1$^{high}$ signature was found to be significantly enriched and an ASCL1$^{high}$ signature was significantly depleted in RPM tumors compared to RPR2 tumors (FIG. 2C).

Figure 2D:
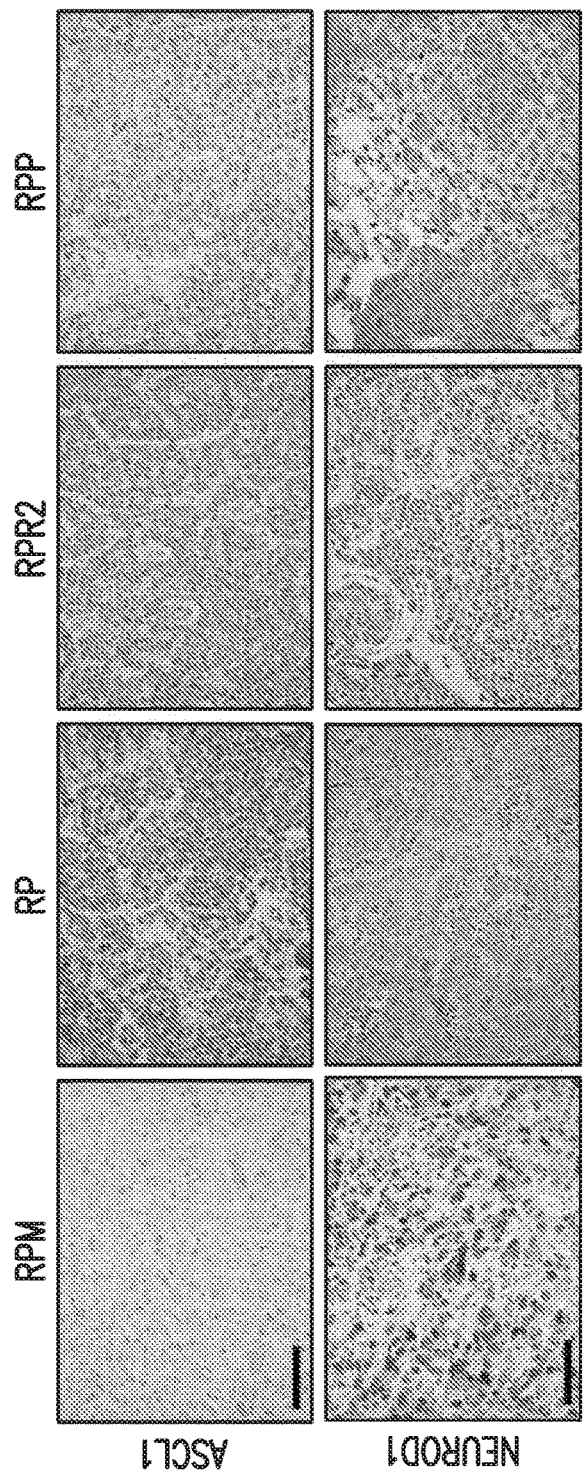
Figure 2D:
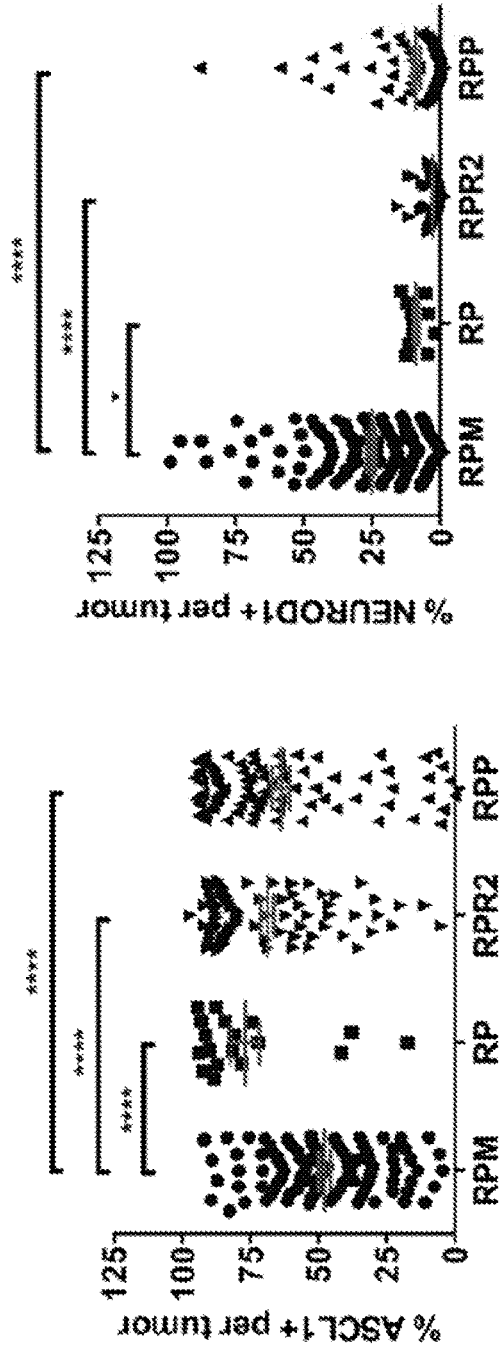
Figure 9C:
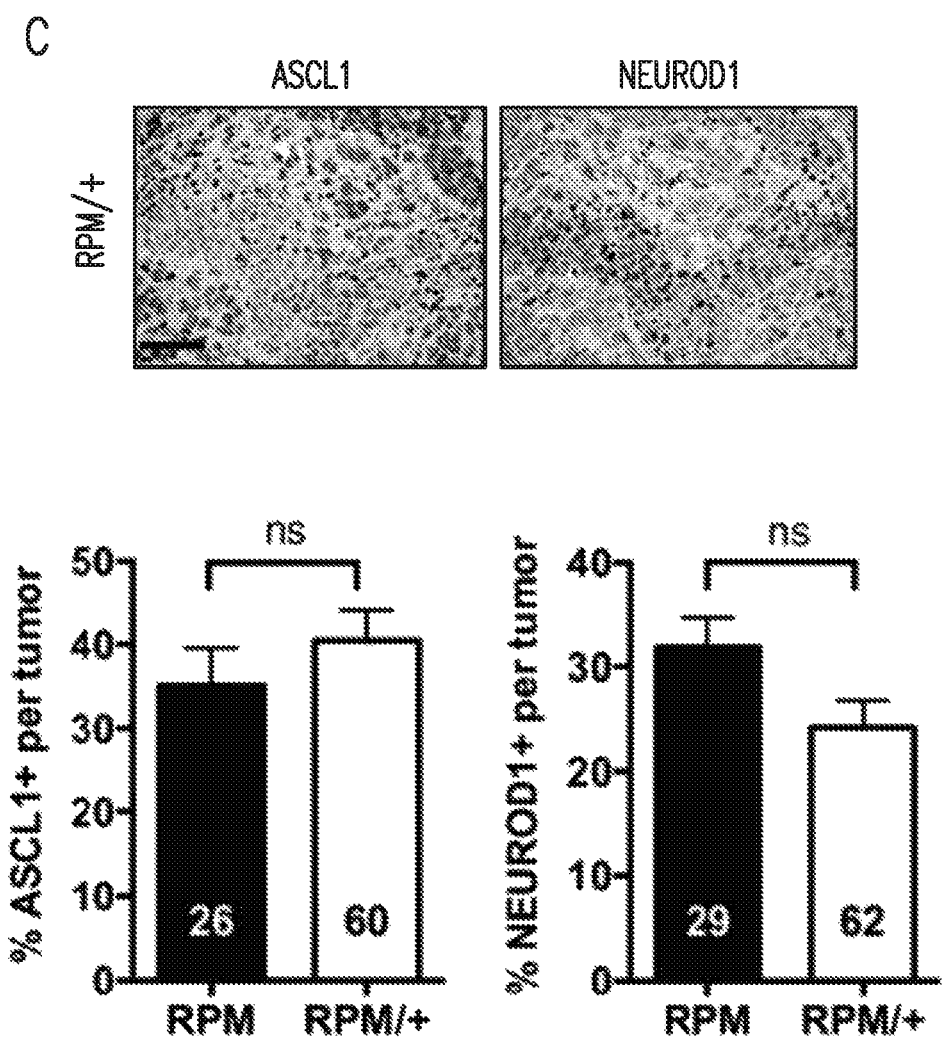

Next, protein expression of ASCL1 and NEUROD1 in multiple GEMMS was examined by IHC. All SCLC models harbored ASCL1+ lung tumors, but the levels of ASCL1 were significantly lower in RPM tumors compared to RP, RPR2 and RPP models (FIG. 2D). In contrast, RPM tumors demonstrated high and heterogeneous expression of NEUROD1 compared to classic GEMMs, which was rarely detected in RPP tumors (FIG. 2D). Compared to homozygous RPM tumors, RPM$^{LSL/+}$ tumors had a trend towards higher ASCL1 and lower NEUROD1 expression (FIG. 9C).

Figure 2E:
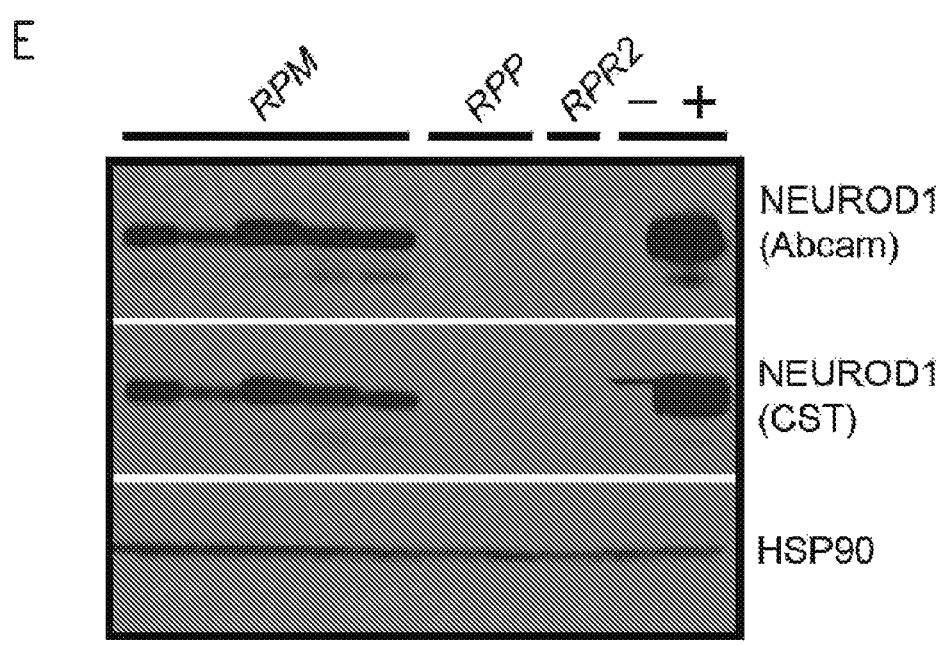

RPM tumors were confirmed to express NEUROD1 using two independent antibodies including that used for IHC (FIG. 2E). Together these data suggest that MYC promotes a variant, neuroendocrine-low, NEUROD1+ subset of SCLC.

Over 30 years ago, human SCLC cell lines with variant morphology were found to exhibit frequent MYC amplifications (Carney et al., 1985; Gazdar et al., 1985). The data described herein show that MYC drives the variant histopathology in vivo, a subset of tumors that has not been previously observed in mouse models (Gazdar et al., 2015), suggesting this is likely because Mycl is the oncogenic driver in other GEMMs (Calbo et al., 2011; Dooley et al., 2011), whereas in the model described herein, Myc serves this function. Importantly, the data disclosed herein demonstrate that MYC promotes a neuroendocrine-low phenotype associated with high expression of NEUROD1. NEUROD1 expression was initially found to correlate with the variant subtype of cell lines (Poirier et al., 2013), and was subsequently found to stratify a subset of ASCL1$^{low}$ primary human SCLCs in multiple studies (Borromeo et al., 2016; Poirier et al., 2015). In addition, NEUROD1 is present along with MYC at super-enhancers in MYC-high cell lines (Borromeo et al., 2016; Christensen et al., 2014). Thus far, it appears that normal mouse neuroendocrine cells do not express NeuroD1, so it has been questioned whether NEUROD1-expressing human tumors actually arise in the lung or metastasize from elsewhere in the body (Borromeo et al., 2016; Bunn et al., 2016). The data described herein show that murine Myc-driven SCLCs do indeed express NEUROD1 and have a significantly higher NeuroD1 signature than other GEMMS, suggesting that their human counterparts arise in the lung. Based on in situ immunostaining patterns for ASCL1 and NEUROD1, it was postulated that MYC-driven tumor cells arise in ASCL1+ precursors, and these early tumor cells initially exhibit classic morphology. With time, it appears that tumors switch to an ASCL1$^{Low}$/NEUROD1$^{High}$ state coincident with the appearance of variant morphology and low neuroendocrine phenotype. Since overexpression of NEUROD1 has been linked to the development of metastases and aggressive SCLC (Osborne et al., 2013), the data presented herein suggest that MYC activation could fuel this phenotype via NEUROD1 signaling. Further, the data described herein suggest MYC's role in NEUROD1 regulation may be indirect given the absence of NEUROD1 expression in in situ lesions that are MYC+. These data have important clinical implications given the recent development of neuroendocrine gene targeted therapies such as the DLL3-antibody drug conjugate (Saunders et al., 2015). The results disclosed herein predict that MYC-driven SCLCs with lower neuroendocrine gene expression may be relatively less responsive to some neuroendocrine-targeted therapies.

Immunoblot. For primary lung tumor lysates, mouse lung tumors were micro-dissected under sterile conditions, flash frozen and stored at −80° C. until use. Approximately 20-40 mg tumor pieces were disrupted and lysed to homogeneity with disposable pestles and cordless motor (VWR) in 200 μl RIPA buffer supplemented with protease inhibitors (Roche complete mini) and sodium orthovanadate (Sigma). Lysates are centrifuged at 13000 rpm for 15 minutes and supernatants are transferred to new tubes. For cell line lysates, total protein lysates are prepared as previously described, separated via SDS-PAGE and transferred to a PVDF membrane (Oliver et al., 2011). Membranes were blocked for 1 hr in 5% milk or 5% BSA, followed by overnight incubation with primary antibodies at 4° C. Membranes were washed for 6×5 min at room temperature in TBS-T. Mouse and rabbit HRP-conjugated secondary antibodies (Jackson ImmunoResearch, 1:10,000) were incubated for 1 hr at room temperature followed by washing 6×5 min at room temperature in TBS-T. For detection, membranes were exposed to WesternBright HRP Quantum substrate (Advansta) and detected on Hyblot CL film (Denville Scientific Inc). Primary antibodies include: c-Myc (Cell Signaling #13987, 1:1000), phospho-Aurora kinases pan (Cell Signaling #2914, 1:1000), Aurora kinase A (ThermoFisher #45-8900, 1:500), Aurora kinase B (Cell Signaling #3094, 1:1000), phospho-histone H3 (Cell Signaling #9701, 1:1000), cleaved-Caspase-3 (Cell Signaling #9661, 1:1000), Synaptophysin (Thermo Scientific #RB-1461-P1, 1:200), Rb1 (Cell Signaling #9313, 1:1000), p53 (Santa Cruz #sc-6243, 1:1000), Actin (Sigma #A2066, 1:10000), Hsp90 (Cell Signaling #4877, 1:1000), NEUROD1 (Abcam ab109224, 1:1000), NEUROD1 (Cell Signaling #4373, 1:1000).

Alternatively, cell lysates were prepared using RIPA buffer supplemented with protease inhibitors (Roche complete mini) and benzonase (Millipore)), separated on 4-20% Tris-glycine SDS-PAGE gels (Invitrogen), and transferred to PVDF-FL membrane (Millipore). Membranes were blocked using Li-Cor blocking buffer (1:10 in TBS) and incubated with primary antibodies in blocking solution with 0.2% Tween 20 overnight at 4° C. Prior to detection with a near-IR imaging system (Li-Cor Odyssey), membranes were washed in TBS-T, incubated with secondary antibodies and washed in TBS-T. For total Aurora A in FIG. 6H, the chemiluminescent signal (ECL, GE Healthcare) was captured with a CCD-camera (BioRad Geldoc XR+). Primary antibodies: c-Myc (Cell Signaling #9402, 1:1000), phospho-Aurora kinases pan (Cell Signaling #2914, 1:500), Aurora kinase A (Cell Signaling #3092, 1:1000), Aurora kinase A (Santa Cruz sc-14318, 1:1000), Aurora kinase B (BD Biosciences 611082, 1:1000), Hsp90 (Stressgen SPA-835, 1:5000), phospho histone H3 (S10, a kind gift by P. Eyers, Sheffield, rabbit polyclonal, 1:5000), Synaptophysin (Thermo RM9111-S, 1:1000). Secondary antibodies: goat anti-rabbit 800CW (Li-Cor Cat. 926-32211, 1:10000), goat anti-mouse 800CW (Li-Cor Cat. 926-3220, 1:10000), anti-rat 680 (Li-Cor Cat. 925-68029), anti-goat HRP-coupled antibodies.

Mouse copy number variation (CNV) genomic analyses. Individual primary lung tumors were excised and microdissected under sterile conditions with matched tail for normal DNA control. DNA for CNV analysis was isolated with DNeasy DNA isolation kit (Qiagen) and sheared with Covaris S2 Focused-ultrasonicator to generate ~350 bp DNA fragments. The Illumina TruSeq DNA PCR-Free Sample Preparation Kits (cat # FC-121-3001 and FC-121-3002) were used to make sequencing libraries. Illumina cBot was used for applying chemically denatured libraries (25 µM) to an Illumina HiSeq v4 paired end flow cell. Clonal amplification of hybridized molecules was performed with Illumina HiSeq PE Cluster Kit v4-cBot (PE-401-4001). 125-cycle paired-end sequence run was performed with HiSeq SBS Kit v4 sequencing reagents (FC-401-4003) in an Illumina HiSeq 2500 instrument (HCS v2.2.38 and RTA v1.18.61). Reads were aligned to mm10 using bwa mem (v0.7.10). Duplicate reads were identified using samblaster (v0.1.22) and removed. CNVs were called on chr4 using the CNVKit (v0.7.11) batch command using whole genome sequencing settings (Talevich et al., 2016). The CNV heatmap was generated using the CNVKit heatmap command on the predicted copy number regions.

Mouse tumor RNA-Seq. RNA isolation from primary tumors and healthy lungs was performed using RNeasy Mini Kit (Qiagen) with the standard protocol. RNA was subjected to library construction with the Illumina TruSeq Stranded mRNA Sample Preparation Kit (cat # RS-122-2101, RS-122-2102) according to manufacturer's protocol. Chemically denatured sequencing libraries (25 µM) are applied to an Illumina HiSeq v4 single read flow cell using an Illumina cBot. Hybridized molecules were clonally amplified and annealed to sequencing primers with reagents from an Illumina HiSeq SR Cluster Kit v4-cBot (GD-401-4001). Following transfer of the flowcell to an Illumina HiSeq 2500 instrument (HCSv2.2.38 and RTA v1.18.61), a 50 cycle single-read sequence run was performed using HiSeq SBS Kit v4 sequencing reagents (FC-401-4002). Mouse mm10 annotations (Ensembl build 82) were used in the RSEM (v1.2.12) utility rsem-prepare-reference to create bowtie (v1.0.1) indices. Gene expression was determined using the RSEM utility rsem-calculate-expression with the forward strand probability set to zero. Differential expression was determined using EBSeq (v1.4.0) using 'Median-Norm' function to calculate size factors and setting 'maxround' to 10. To adjust for transcript length, fragments per kilobase per million reads (FPKM) were calculated for all genes and log 2-transformed after addition of a small constant (0.01). Gene set enrichment analysis (GSEA) for murine SCLC tumors was performed on RNA-seq gene expression with ASCL1/NEUROD1 high/low gene sets (Borromeo et al., 2016; Subramanian et al., 2005). For a comparison of NE marker expression in RPM tumors (n=11) to other murine SCLC models, the GSE18534 dataset was downloaded from GEO (http://www.ncbi.nlm.nih.gov/geo/) containing expression array data of mouse Rb1/Trp53 (RP, n=10), Rb1/Trp53/Rbl2 (RPR2, n=3) primary tumors as described in (Schaffer et al., 2010). Log 2-transformed, normalized intensity values were obtained and were averaged across probes to obtain gene expression levels. To avoid systematic bias by expression methodology, RNA-Seq was also performed on four samples of the Schaffer et al. murine RPR2 tumor model as described above. For combined analysis, log 2-transformed FPKM and intensity values were converted to z-scores within samples and distributions were adjusted per gene by quantile normalization across samples. Subsequently clustering was performed on neuroendocrine (NE) markers with Euclidean distance and Ward clustering metric. Results were annotated with beta Actin (ACTS) expression as reference gene.

Human genomics. RNA-seq data for human patient samples and cell lines were obtained from published literature (George et al., 2015; Peifer et al., 2012; Rudin et al., 2012) and newly generated datasets with gene expression quantified as fragments per kilobase per million reads (FPKM) and analyses performed on log 2(FPKM+1).

Transcriptome sequencing data of human primary SCLC tumor samples (n=81) and human SCLC cell lines (n=34) were studied. RNA-seq data on human primary tumors was obtained from earlier studies (George et al., 2015; Peifer et al., 2012); the study on human cell lines included previously published cases (n=19, (Rudin et al., 2012) and n=1 from (Peifer et al., 2012)) and we additionally performed RNA-seq on 14 SCLC cell lines. In brief, SCLC cell lines were harvested at subconfluency and RNA was extracted with the RNAeasy Mini Kit (Qiagen) following the instructions of the manufacturer. After preparation of cDNA libraries from poly(A) selected RNA, the Illumina TruSeq protocol for mRNA was used to generate sequencing libraries. Sequencing was performed with a 2×100 bp paired-end protocol on an Illumina HiSeq 2000 (Illumina, San Diego). RNA-seq data was analyzed as previously described (Fernandez- Cuesta et al., 2015; George et al., 2015). The raw paired-end sequencing reads were aligned to the NCBI37/hg19 human reference genome using GSNAP (Wu and Nacu, 2010) and expression was quantified with Cufflinks (Trapnell et al., 2010) as FPKM (fragments per kilobase of exon per million fragments mapped). Gene expression was inferred from the most abundant transcript per gene in patients. Since FPKM values approximately follow a log-normal distribution they were transformed to log 2(FPKM+1) for further processing.

Due to the relatively low prevalence of genomic MYC-amplifications in the SCLC patient samples (George et al., 2015), but a considerable number of patients with high MYC FPKM values, MYC-expression was used for patient stratification by fitting a Gaussian mixture model to the bimodal distribution of MYC-expression levels (Benaglia et al., 2009). The log 2-FPKM cut-off to classify patients as MYC-high or MYC-low was chosen based on the overlapping normal distributions at the threshold where the probability for an FPKM value being drawn from either distribution was equally likely. To insure consistency the same cut-off value was used to classify cell lines as MYC-high or MYC-low independent of copy-number status. For GSEA genes were ranked by fold-difference based on the averages of the MYC-high/MYC-low patients. Unsupervised hierarchical clustering was done using Euclidean distance and Ward's clustering metric (Ward, 1963). Analyses were performed in R statistical environment (Team, 2014).

For validation, data was additionally obtained for 65 human SCLC cell lines recently generated on Affymetrix Exon microarrays (Polley et al., 2016) from http://sclccell-lines.cancer.gov (accessed 2016 Aug. 13). Twenty-five cell lines were shared between the Cologne/Rudin et al. and the Polley cell line panels. Classification of cell lines as MYC-high or MYC-low in the Polley panel was performed as described in "Bioinformatic analyses of published drug screen." Prior to clustering analysis gene expression was converted to z-scores. Non-SCLC cell lines and cell lines derived from NCI-H69 (NCI-H69/CPR, NCI-H69/LX10 and NCI-H69VCR/R) were not included in this analysis.

Cell counting. The cell number per well was determined using a Z2 Coulter particle counter (Beckman Coulter) and normalized to the average cell number of the control (shGFP or untreated) for each cell line and experimental replicate. Graphs display average relative cell numbers with standard deviation unless indicated otherwise. For the combination treatment in FIG. S6D cells were treated for 96 hours with or without 10 nM alisertib and 0.1 µM cisplatin or etoposide prior to counting.

Quantitative RT-PCR for mouse tumors. RNA was isolated from macro-dissected tumors using RNeasy Mini Kit (Qiagen). A total of 1 µg RNA was converted to cDNA using iScript cDNA synthesis kit (Bio-Rad). Real-time RT-PCR was performed with SYBR Green Supermix (Bio-Rad) in triplicate on a Bio-Rad CFX96 Real-Time PCR machine. Expression values were based on 10-fold serial dilutions of standards and normalized to Actin levels. Mycl forward primer: ACGGCACTCCTAGTCTGGAA (SEQ ID NO: 21), Mycl reverse primer CCACGTCAATCTCTTCACCTT (SEQ ID NO: 22); Myc forward primer: CCTAGTGCTG-CATGAGGAGA (SEQ ID NO: 23), Myc reverse primer: TCTTCCTCATCTTCTTGCTCTTC (SEQ ID NO: 24) obtained from (Kim et al., 2016). Actin forward primer: GGCATAGAGGTCTTTACGGATGTC (SEQ ID NO: 25), Actin reverse primer: TATTGGCAACGAGCGGTTCC (SEQ ID NO: 26).

Methods and materials used are described herein and above.

Example 3: RPM Tumors Recapitulate Molecular Subset of MYC-High Human SCLC

Figure 3A:
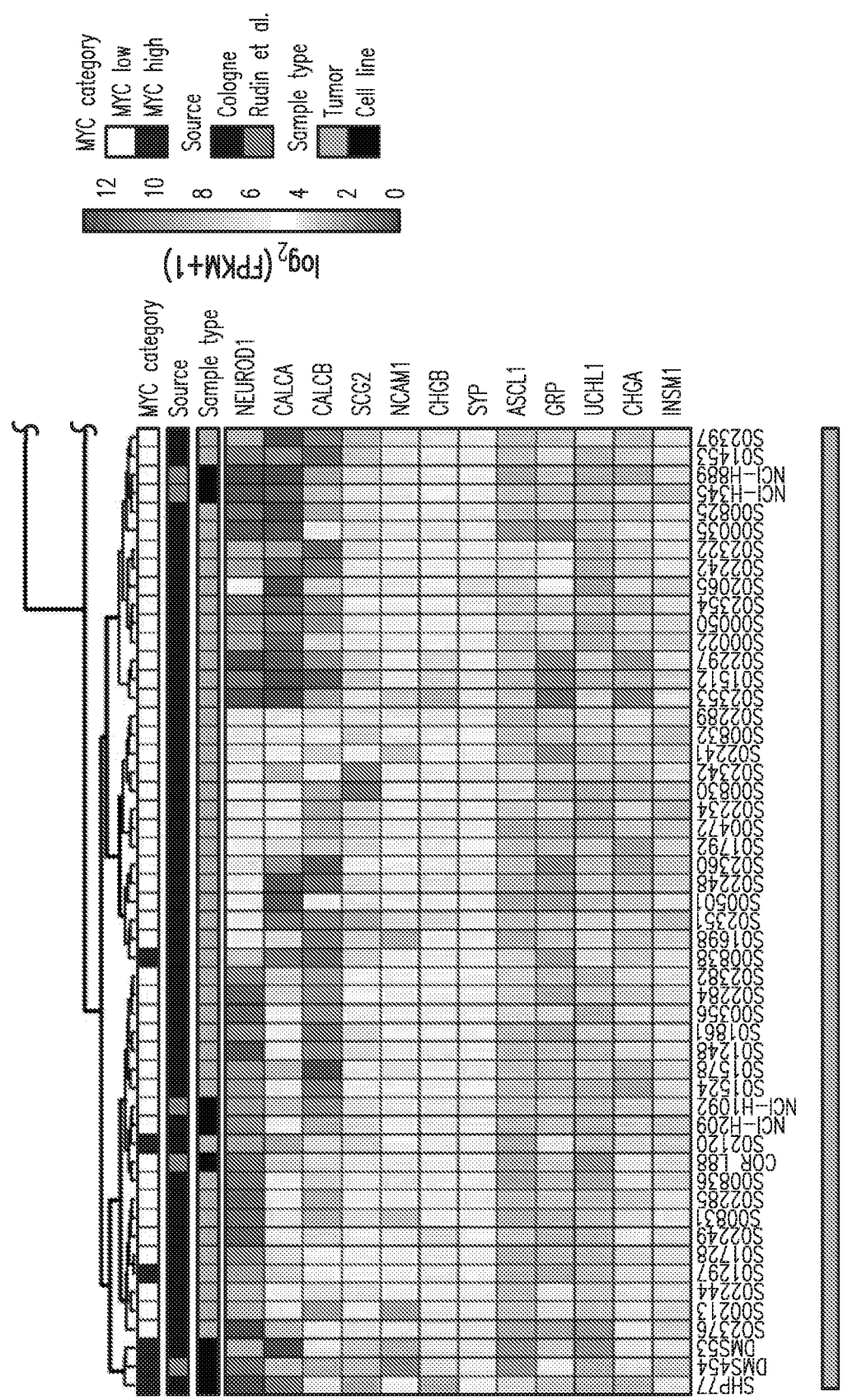
FIGS. 3A-E show that RPM tumors recapitulate molecular subset of MYC-high human small cell lung cancer (SCLC).
Figure 3A:
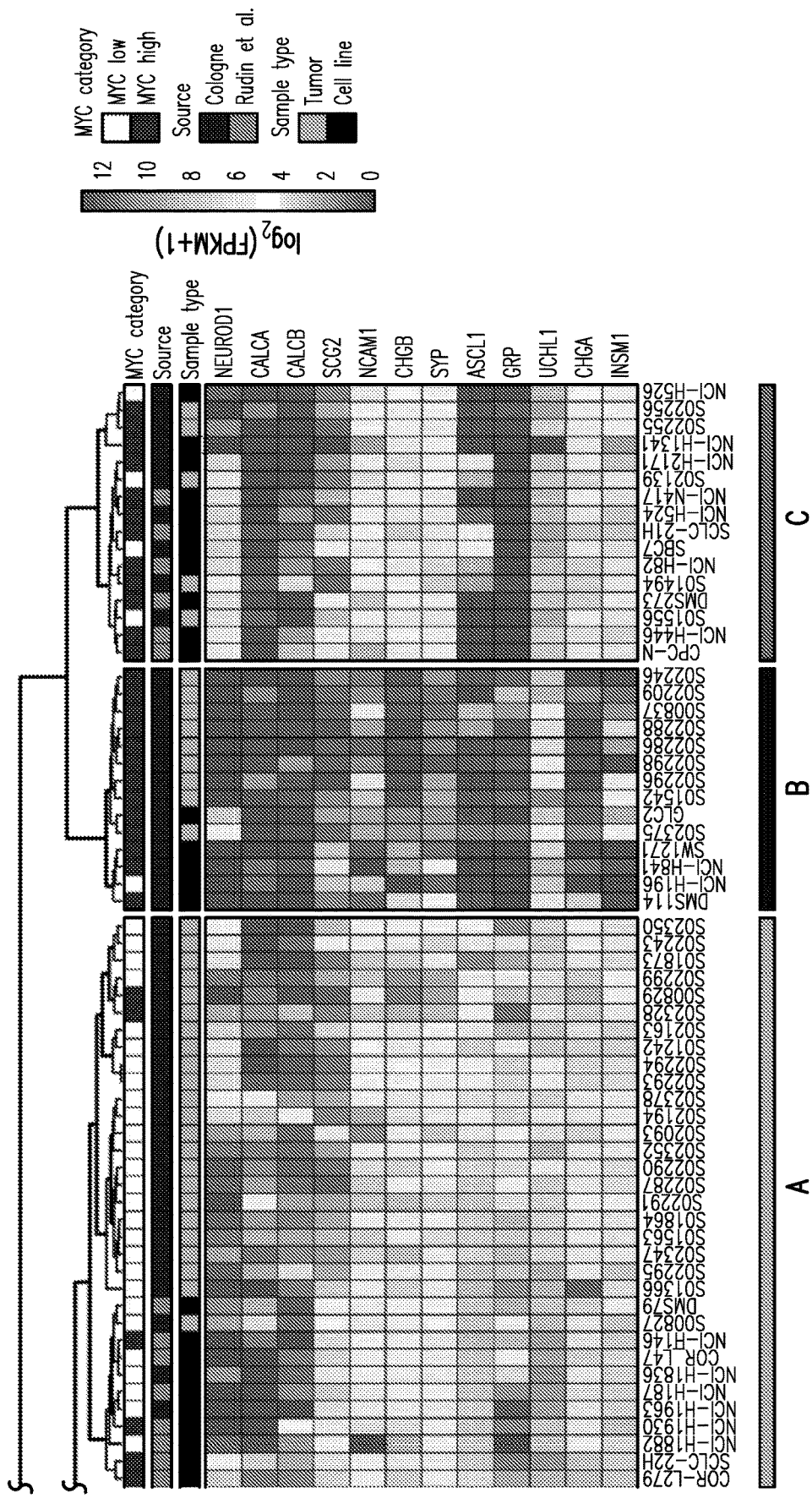
Figure 3B:
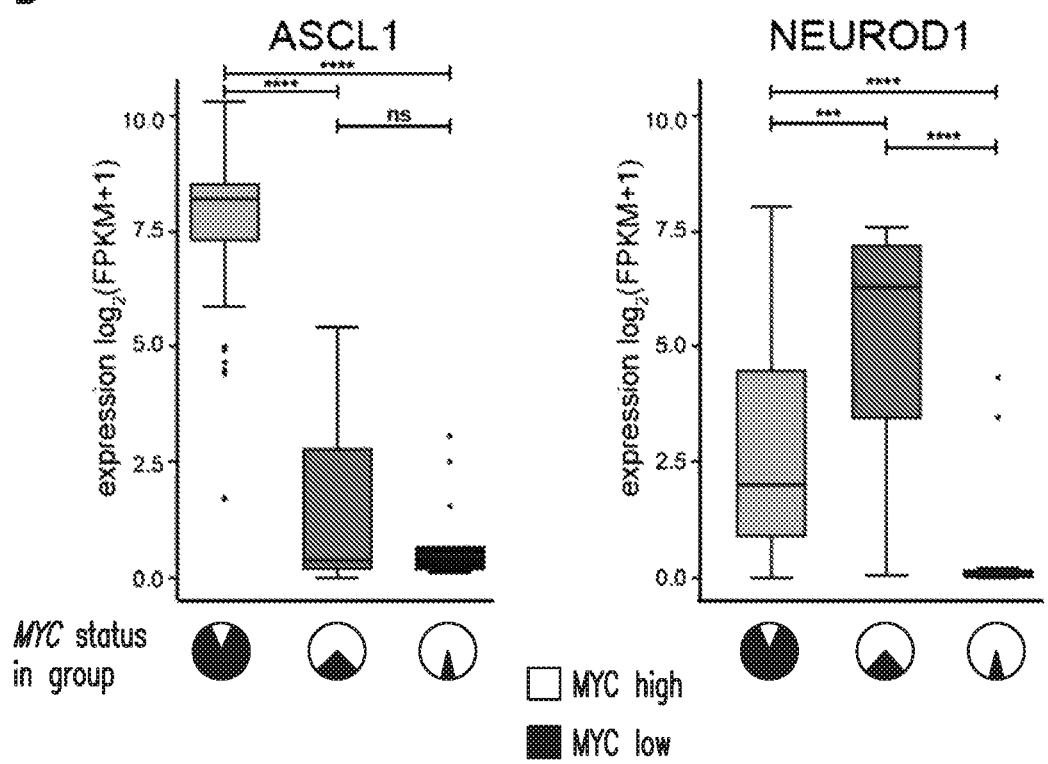
Figure 3C:
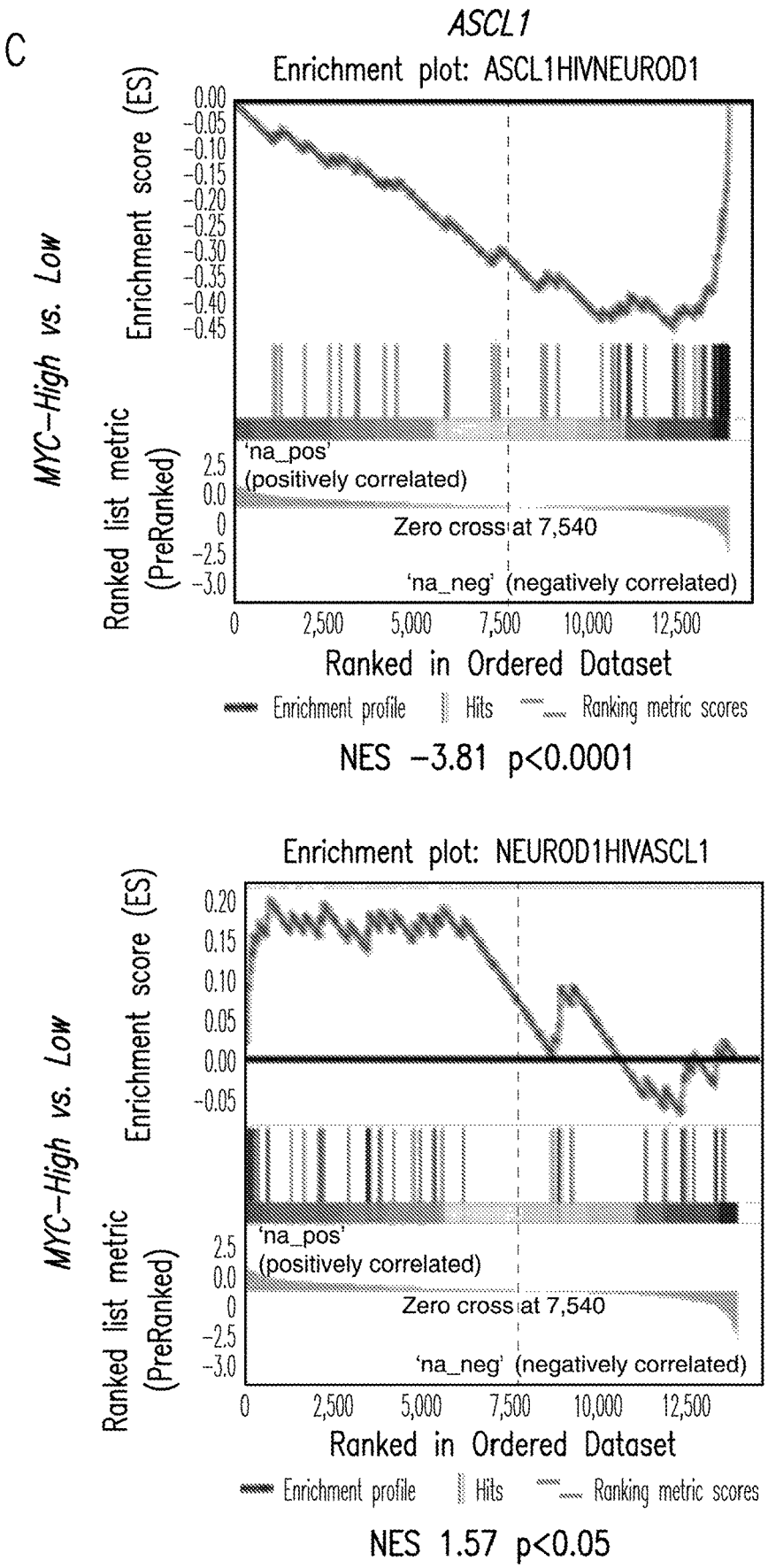
Figure 10A:
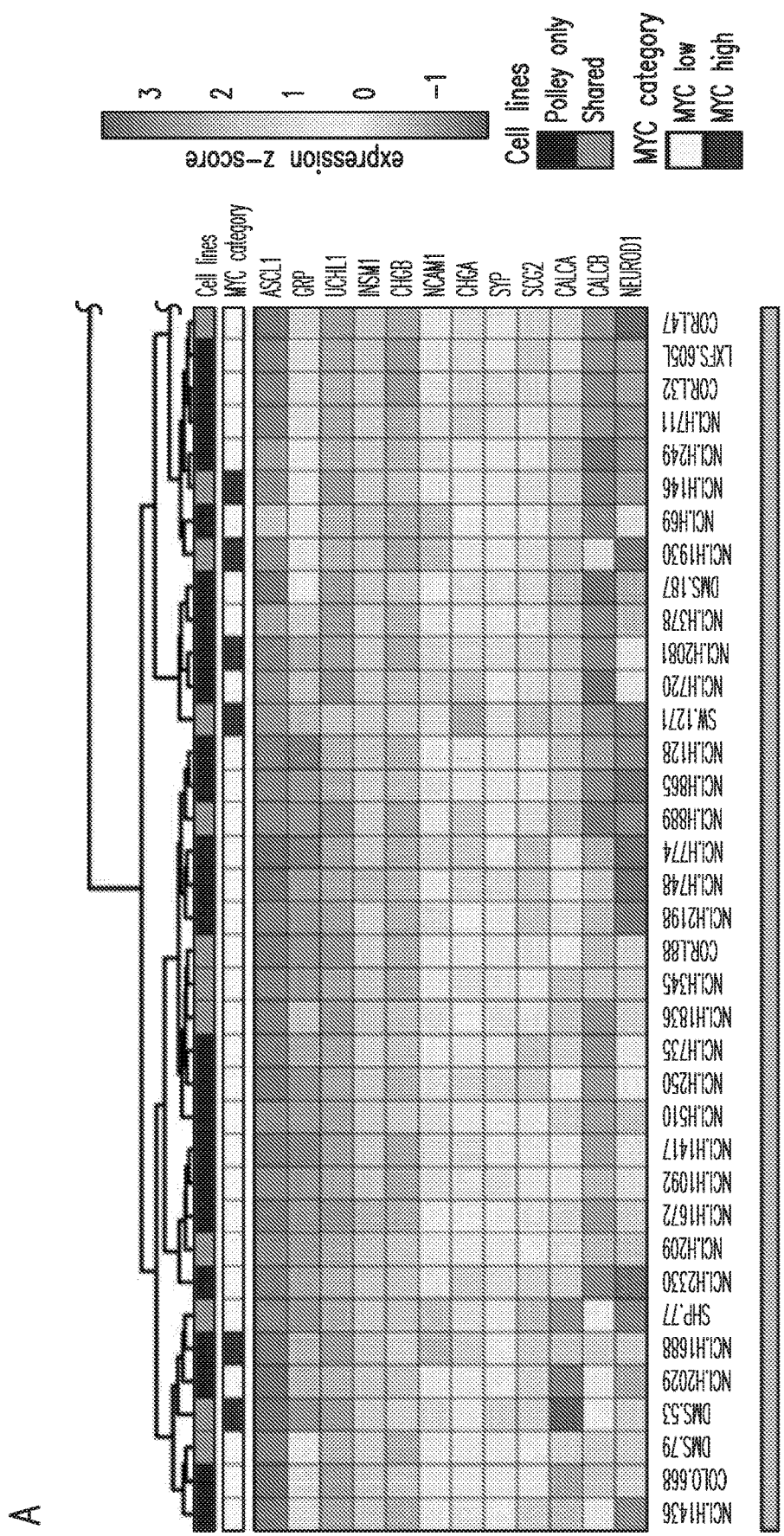
FIGS. 10A-H shows RPM tumors recapitulate molecular subset of MYC-high human SCLC.
Figure 10A:
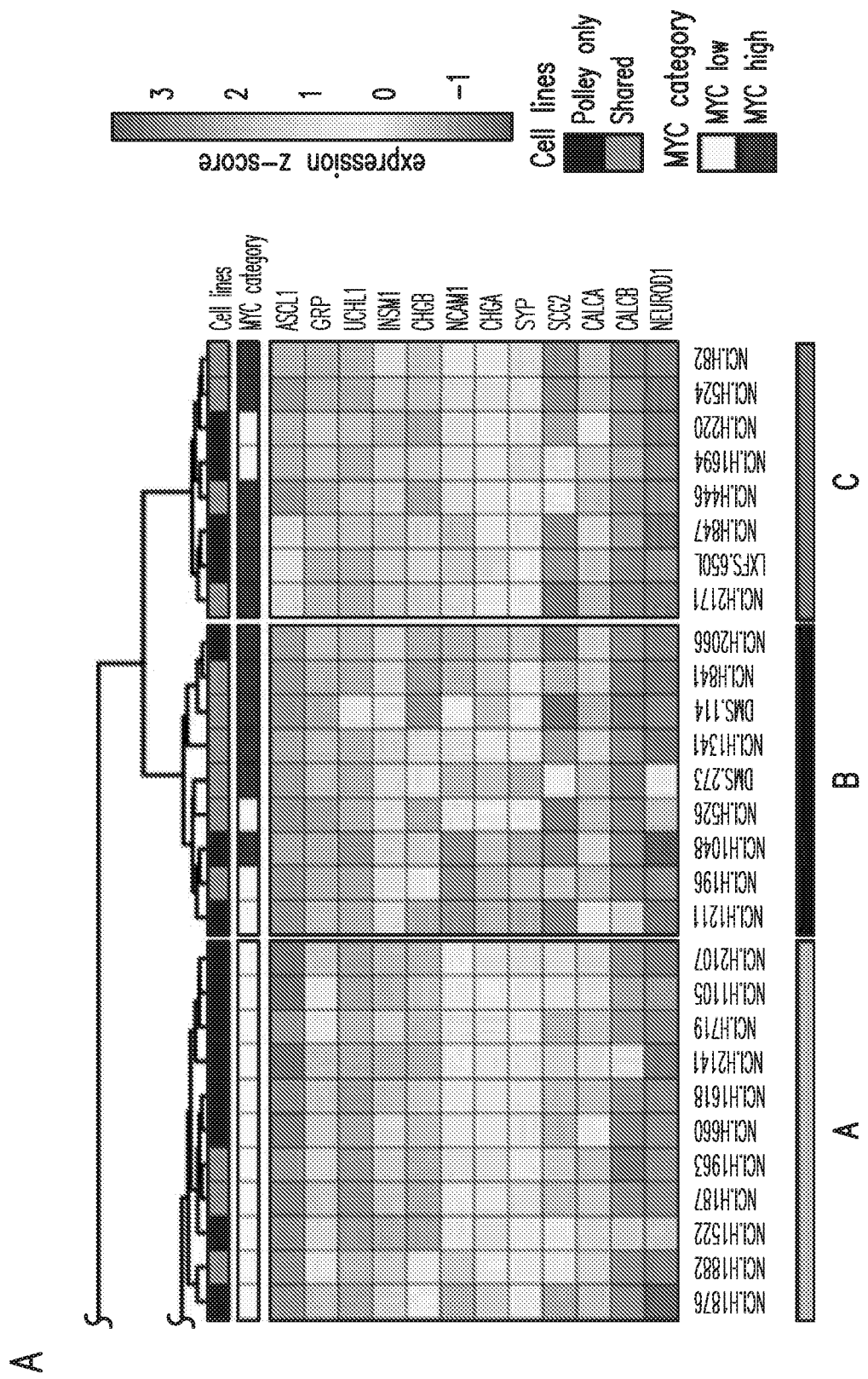
Figure 10B:
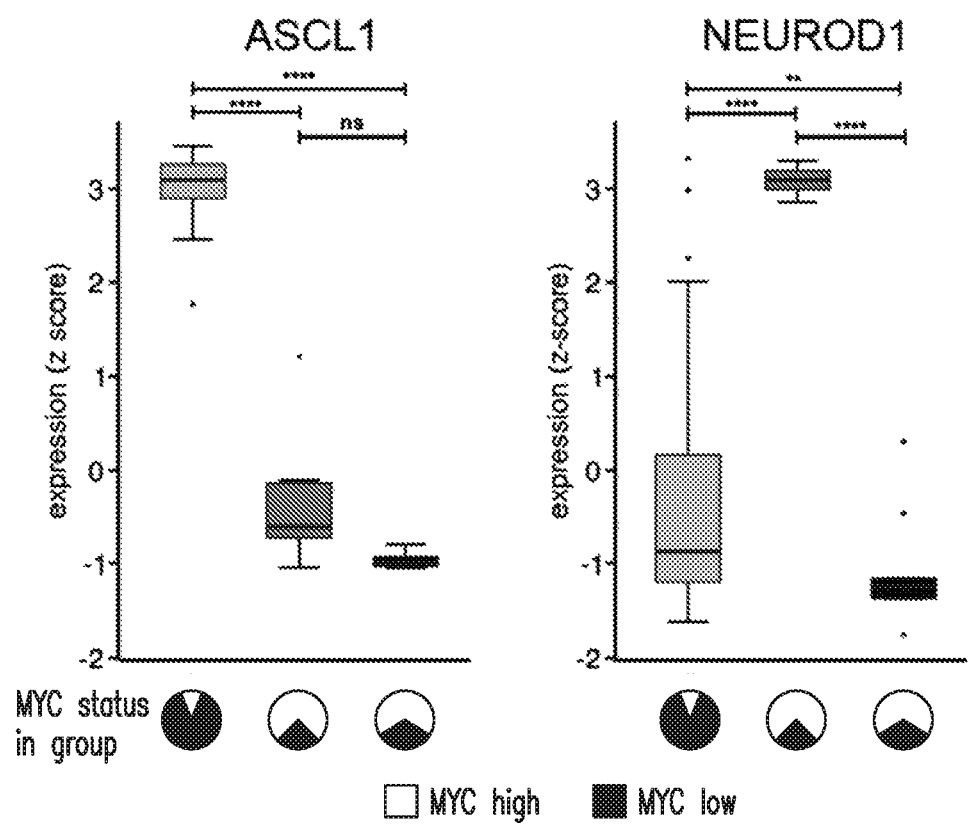

Next, a connection between MYC expression and regulators of neuroendocrine signaling can be recapitulated in human SCLC (Borromeo et al., 2016; Poirier et al., 2013) was investigated. To this end, publicly available transcriptome sequencing data of 81 SCLC specimens (George et al., 2015) and 20 SCLC cell lines (Peifer et al., 2012; Rudin et al., 2012) was collected and performed RNA-seq analysis on 14 additional SCLC cell lines. Hierarchical clustering analysis based on a predefined set of neuroendocrine markers (ASCL1, NEUROD1, SYP, INSM1, CHGA, SCG2, GRP, NCAM1, UCHL1 (PGP9.5) and/or CALCA/B (CGRP alpha/beta)) led to robust separation of samples into groups with either low (group A) or high expression of MYC (groups B and C)(FIG. 3A). Distinct expression patterns of NEUROD1 and ASCL1 in these three groups was observed, which distinguish classic and variant SCLC histology in cell lines and PDX models (Poirier et al., 2013; Poirier et al., 2015). Similar to RP and RPP tumors with low MYC expression (FIG. 2B), high expression of ASCL1 in group A, but low expression of ASCL1 in groups B and C that were enriched for high MYC (FIG. 3B) was observed. In contrast, high NEUROD1 expression was present in group C enriched for high-MYC expressing samples, largely resembling the expression profile of RPM tumors (FIG. 2B). Moreover, GSEA of human patient samples stratified by MYC expression showed a significant enrichment of the NEUROD1$^{high}$ signature in MYC-high samples and enrichment of the ASCL1$^{high}$ signature in MYC-low samples (FIG. 3C). A similar clustering pattern of samples with high MYC expression was observed in a recently published collection of 65 SCLC cell lines (25 shared with the cell lines used herein) that were analyzed using gene expression arrays (FIGS. 10A and 10B)(Polley et al., 2016). Thus, these data show that in RPM mouse tumors, MYC can be associated with differential expression of ASCL1 and NEUROD1 and that these expression profiles are conserved in human SCLC.

Figure 3D:
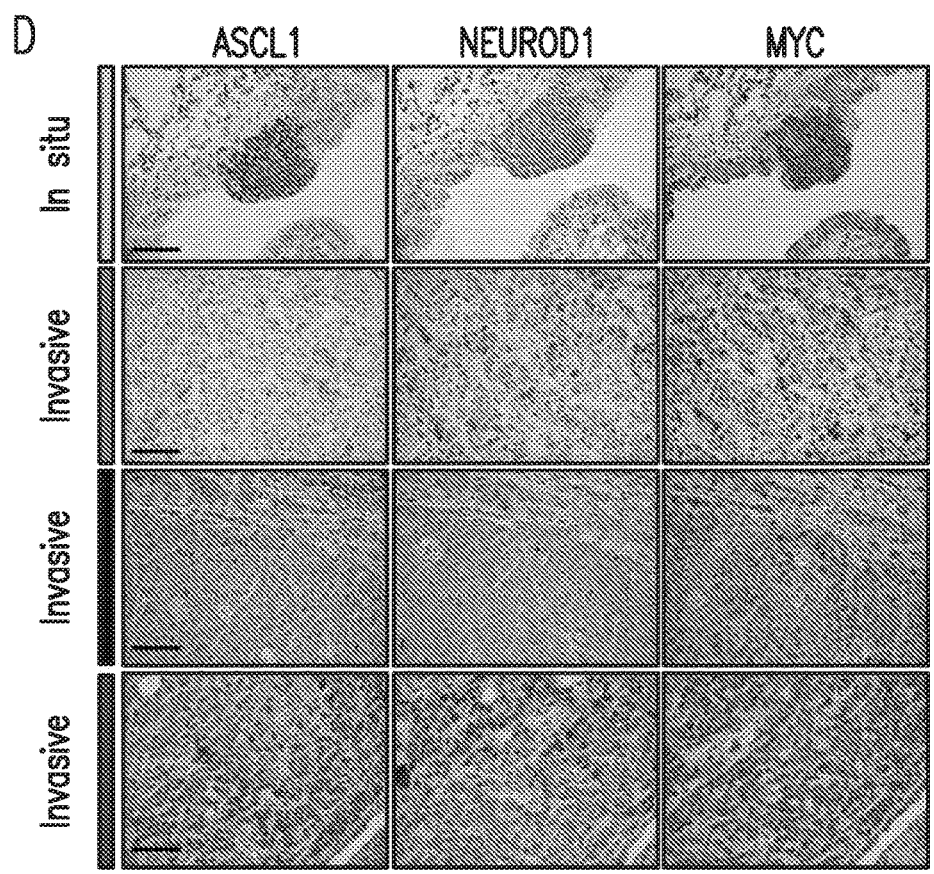
Figure 3E:
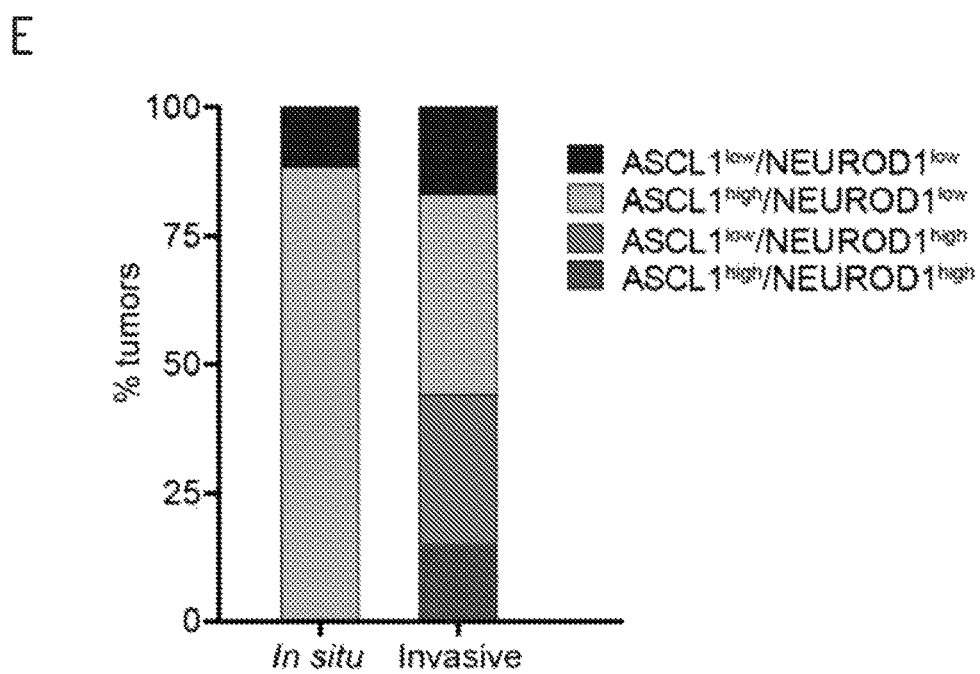
Figure 10C:
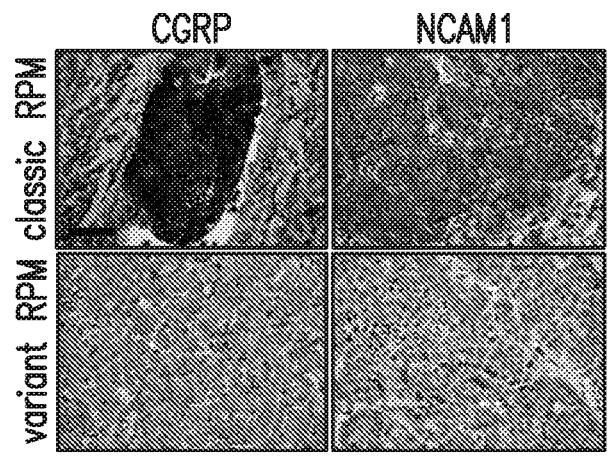
Figure 10D:
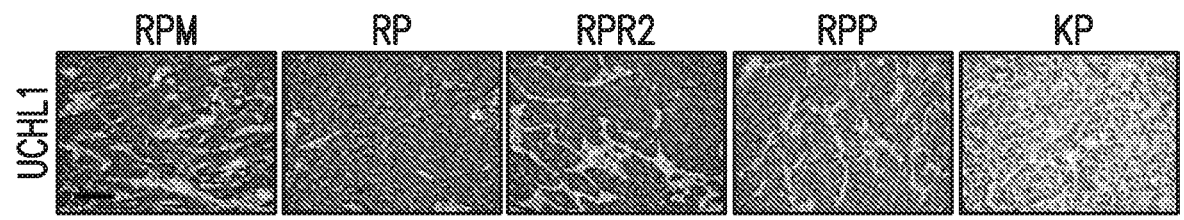
Figure 10D:
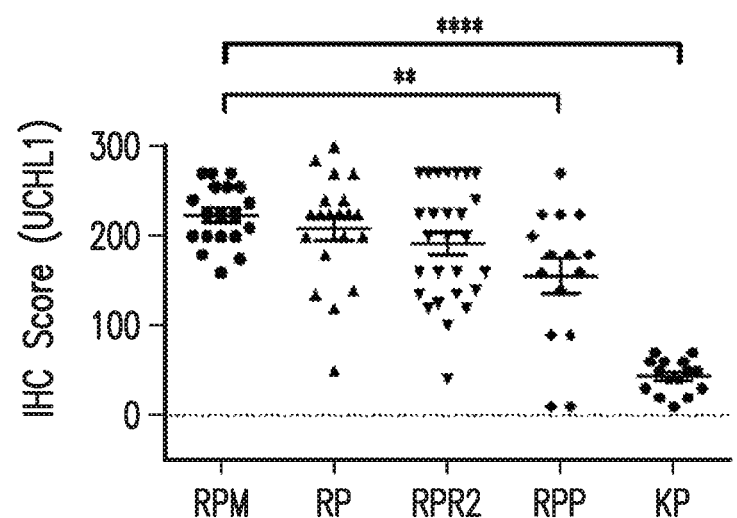
Figure 10E:
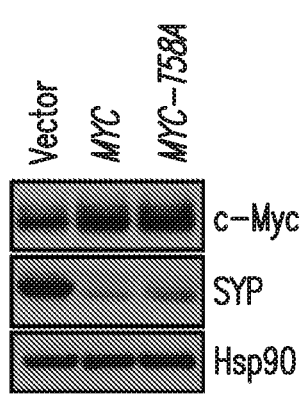
Figure 10F:
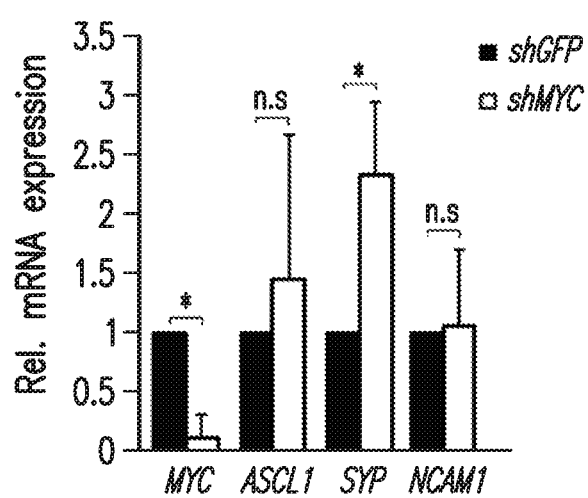
Figure 10G:
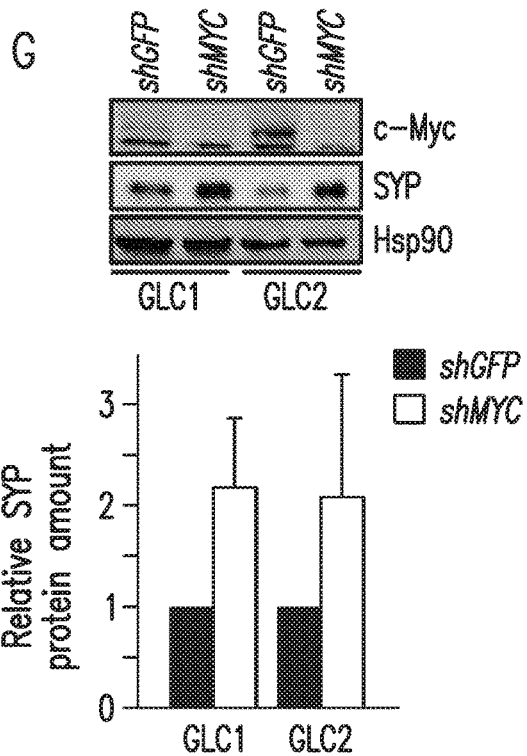
Figure 10H:
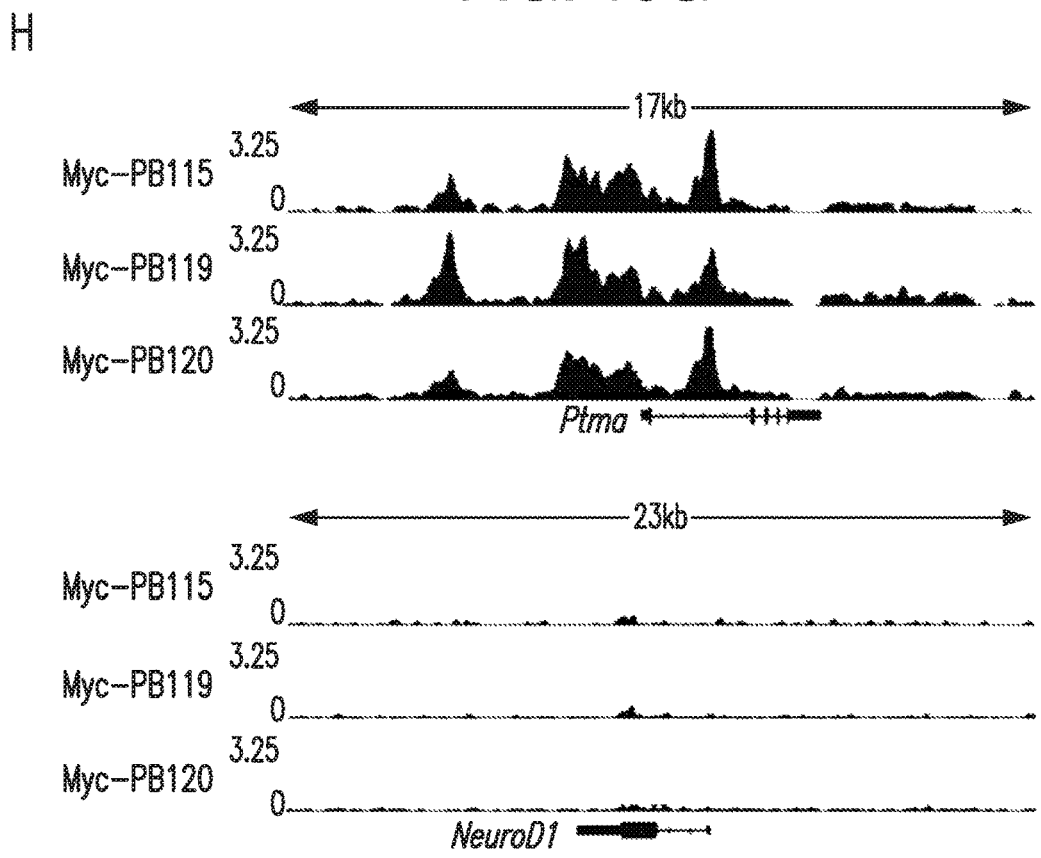

Given the greater variability of ASCL1 and NEUROD1 expression in human SCLC tumors compared to murine tumors by RNA-seq analysis, the RPM mouse model was examined for expression of ASCL1 and NEUROD1 at early (in situ) and late (invasive) time points. The results show that in situ lesions from RPM animals 1-4 weeks post-infection were predominantly classic morphology with high ASCL1 expression (FIG. 3D). Of 26 in situ lesions examined, 23 (88%) were clearly ASCL1+ while none were NEUROD1+ (FIG. 3E). In contrast, 44% of large invasive lesions at 6-8 post-infection (18 of 41) exhibited variant morphology with NEUROD1 expression and either some or no ASCL1 expression. In addition, 17% of tumors were low or negative for both ASCL1 and NEUROD1 similar to the subset of human tumors (group B) with the highest levels of MYC (FIGS. 3D and 3B). Some invasive tumors exhibited high levels of both ASCL1 and NEUROD1, although whether cells are intermixed or co-expressing both proteins cannot be determined by this method. RPM tumors also expressed other neuroendocrine markers including CGRP and Neural cell adhesion molecule 1 (NCAM1), which was evident in classic lesions and reduced in the majority of variant tumors, similar to ASCL1 expression (FIG. 10C). Of note, RPM tumors exhibited robust staining for UCHL1 (also called PGP9.5) (FIG. 10D), which was consistently expressed across murine and human SCLC tumors and cell lines irrespective of MYC status (FIGS. 3A and 2A). Overexpression of MYC in an RP cell line led to repression of Synaptophysin (SYP) (FIG. 10E), while knockdown of MYC in MYC-amplified SCLC cell lines led to an increase in SYP mRNA and protein (FIGS. 10F and 10G), suggesting that MYC may indeed be involved in the modulation of neuroendocrine differentiation. While MYC has been described as a target gene of NEUROD1 (Borromeo et al., 2016), NeuroD1 was not identified as a MYC target gene in RPM cell lines analyzed by ChIP-seq (FIG. 10H). Given that MYC is expressed in in situ lesions in the absence of NEUROD1 expression, this suggests MYC's role in NEUROD1 regulation is likely through indirect mechanisms. Together, this indicates that high MYC expression during tumor progression modulates the neuroendocrine phenotype of SCLC and can lead to advanced lesions with heterogeneous patterns of neuroendocrine differentiation.

As mentioned above, there is a need for SCLC models that recapitulate clinical aspects of the human disease. The short latency of SCLC development in RPM mice can greatly facilitate preclinical studies testing novel therapeutic approaches in SCLC. Myc-driven SCLCs also develop metastases to the lymph nodes and liver with frequencies similar to the human disease, and in manageable time frames for studying mechanisms of metastasis including the role of NFIB. Because the RPM mice are immune-competent, these mice can complement other immune-deficient SCLC models such as PDXs and CDXs (Hodgkinson et al., 2014).

One of the major clinical barriers to SCLC treatment is the rapid development of chemotherapy resistance. Like human SCLC, RPM tumors demonstrate acute sensitivity to chemotherapy, suggesting that MYC alone is not sufficient to promote chemo-resistance. The findings disclosed herein lead to the hypothesis that MYC's role in tumor progression is to promote aggressive proliferation and metastases. The RPM GEMM disclosed herein can serve as a useful tool for uncovering mechanisms of chemo-resistance and for testing novel therapeutic strategies to combat chemo-resistant disease.

Chromatin immunoprecipitation sequencing (ChIP-Seq). ChIP-Seq was performed as previously described (Reddy et al., 2009). Briefly, 20 million cells per ChIP were cross-linked in 1% formaldehyde for 10 minutes at room temperature. Crosslinking was stopped with 125 mM glycine and nuclei were extracted. Chromatin was sonicated using an Epishear Probe Sonicator (Active Motif) for 4 minutes at 40% power. c-MYC (clone D3N8F) antibody (Cell Signaling Technology) was used for immunoprecipitation and an input sample for each cell line served as the control. Libraries were sequenced on an Illumina HiSeq 2500 as single-end 50 bp reads to a minimum depth of 35 million reads per sample. Reads were aligned to the mm10 build of the mouse genome with bowtie (Langmead et al., 2009) using the following parameters: -m 1 -t —best -q -S -l 32 -e 80 -n 2. Peaks were called with MACS2 (Zhang et al., 2008) using a p-value cutoff of 1e-10 and the mfold parameter bounded between 15 and 100. There were 7,830, 13,527 and 5,168 peaks called for PB115, PB119 and PB120, respectively. For visualization, MACS2 produced bedgraphs with the -B and -SPMR options.

Mouse and human cell lines. Mouse primary lung tumors were excised and micro-dissected under sterile conditions. Individual tumors are processed to single cell suspension by mechanical separation using scissors and chemical separation by incubation in 0.25% Trypsin-EDTA (1×) Solution (Gibco, Waltham, Mass., USA) for 20 min. Cell suspensions are filtered through a 100 µm cell strainer and re-suspended in RPMI media. RPM, RPP and RP cells were grown in RPMI, 10% FBS, Pen/Strep and L-Glut in uncoated tissue culture flasks or coated 100 mm plates. LKR10/13 and RP cells were kindly provided by T. Jacks. KP7B and KP10B cells were generated as described above from KP mice and grown in DMEM 10% FBS, Pen/Strep and L-Glut on coated dishes. Human cell line H82 was obtained from ATCC and maintained in RPMI media supplemented with 5% FBS and Pen/Strep. Other human cell lines were as described in Drug Screening.

Mouse cell viability and proliferation assays. Cells were seeded in triplicate (1500/well) in white, flat-bottom 96-well plates. The next day, cells were treated with increasing doses of alisertib (MLN8237, Selleckchem, Houston, Tex.), barastertib (AZD1152-HQPA, Selleckchem, Houston, Tex.), cisplatin (Acros Organics, NJ, USA) or etoposide (Sigma, St. Louis, Mo., USA). After 96 hrs of treatment, cell viability was measured using Cell Titer Glo (CTG, Promega, Madison, Wis., USA) on a luminometer. Normalized, transformed dose response curves were generated and analyzed using GraphPad Prism (GraphPad, La Jolla, Calif., USA) to determine GI50 for each compound. For proliferation rates, cells were seeded in a clear 96-well plate (5000 cells/well) and imaged every 2 hrs for 96 hrs on an IncuCyte Zoom system (Essen Bioscience, Michigan, USA) at 37° C. and 5% CO2. Confluence percentage at each time point was calculated by the Essen IncuCyte software.

Cell cycle analysis. Cells were treated with indicated concentrations of alisertib (MLN8237, Selleckchem, Houston, Tex.) in 6-well plates and harvested with trypsin, washed twice in PBS, and 1×106 cells were fixed in ice-cold 70% ethanol overnight. Cells were washed 2× in PBS/1% BSA, treated with 100 µg/mL RNase for 10 min at 37° C., then stained with 25 µg/mL propidium iodide (PI) overnight at 4 C. Cells were analyzed on a BD FACScan flow cytometer and cell cycle analysis excluding cell doublets was performed using FlowJo software.

Drug screening. Human SCLC cell lines were cultured in RPMI or HITES as described before (Sos et al., 2012). For screening of cisplatin and etoposide, 4000 cells per well were grown on 96-well flat bottom assay plates for 24 hrs prior to treatment with cisplatin (Uniklinik Apotheke, dissolved in PBS) or etoposide (Sigma-Aldrich, dissolved in DMSO) starting at the maximum concentration of 10 µM. After 96 hr, cell viability was analyzed using CTG reagent. Each cell line and concentration was analyzed in triplicate per experiment and the GI50-value (growth inhibition of 50%) calculated using GraphPad. The average GI50-value of at least three independent trials is depicted. For PF-670462 (Apexbio), MS436 (MedChem Express), barasertib/1152-HQPA (Apexbio), alisertib/MLN8237 (Apexbio) and milciclib/PHA-848125 (MedChem Express), all dissolved in DMSO, indicated cell lines were screened using the same protocol in 384-well format with 500 (adherent) or 5000 (suspension) cells per well (25 ml) and treated using a robotic system (CyBio CyBi well vario). Upon treatment, cells were incubated for 72 hr prior to addition of CTG reagent. Each cell line and concentration was analyzed in quadruplicate per experiment with n=3 independent trials.

Bioinformatic analyses of published drug screen. Publically available gene expression and drug response data from Polley (Polley et al., 2016) were downloaded from https://sclccelllines.cancer.gov/sclc/downloads.xhtml. Log 10 IC50 µM values were set to 2 if above the tested range and −3 if below. SCLC samples were binned into two groups based on MYC expression where cells with log 2 expression values above 8.5 were categorized as high. The base R (v3.2.2) function wilcox.test was used to test for Log 10 IC50 differences between low and high MYC groups.

shRNA-mediated MYC knockdown in human cell lines. Lentiviral production was carried out essentially as previously described (Sos et al., 2012) for pLKO.1-shGFP or pLKO.1-shMYC. Briefly, HEK293T cells were transfected with pLKO.1 puro based vectors and pMD.2 and pCMVd.8.9 helper plasmids using TransIT-LT1 (Minis Bio). 48 and 72 hr post-transfection replication-incompetent lentiviral particles were harvested and cells (GLC1, GLC2, H82) infected in presence of 10 µg/ml polybrene (Santa Cruz Biotechnology). Puromycin (1.5 µg/ml) selection was started after 16 hr and cells harvested 72 hr later (RNA extraction) or 96 hr (SYP Western blot). The following shRNA target sequences were used: GFP (GAAGCAGCACGACTTCTTC) (SEQ ID NO: 5), MYC (CCTGAGACAGATCAGCAACAA) (SEQ ID NO: 6). Knockdown efficiency was assessed by qRT-PCR or immunoblot.

MYC overexpression in mouse cell line. HEK293T cells were transfected with pMSCV PIG (Addgene Plasmid #21654), empty vector or vector with insert that encodes the mouse Myc sequence; either WT or T58A mutant in addition to pCMV-VSVG and pCMV delta R8.2 plasmids using TransIT-LT1 (Minis). Viruses were collected at 48 and 72 hr post-transfection. 3151T1 mouse SCLC cell line was infected with viral supernatant with 8 µg/ml polybrene (Santa Cruz Biotechnology). Infected cells were selected with puromycin (5 µg/ml) for several days until all uninfected control cells were killed by puromycin. Infection efficiency was verified by fluorescence microscopy after selection as more than 90% of cells were GFP positive. Cells were harvested for immunoblotting as previously described.

Quantitative RT-PCR human cell lines after MYC knockdown. GLC1, H82 and GLC2 were infected with two independently generated MYC and GFP shRNA lentiviruses. 72 hr post selection for the shRNA total RNA was extracted according to the manufacturer's protocol (RNeasy Mini Kit, Qiagen). One µg total RNA was used for cDNA synthesis with SuperScript II RT (Invitrogen) according to the manufacturer's protocol. Quantitative real-time PCR (qRT-PCR) reactions were carried out in duplicate per sample using a 7300 Real-Time PCR System (Applied Biosystems) with Power SYBR Green PCR Master Mix (Applied Biosystems) and the following oligos: MYC-1f (CCTACCCTCTCAACGACAGC) (SEQ ID NO: 7), MYC-1r (CTCTGACCTTTTGCCAGGAG) (SEQ ID NO: 8), ASCL1-1f (CGACTTCACCAACTGGTTCT) (SEQ ID NO: 9), ASCL1-1r (CCGTGAATGATTGGAGTGC) (SEQ ID NO: 10), ASCL1-2f (GCTCTGCCAAGATGGAGAG) (SEQ ID NO: 11), ASCL1-2r (CTGTCGCTTGACTTGCTTG) (SEQ ID NO: 12), SYP-1f (ACCTCGGGACTCAACACCTC) (SEQ ID NO: 13), SYP-1r (CTGAGGCCCGTAGGAATC) (SEQ ID NO: 14), SYP-2f (CTCCTTCTCCAATCAGATG) (SEQ ID NO: 15), SYP-2r (CAAGACTGGGCACCTAGTG) (SEQ ID NO: 16), NCAM1-1f (GTGTGGTTACAGGCGAGGAT) (SEQ ID NO: 17), NCAM1-1r (GATGACATCTCGGCCTTTGT) (SEQ ID NO: 18), Actin-f (GTCTTCCCCTCCATCGTGG) (SEQ ID NO: 19), Actin-r (GATGCCTCTCTTGCTCTGGG) (SEQ ID NO: 20). Ct values were calculated using the 7300 System Software. Replicates per primer pair were averaged and normalized via dCt to Actin as a reference control. Average dCt values from each virus preparation per cell line were used to calculate ddCt values between shMYC and shGFP. Relative expression of knockdown vs. control was displayed across cell lines and primers as average 2-ddCt with SEM.

Methods and materials used are described herein and above.

Figure 4D:
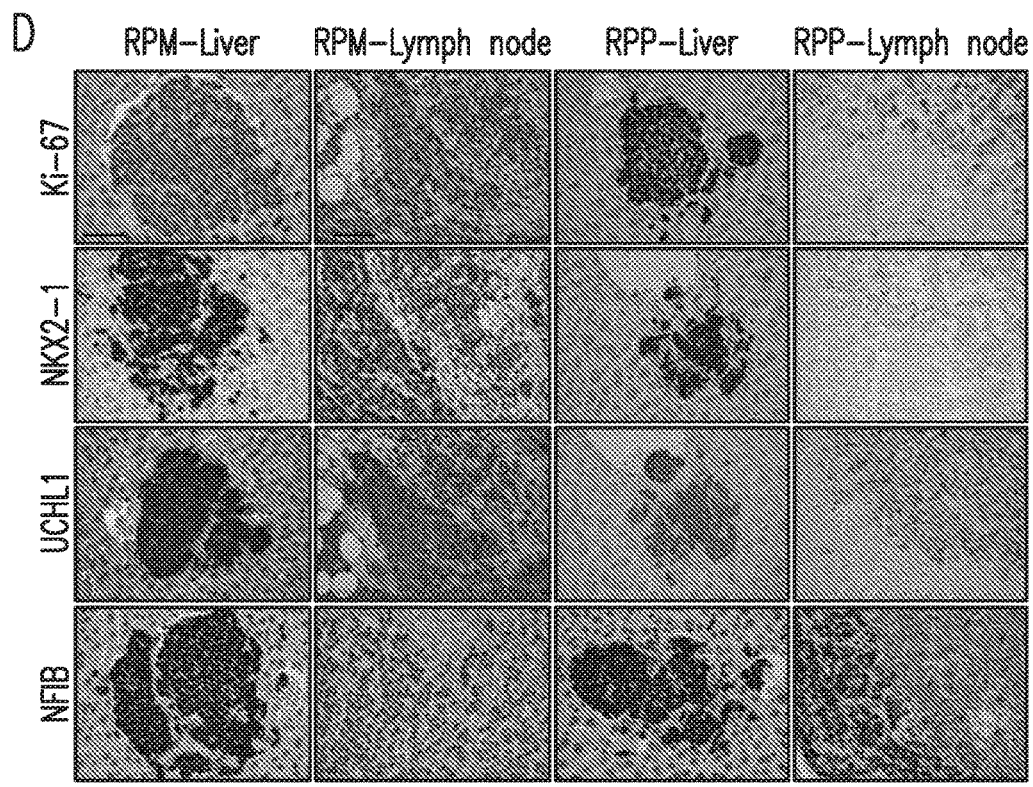
Figure 4E:
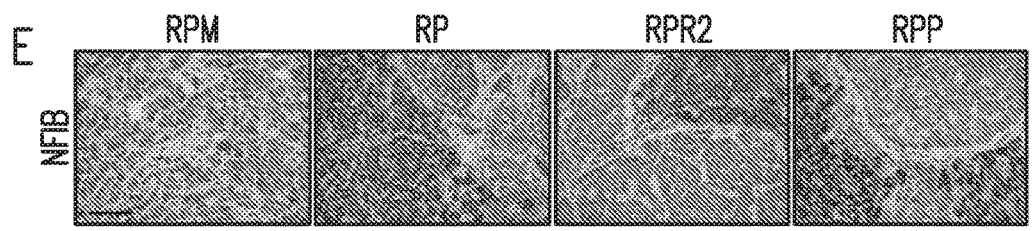
Figure 4F:
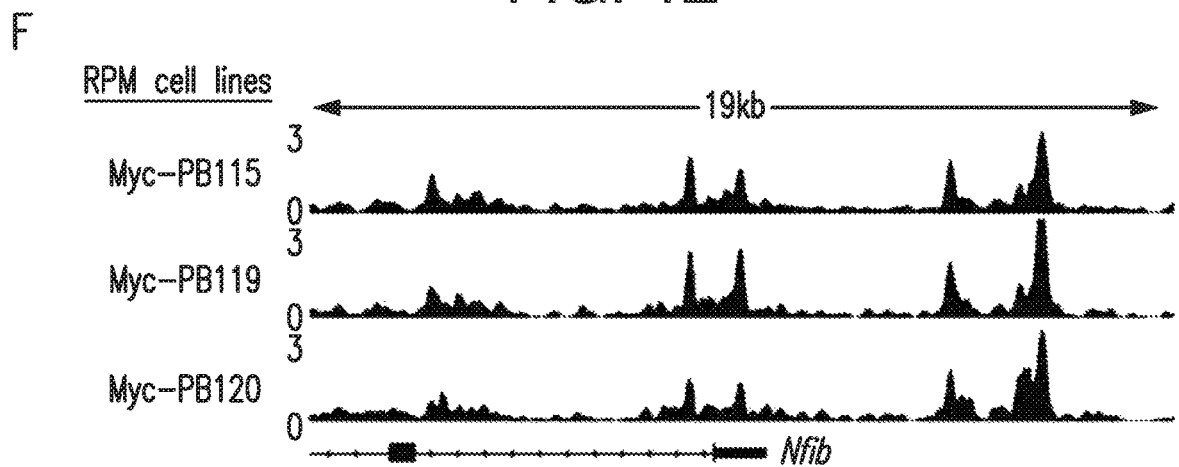

Example 4: Myc-Driven Tumors are Highly Metastatic Similar to the Human Disease To assess whether Myc-driven tumorigenesis was associated with metastases, liver and lymph nodes were collected from tumor-bearing RPM mice at 8 weeks and RPP mice at 24 weeks to control for the amount of primary tumor burden in each genotype. Mediastinal spread via lymphatics and blood borne metastases in the liver were prominent in some mice (FIGS. 4A and 4B). Out of 16 livers from RPM mice, 14 (~88%) exhibited liver metastases, often presenting with multiple micro-metastases (FIGS. 4A and 4C). Remarkably, clusters of tumor cells were identified in the blood vessels of the liver, and were proliferating as evidenced by multiple mitotic cells (FIG. 4A). Despite the much longer time frame for tumor development, RPP animals demonstrated significantly fewer liver metastases (36%) (FIG. 4C). Fifteen out of 21 RPM mice (~71%) also exhibited metastases to mediastinal and distant lymph nodes (FIG. 4B). Metastases were highly proliferative based on Ki67 staining and stained strongly for NKX2-1 and UCHL1 (FIG. 4D), consistent with a lung neuroendocrine origin. RPM tumors exhibited high levels of the metastatic driver NFIB in both primary tumors and metastases (FIG. 4D), but did not exhibit Nfib amplifications that are commonly found in Mycl-driven SCLC (FIG. 9A)(Denny et al., 2016; Dooley et al., 2011; Semenova et al., 2016). However, consistent with its homogeneous expression in primary tumors (FIG. 4E), Nfib was identified as a MYC target gene by ChIP-seq of mouse RPM cell lines (FIG. 4F). Binding of MYC was detected, for example, near the Nfib gene. This suggests that MYC directly regulates Nfib, which may contribute to rapid metastases. Together the metastatic pattern of Myc-driven mouse SCLC resembles human SCLC, and occurs much more rapidly than in other classic GEMMs (McFadden et al., 2014; Meuwissen et al., 2003; Schaffer et al., 2010).

Methods and materials used are described herein and above.

Figure 5A:
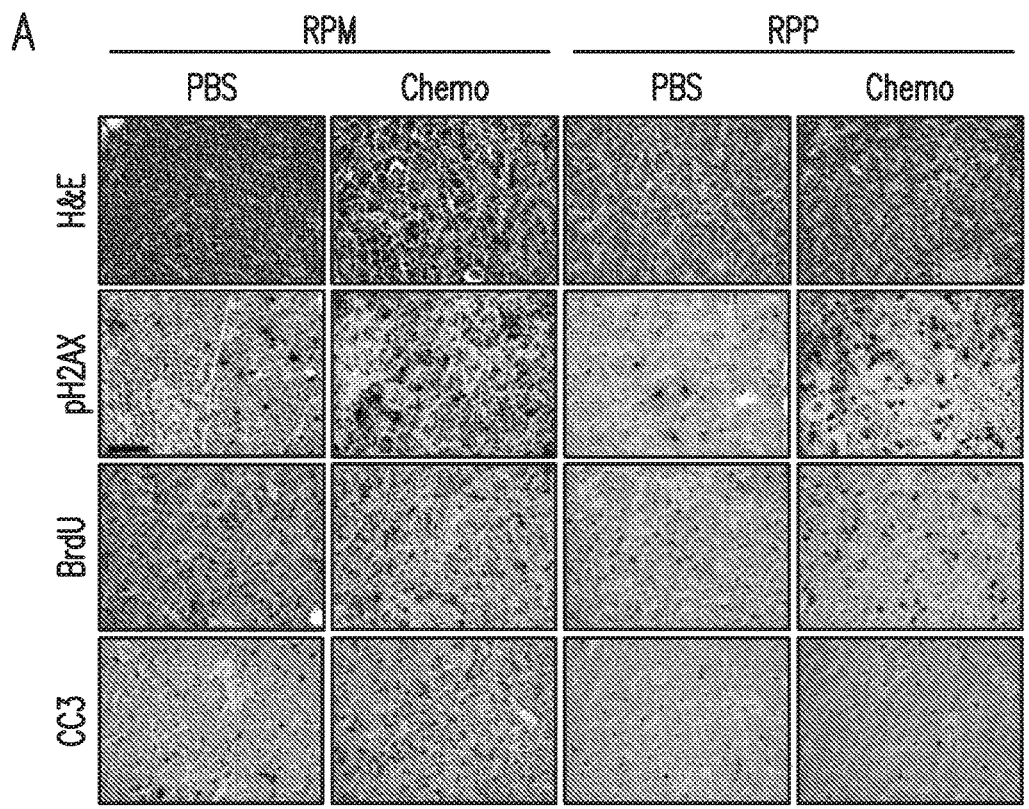
Figure 5B:
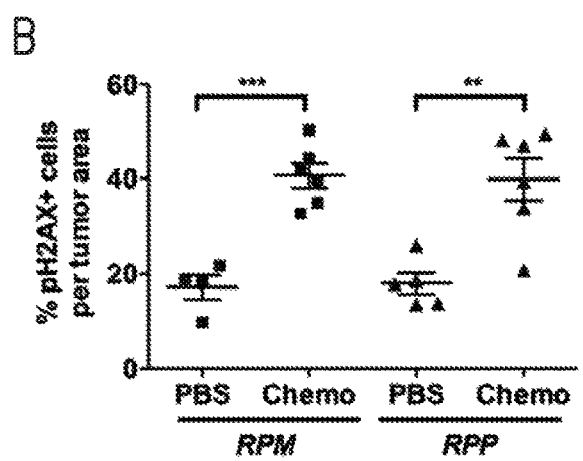
Figure 5C:
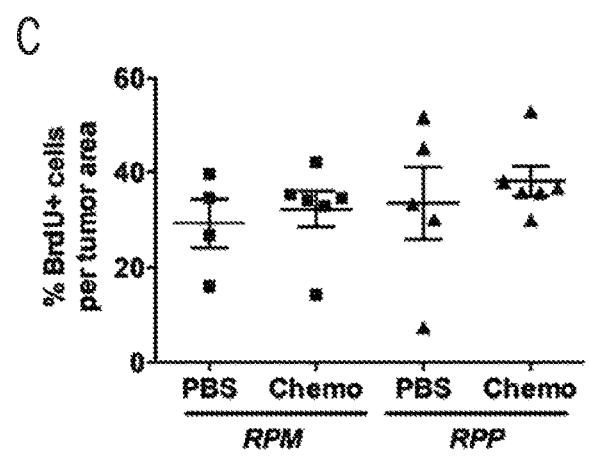

Example 5: Myc-Driven SCLC is Highly Responsive to Chemotherapy, but Rapidly Relapses Human SCLC is responsive to chemotherapy, but the influence of MYC on chemotherapy response is controversial and in vivo results have not been publically reported (Hodgkinson et al., 2014; Johnson et al., 1987). To address this, RPM and RPP mice were treated with or without a single dose of 7 mg/kg cisplatin (day 1) and 10 mg/kg etoposide (day 2), followed by a single 24-hour pulse of BrdU, and then collected lung tissue for IHC analyses. In the absence of chemotherapy, control tumors of both genotypes exhibited detectable DNA damage measured by levels of phospho-histone H2A.X (pH2AX) (FIG. 5A). In response to chemotherapy, RPM and RPP tumors exhibited a significant increase in pH2AX as expected (FIGS. 5A and 5B). In contrast to adenocarcinomas that exhibit a strong cell cycle arrest following chemotherapy (Oliver et al., 2010), neither RPM nor RPP tumors exhibited reduced proliferation (FIGS. 5A and 5C). Instead, chemotherapy-treated RPM tumors had significantly increased levels of CC3 compared to untreated controls, which was not observed in RPP tumors (FIGS. 5A and 5D). Together, these data suggest that high levels of DNA damage coupled with a failure to arrest the cell cycle leads to apoptotic cell death in RPM tumors.

Figure 5F:
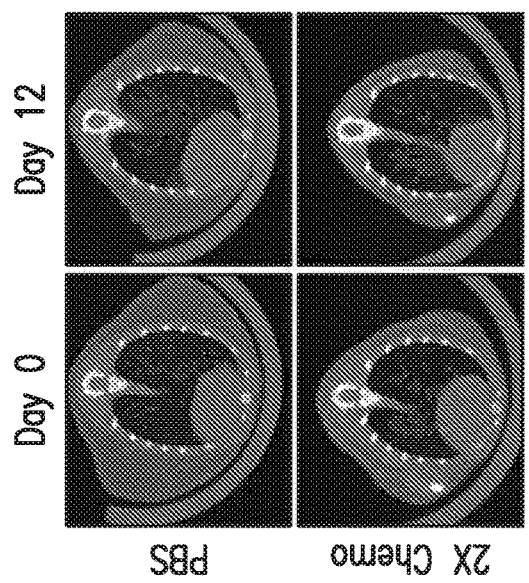
Figure 5G:
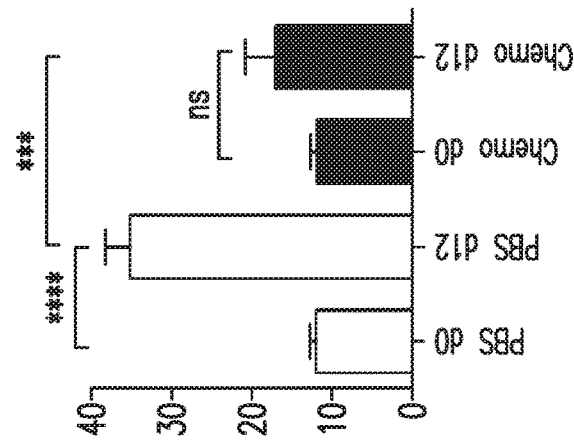
Figure 5G:
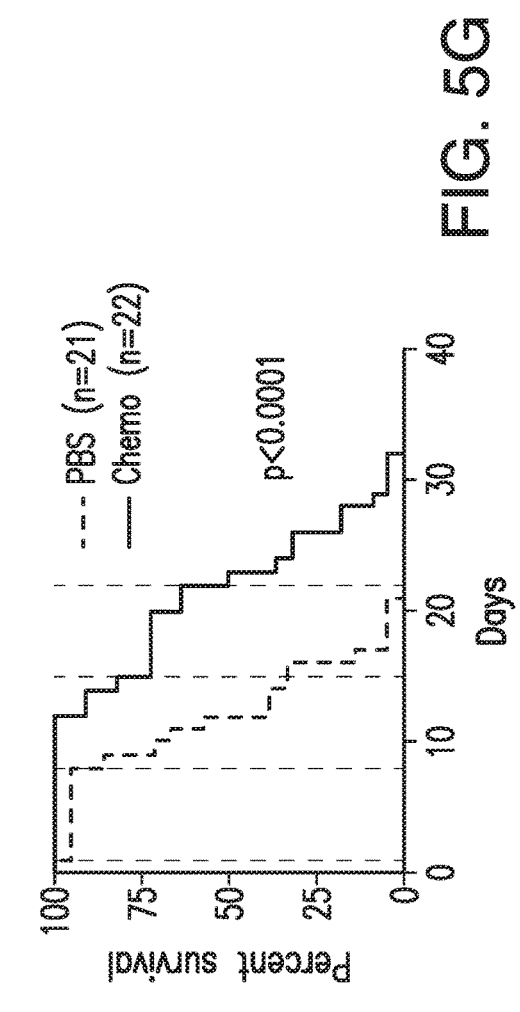

Because of the dramatic response to a single dose of chemotherapy, the next set of experiments was carried out to determine whether chemotherapy could reduce tumor burden in RPM animals. A cohort of RPM mice were treated with two doses of combination chemotherapy (5 mg/kg cisplatin and 10 mg/kg etoposide) or vehicle control and harvested lung tissue 72 hours after the second dose. RPM tumors treated with chemotherapy exhibited dramatically reduced tumor burden (3.8+/−1.6%) compared to control animals (19.5+/−3.1% tumor burden) (FIG. 5E), indicating that Myc-driven tumors are indeed chemo-sensitive. Whole slides from each RPM animal treated with PBS control or two doses of combination checmotherapy as in FIGS. 5E and 5F. MicroCT imaging provides a more comprehensive assessment of tumor burden, so tumor burden was also quantified before treatment (d0) and again on day 12 (d12) following two doses of chemotherapy. PBS-treated tumors grew significantly from 12% to 35% tumor burden in 12 days, whereas chemotherapy-treated tumors had minor increases from 12% to 17% tumor burden that were not significantly increased (FIG. 5F). Heterogeneity was observed in the response of individual tumors including progression, stasis and regression. In another cohort of RPM mice, combination chemotherapy significantly prolonged survival, but the overall added survival benefit was 10.5 days (FIG. 5G). The majority of lungs from RPM mice receiving repeated chemotherapy still harbored tumors suggesting that they had possibly acquired resistance to chemotherapy. These data suggest that RPM tumors accurately reflect the clinical response of human SCLC. While Myc alone does not confer chemo-resistance per se, Myc-driven tumors rapidly relapse following treatment.

Methods and materials used are described herein and above.

Example 6: Myc-Driven SCLC is Vulnerable to Aurora Kinase Inhibition

Figures 6A, 6B:
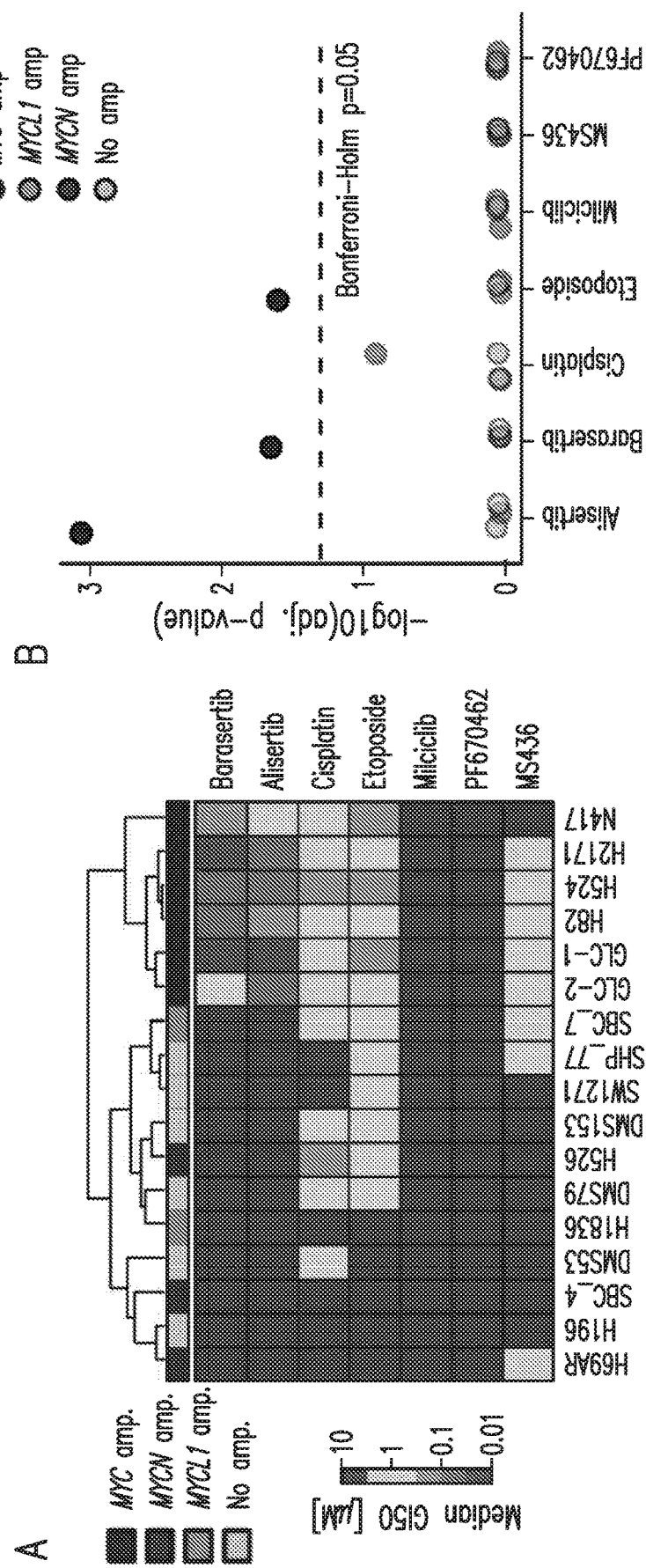
FIGS. 6A-H show that Myc-driven small cell lung cancer (SCLC) is vulnerable to Aurora kinase inhibition.
Figure 6C:
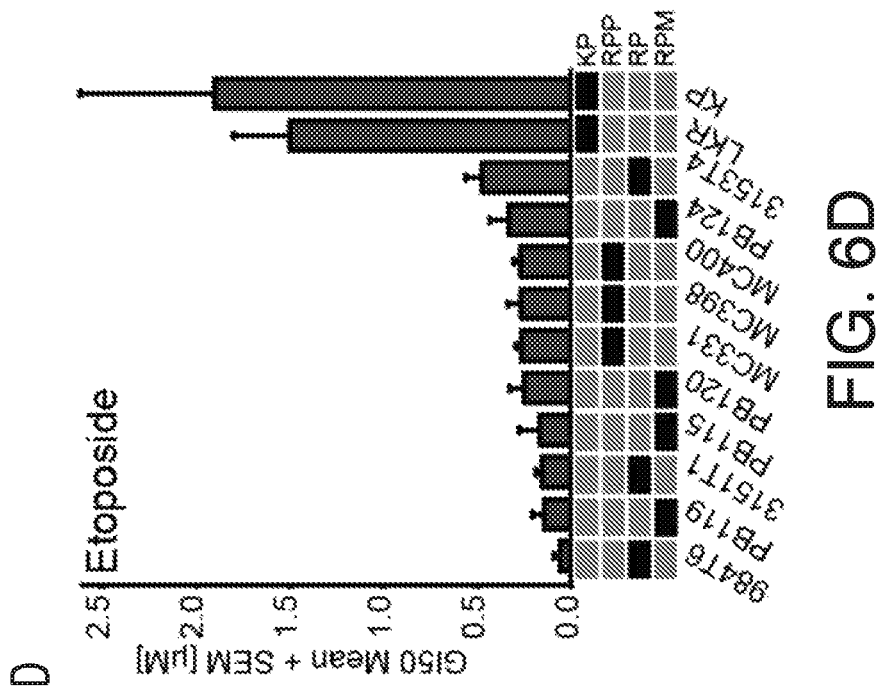
Figure 6D:
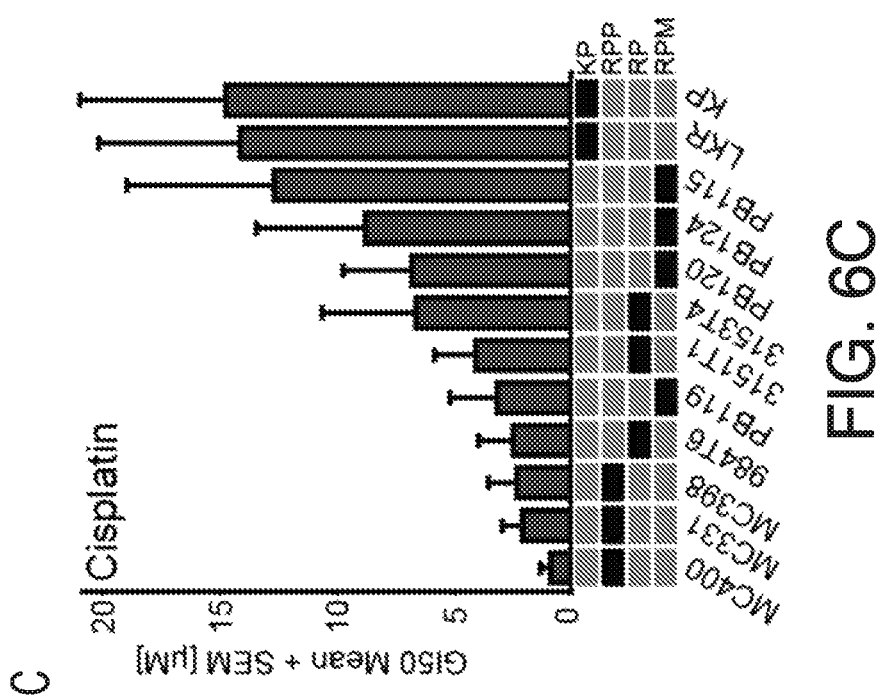
Figures 6E, 6F:
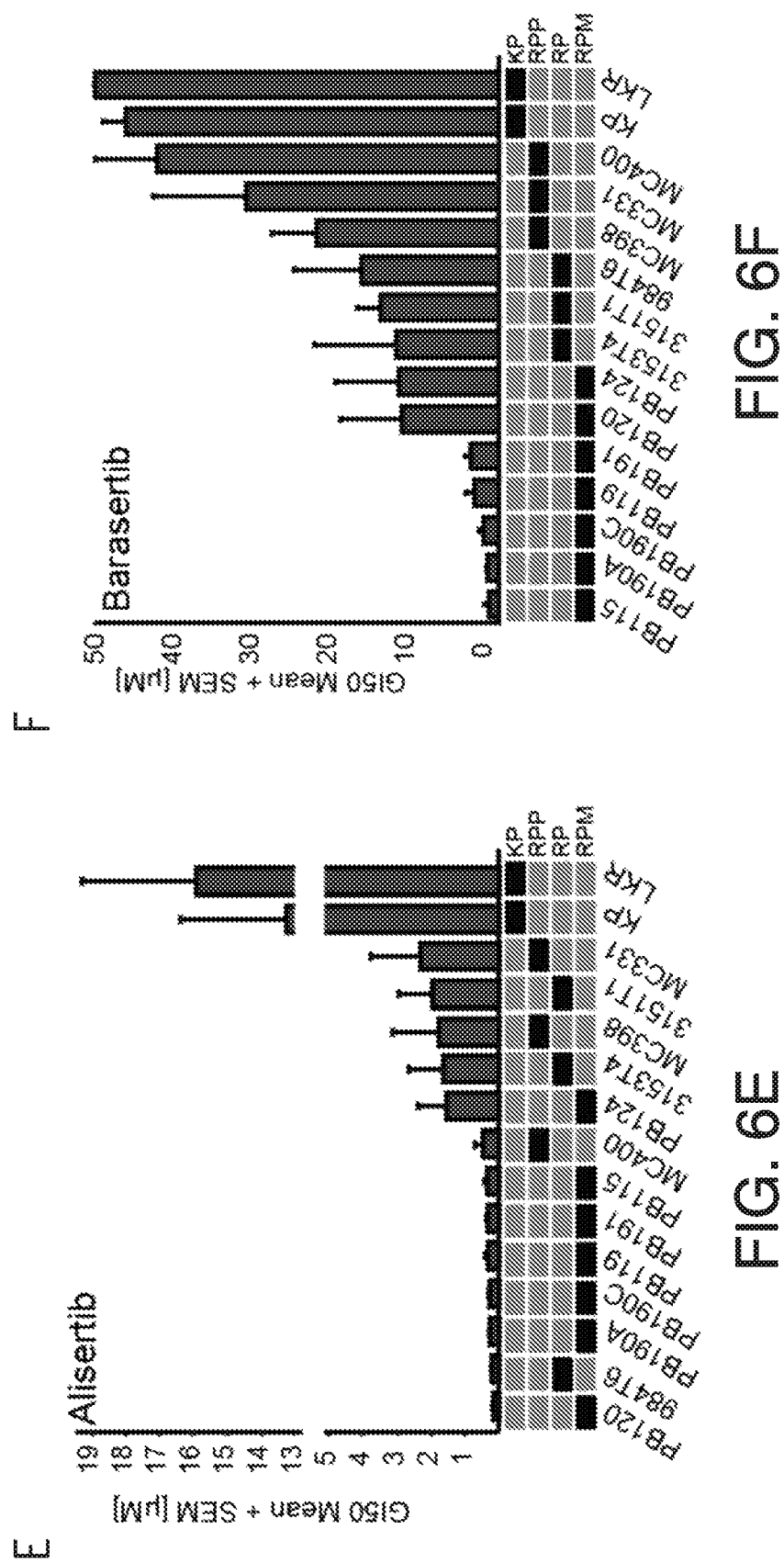
Figure 6G:
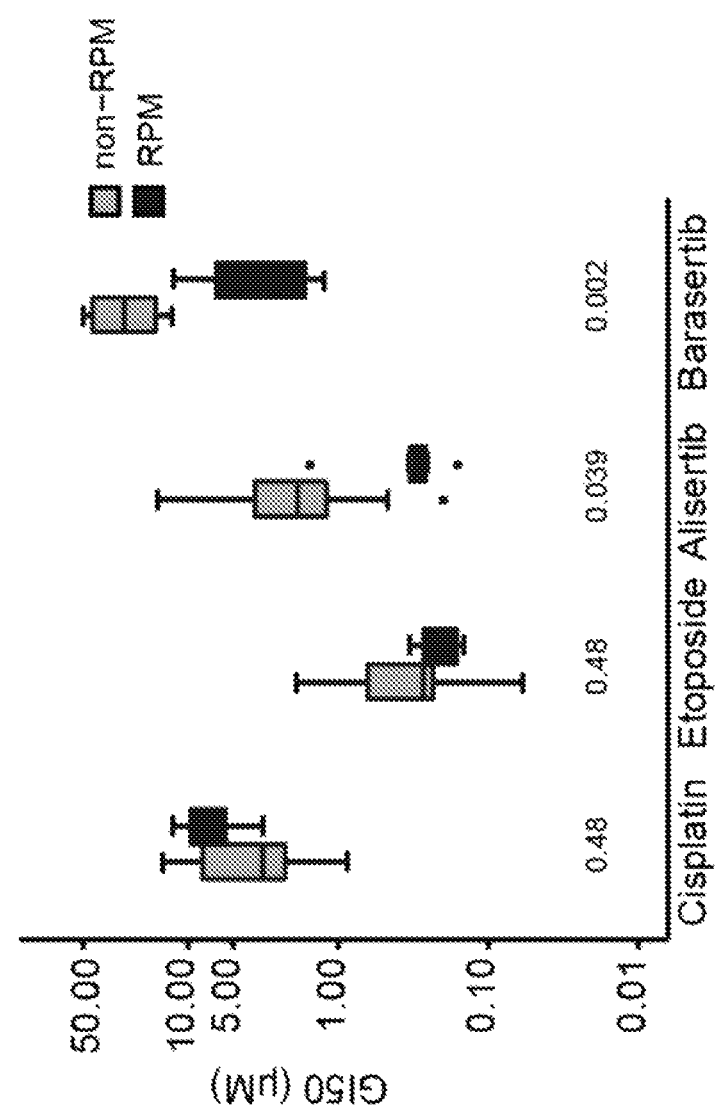
Figure 6H:
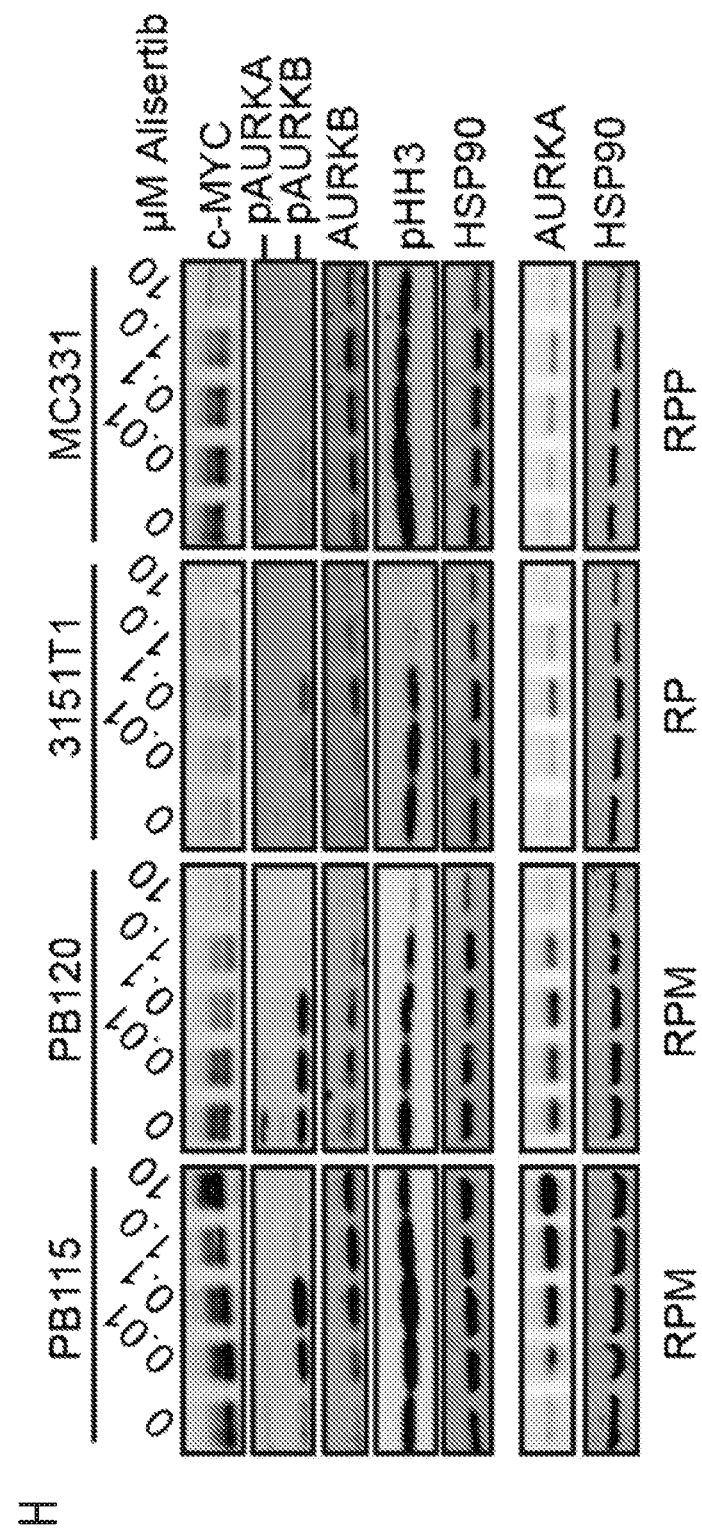
Figure 6I:
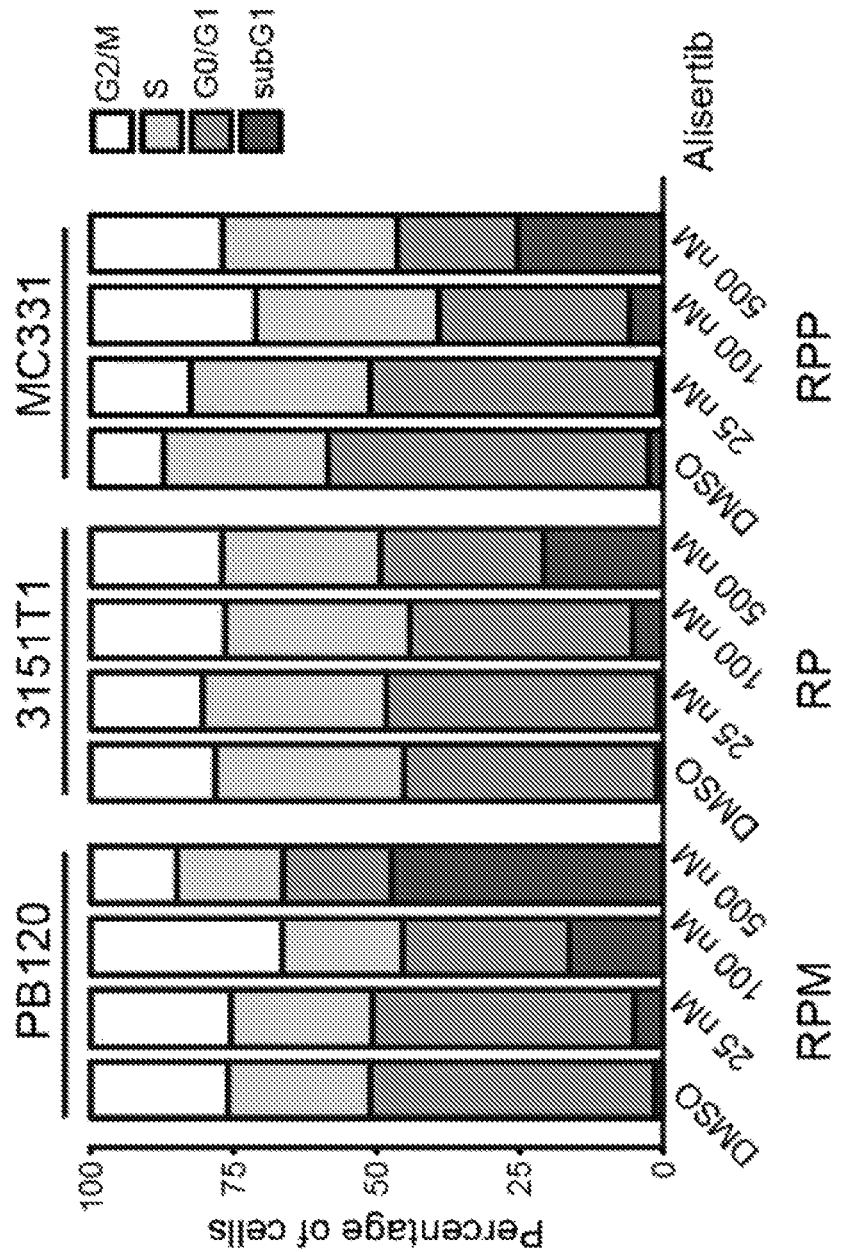
FIG. 6I shows the DNA content of PB120 (RPM), 3151T1 (RP) and MC331 (RPP) mouse cell lines treated with alisertib (48 hr) measured by flow cytometry, representative of n=2 experiments. See also FIG. 11.
Figure 11A:
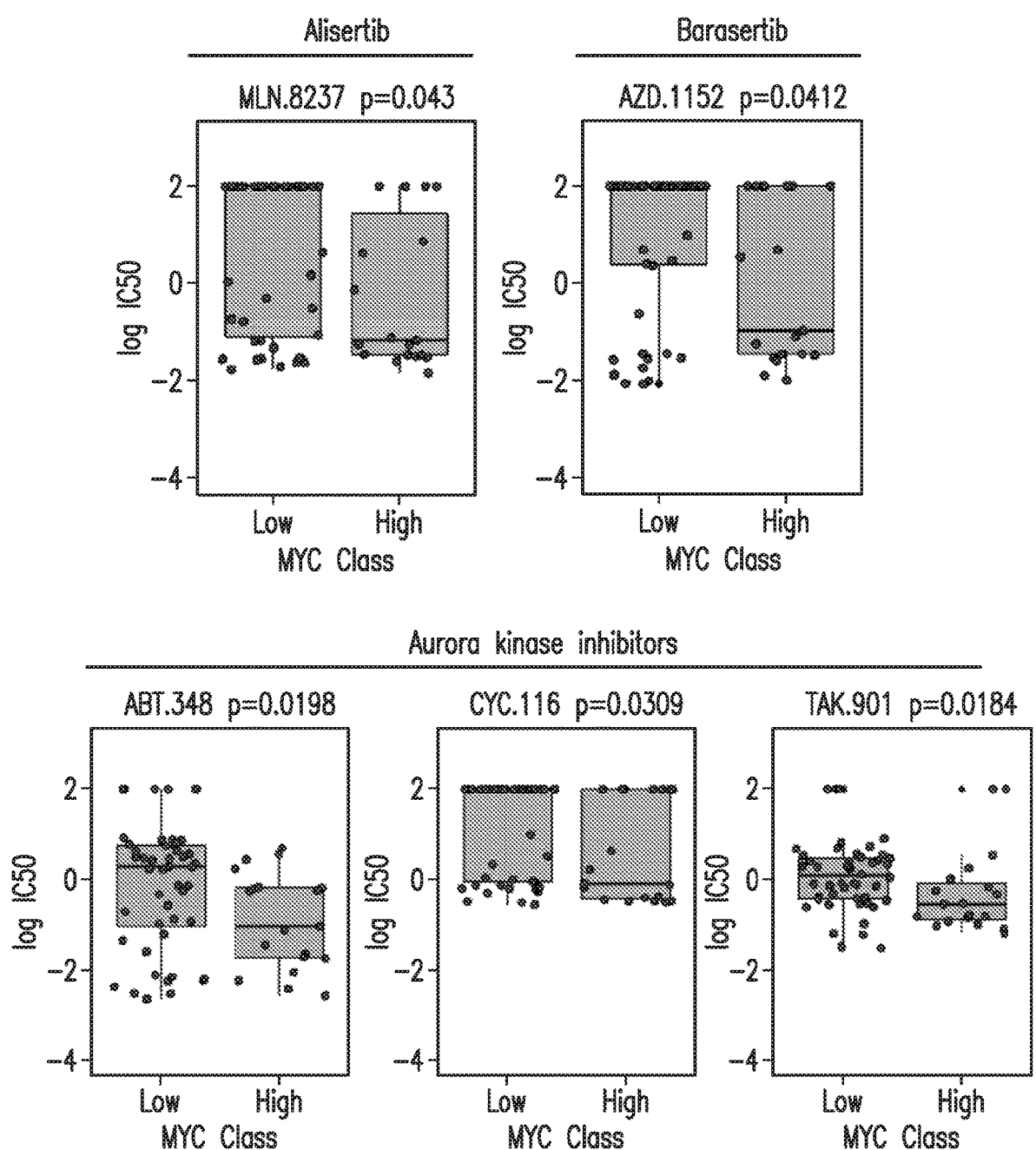
FIGS. 11A-I shows that Myc-driven SCLC is vulnerable to Aurora kinase inhibition.
Figure 11B:
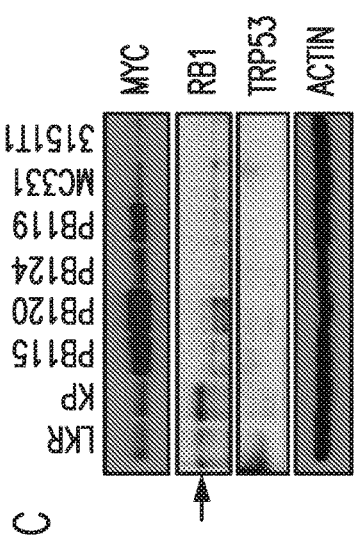
Figure 11C:
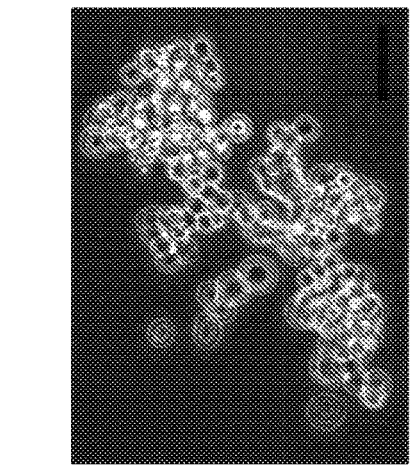
Figure 11D:
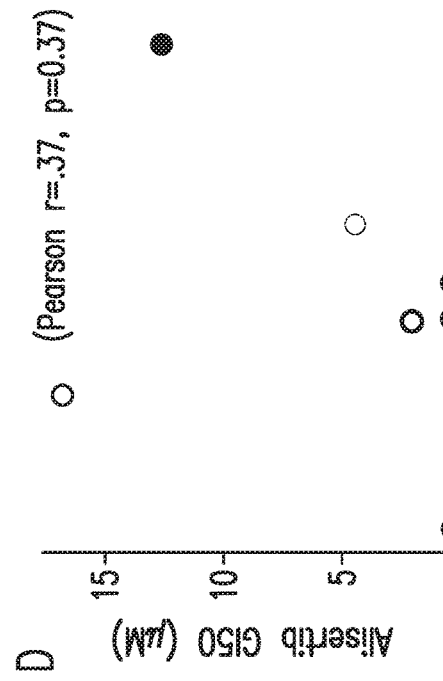
Figure 11E:
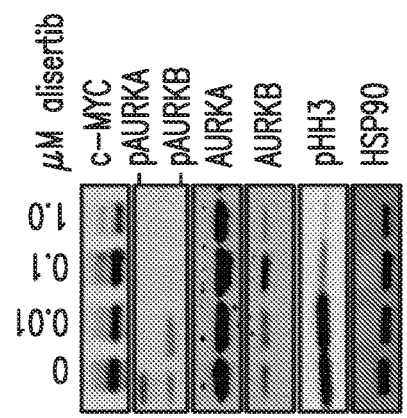
Figure 11F:
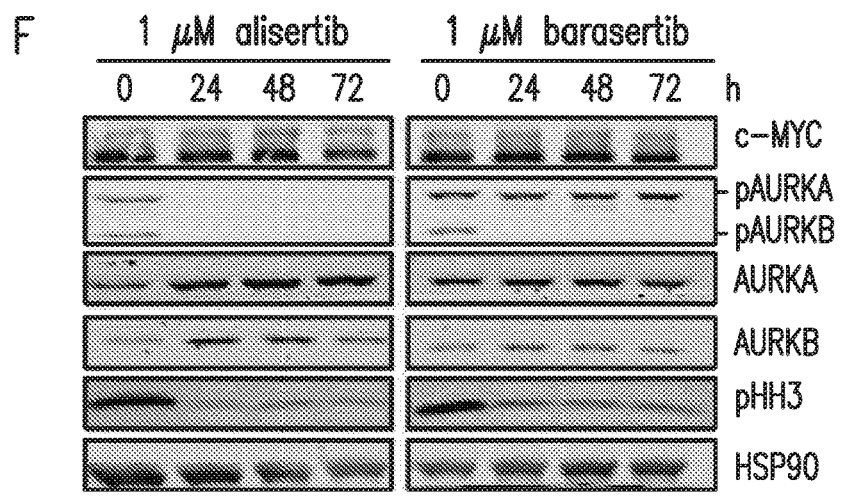
Figure 11G:
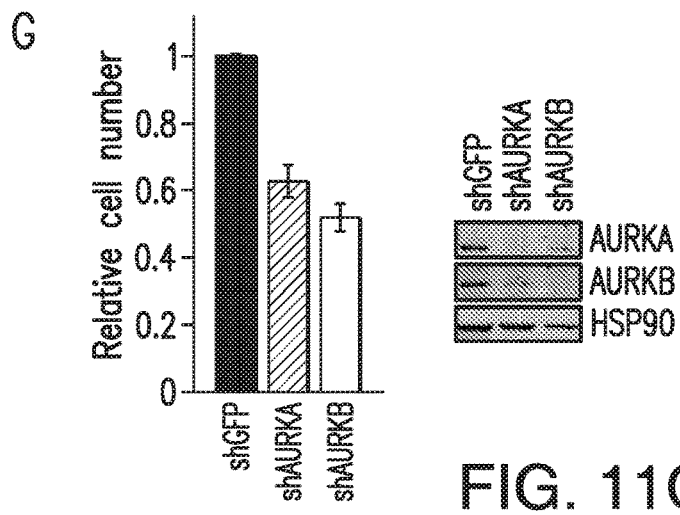
Figure 11H:
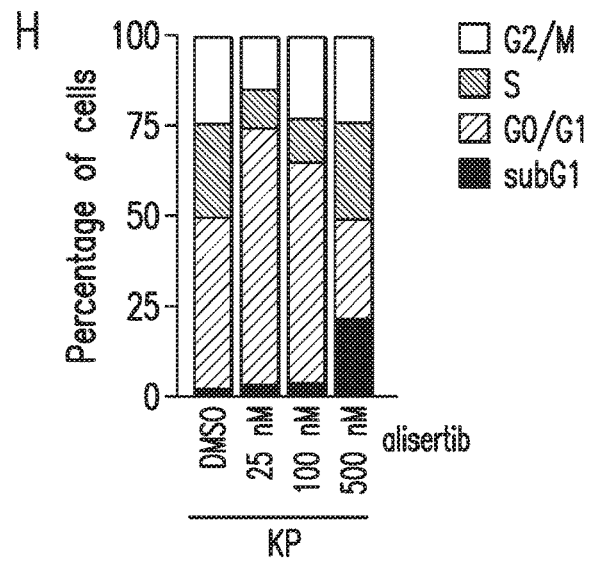
Figure 11I:
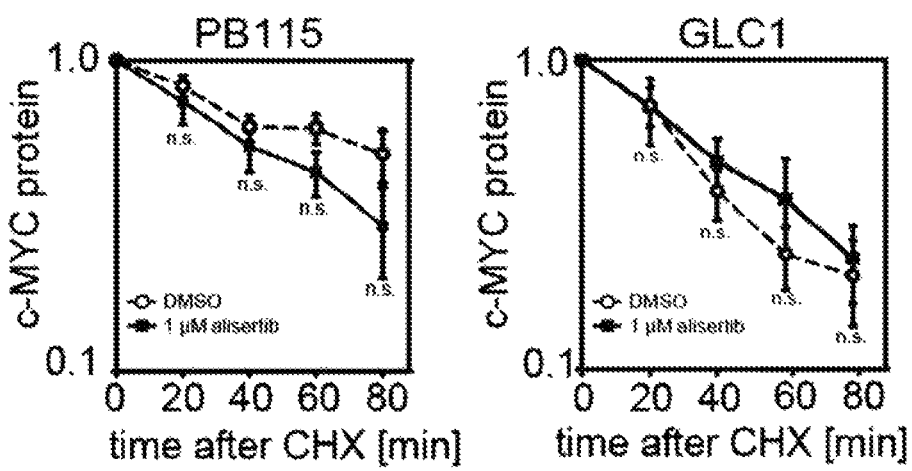
Figure 11I:
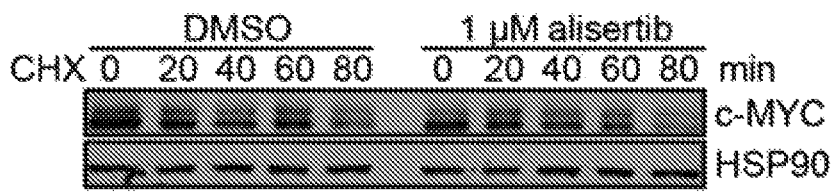
Figure 11I:

Despite numerous efforts, MYC remains difficult to target with small molecules. However, a number of synthetic lethal targets have been identified in MYC-driven tumors that may provide therapeutically exploitable vulnerabilities in these patients (Brockmann et al., 2013; Bunn et al., 2016; Sos et al., 2012; Toyoshima et al., 2012; Yang et al., 2010). To assess the efficacy of drugs that inhibit such candidate synthetic lethal targets, the activity of etoposide, cisplatin, PF-670462 (CKIε inhibitor), MS436 (BRD4 inhibitor), alisertib (Aurora A inhibitor), barasertib (Aurora B inhibitor) and milciclib (CDK2 inhibitor) was profiled across 17 human SCLC cell lines (FIG. 6A). MYC-driven SCLCs, but not those driven by MYCL or MYCN, were significantly more responsive to etoposide (adjusted p=0.038), alisertib (p=0.001) and barasertib (p=0.022) (FIGS. 6A and 6B). Also, a recently published drug screen including 68 human SCLC cell lines was analyzed by binning cells based on high or low MYC expression (Polley et al., 2016). Again, alisertib, barasertib and multiple other Aurora kinase inhibitors exhibited increased efficacy in MYC-high cell lines (FIG. 11A). Next, mouse cell lines were generated from RPM tumors including five from RPM mice and two from $RPM^{LSL/+}$ mice. Cells grew largely in suspension, often in loose aggregates or clusters similar to human variant SCLC cell lines (FIG. 11B). RPM cell lines expressed high levels of MYC and did not express RB1 or TRP53 (FIG. 11C). Next, RPM (n=7), RPP (n=3), RP (n=3) and KP (n=2) cell lines were treated with cisplatin, etoposide, alisertib or barasertib. RPM cells exhibited high micromolar $GI_{50}$ in response to cisplatin, but were sensitive to etoposide at nanomolar concentrations (FIGS. 6C and 6D). RPM cells were particularly sensitive to alisertib and barasertib when compared to adenocarcinoma cell lines and non-MYC-driven cells (FIGS. 6E-G). RPM cells tended to have a shorter doubling time, but there was not a significant correlation between doubling time and alisertib sensitivity (FIG. 11D). In other words, proliferation rate and alisertib sensitivity are not significantly correlated. Alisertib treatment resulted in dose-dependent inhibition of AURKA and AURKB at concentrations in the range of the determined $GI_{50}$-value in mouse and human cells, while barasertib was specific for AURKB (FIGS. 6H and 11E and 11F). In MYC-amplified GLC2 cells, a stronger reduction of viability after knockdown of AURKB was observed when compared to AURKA implying that inhibition of AURKB may play a role in the reduced viability of alisertib-treated cells (FIG. 11G) (Sos et al., 2012). In RPM cells, alisertib caused a dose-dependent increase in G2/M phase cells followed by an increase in subG1 cells, suggesting that cells fail to properly exit mitosis and die thereafter (FIG. 6I). Compared to KP, RPP and RP cells, RPM cells exhibited a greater increase in subG1 cells following alisertib treatment (FIGS. 6I and 11H). In contrast to described mechanisms of Aurora kinase inhibition in other malignancies (Brockmann et al., 2013; Otto et al., 2009), alisertib treatment did not primarily lead to reduced MYC protein in mouse or human cells (FIGS. 6H and 11E and F) even after cycloheximide-induced block of protein synthesis (FIG. 11I). As expected, MYC was more stable in mouse cells expressing the $MYC^{T58A}$ allele (PB115), when compared to MYC' cells (GLC1) (FIG. 11I). However, in both cell lines, a robust decrease of MYC after alisertib treatment compared to control cells was not observed, suggesting that $MYC^{T58A}$ likely does not alter the mechanistic basis of alisertib sensitivity (FIG. 11I). This suggests that MYC-driven SCLC is sensitive to Aurora kinase inhibition in mouse and human cells independent of proliferation rate and its impact on MYC levels.

Protein stability cycloheximide (CHX) experiments. Assaying c-Myc stability upon alisertib treatment was performed essentially as described in (Brockmann et al., 2013). Cells were treated with 1 µM alisertib or 0.1% DMSO for 24 hr prior to the shut-off. Cycloheximide was added to a final concentration of 100 µg/ml at the indicated time points. Protein lysates were prepared using RIPA buffer as described above, separated on 4-20% Tris-glycine gels (Invitrogen), and analyzed by immunoblot against Myc and Hsp90. Signals were quantified using Li-Cor Image Studio (Li-Cor Biosciences) and ratios of Myc/Hsp90 normalized to the 0 min time point. Graphs depict the average normalized Myc/Hsp90 ratios of three independent experiments with SEM.

Methods and materials used are described herein and above.

Example 7: Aurora Kinase Inhibition Significantly Improves Chemotherapy Response of Myc-Driven SCLC To determine the efficacy of alisertib in vivo, RPM mice were imaged by microCT and upon detection of tumors, randomly assigned to receive either vehicle control (PBS), 5 mg/kg cisplatin and 10 mg/kg etoposide (once weekly), 20 mg/kg alisertib (twice daily, 5 days on, 2 days off), or chemotherapy plus alisertib (FIG. 7A). Mice were monitored by microCT imaging immediately before treatment and four days after each cisplatin treatment for up to 20 days.

Figure 7C:
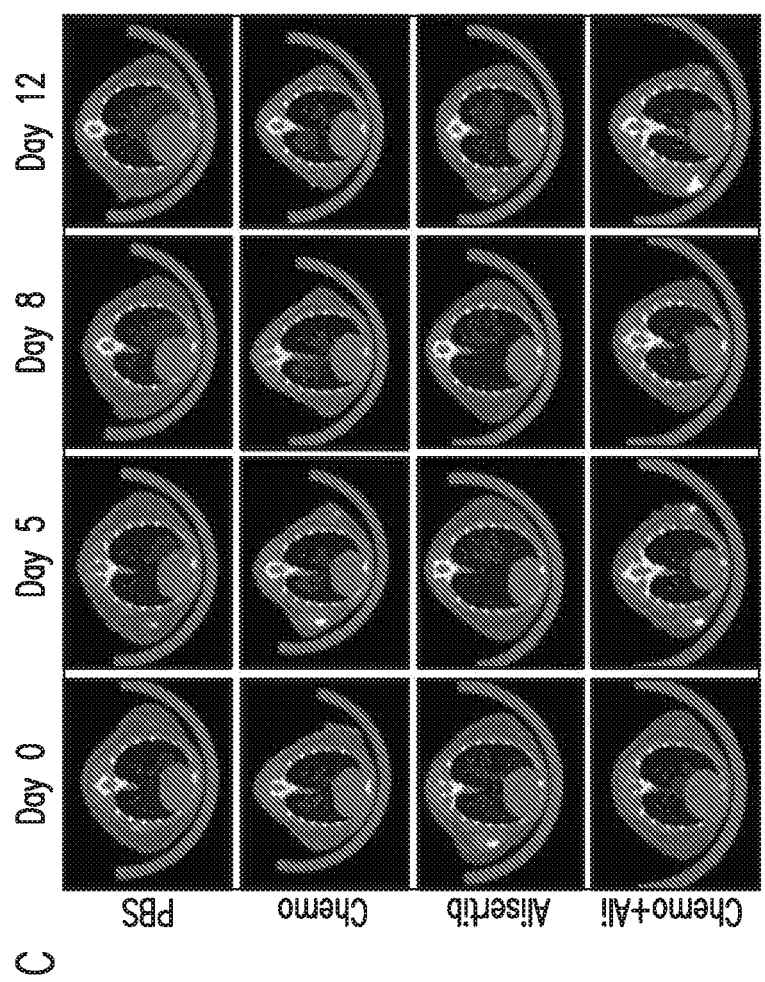
Figure 7D:
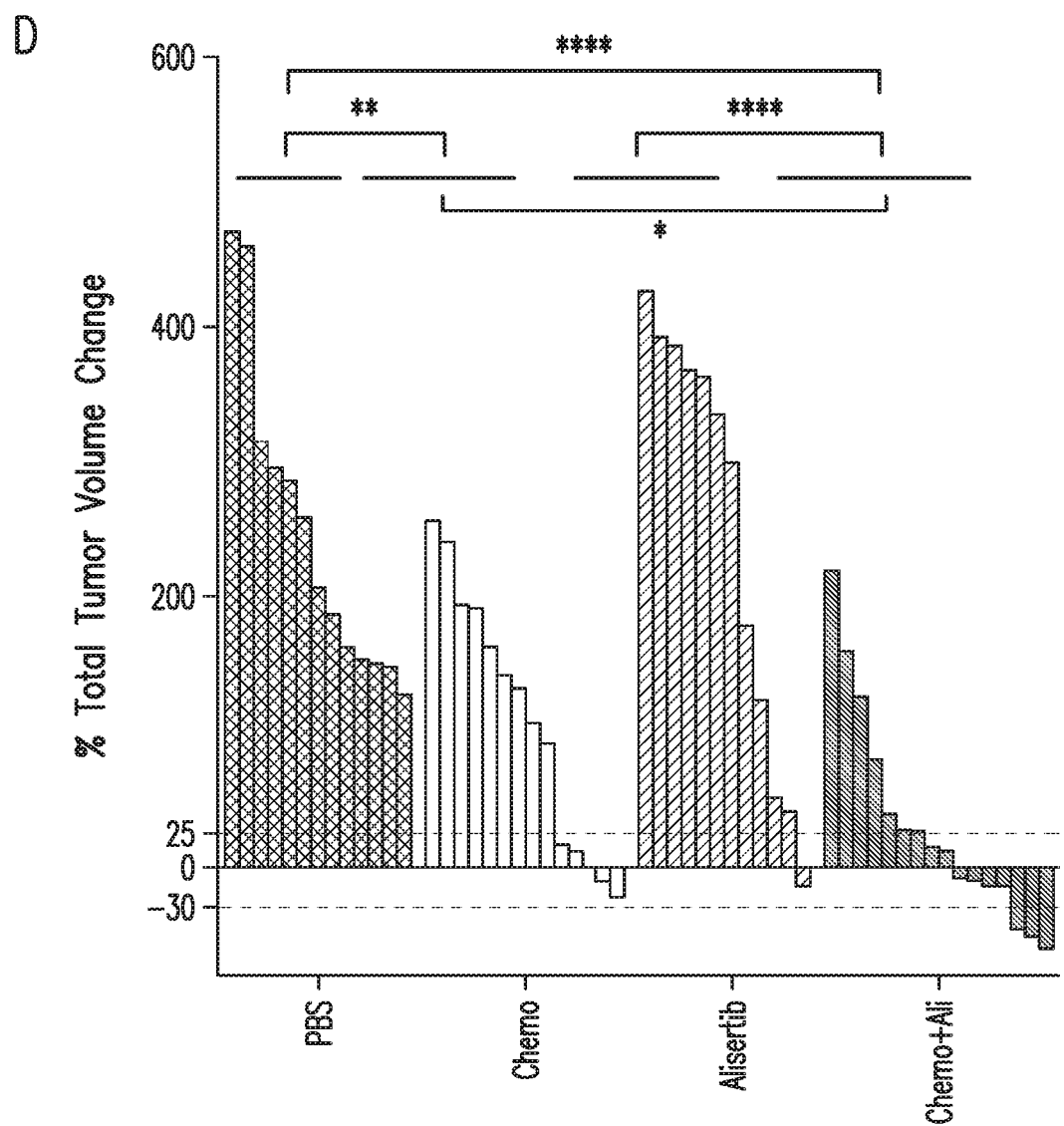
Figure 12A:
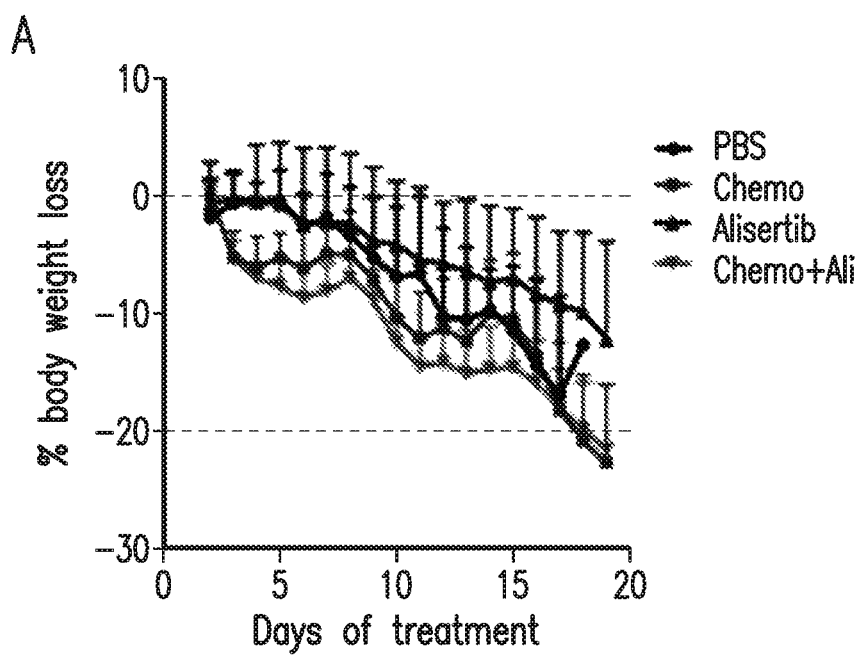
FIGS. 12A-D show that Aurora kinase inhibition combined with chemotherapy significantly prolongs survival of mice with Myc-driven SCLC.
Figure 12B:
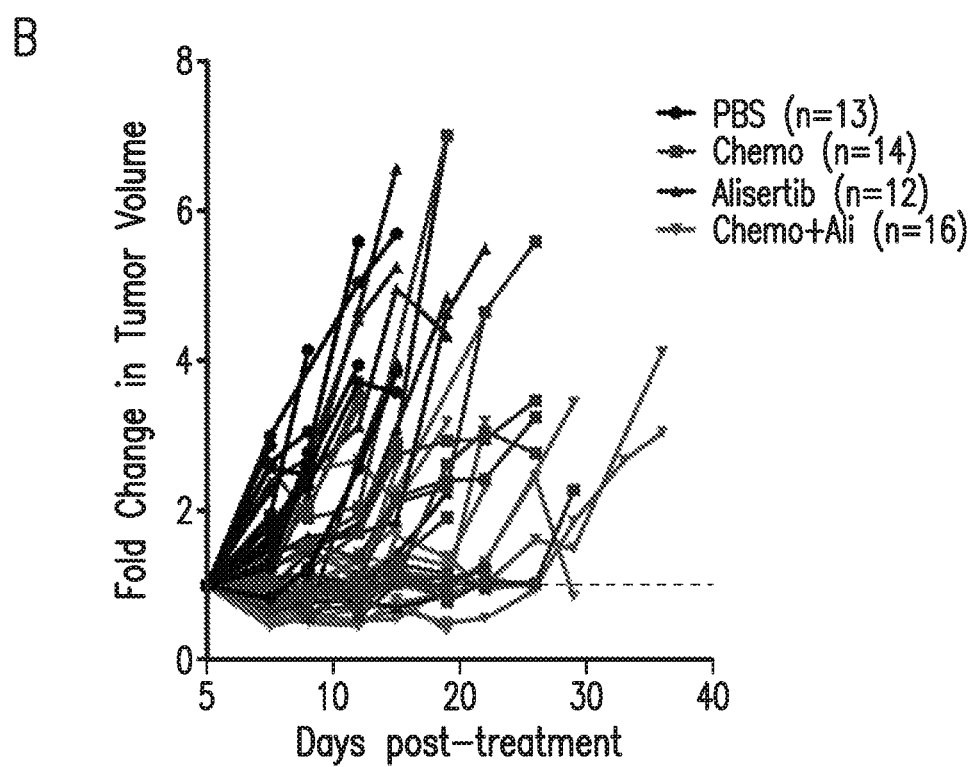
Figure 12C:
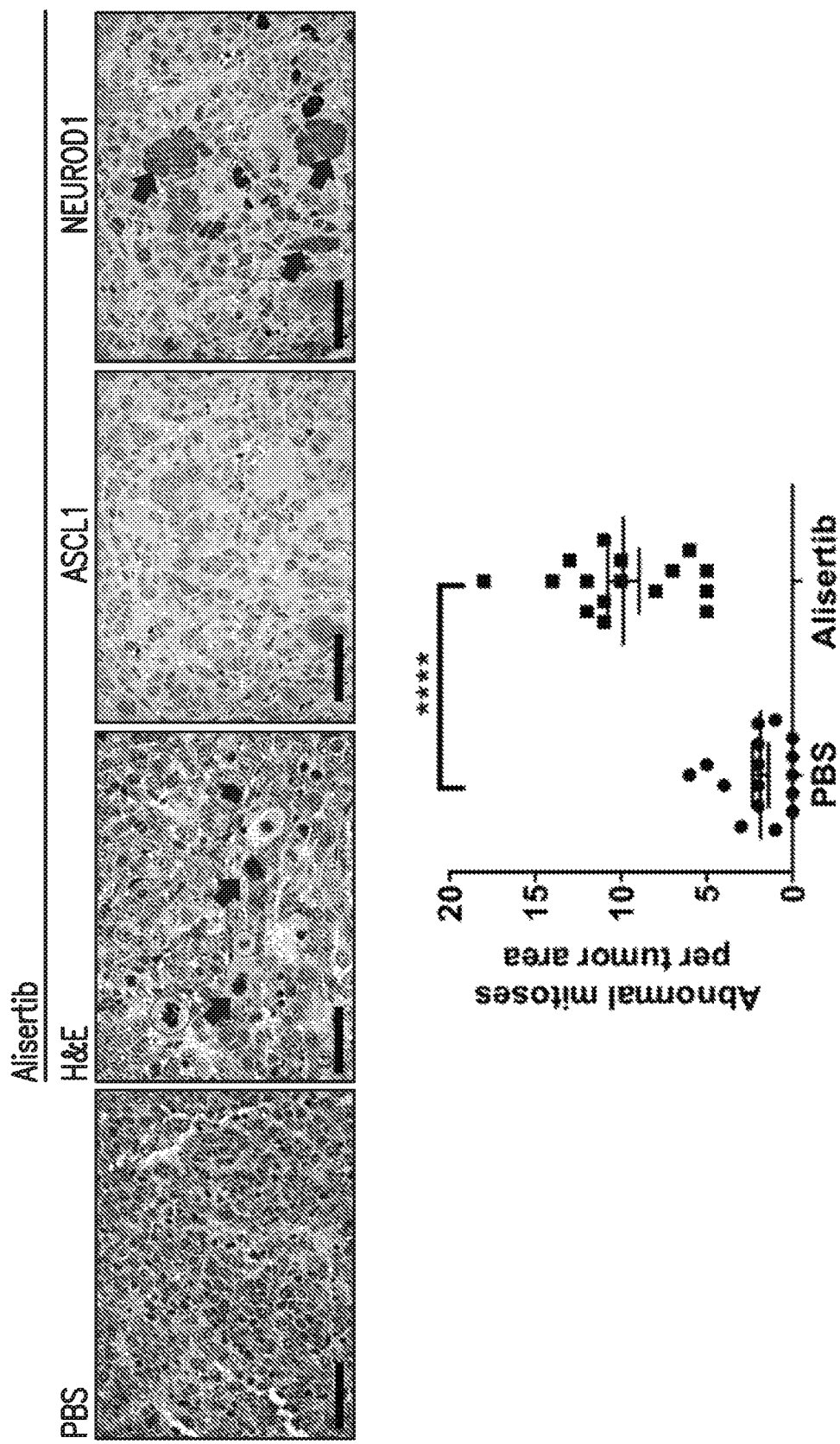
Figure 12D:
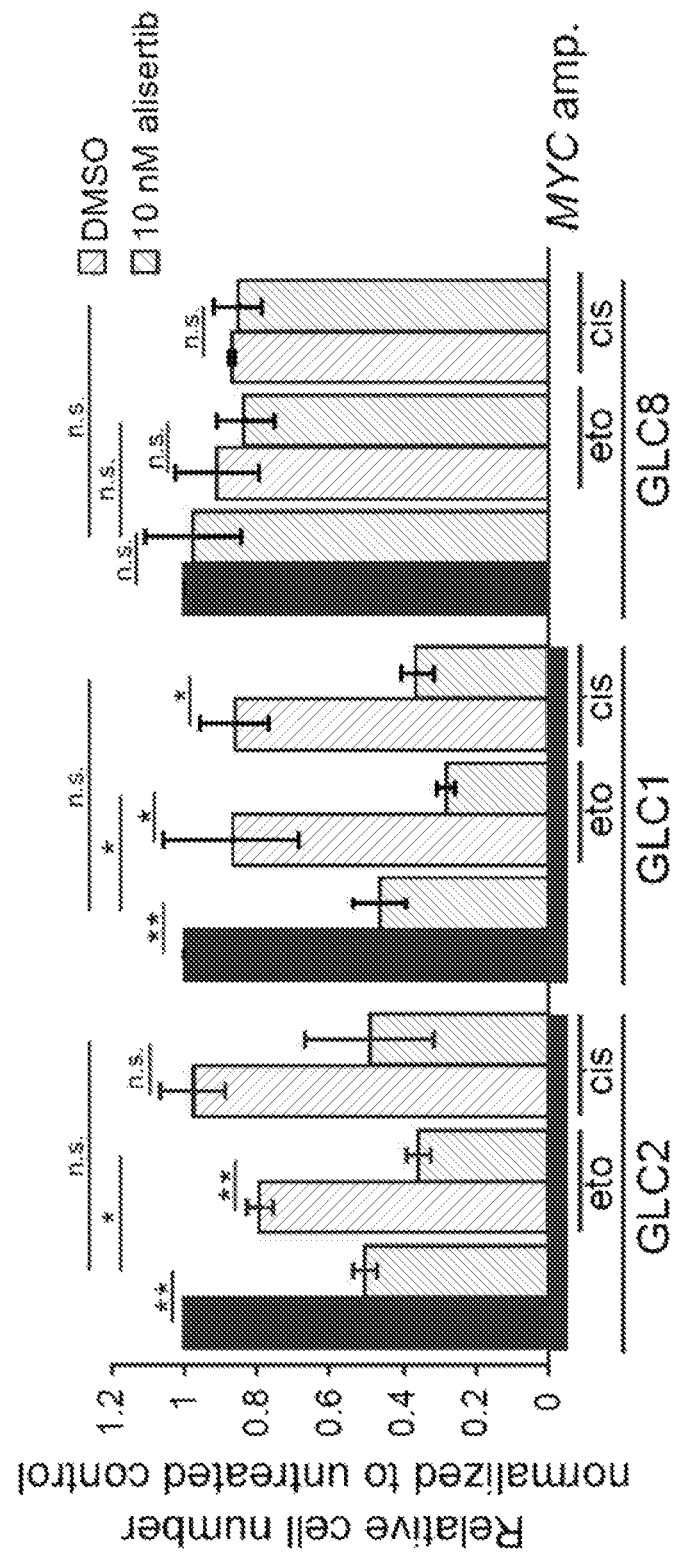

Weight loss upon alisertib treatment did not differ from PBS control-treated animals but regimens with chemotherapy caused ~15-20% weight loss such that one animal in each treatment group required sacrifice due to toxicity (FIG. 12A). Total tumor volume was quantified relative to total air volume as a comprehensive measurement of treatment impact. PBS-treated animals survived an average of 12 days following tumor detection due to rapid tumor growth (FIGS. 7B, 7C and 12B). Alisertib-treated animals exhibited a modest delay in tumor growth, which was largely attributable to its impact at early time points. The majority of chemotherapy-treated animals completed three cycles of therapy with significantly delayed tumor growth (FIGS. 7B, 7C and 12B). Strikingly, animals treated with a combination of alisertib and chemotherapy exhibited complete tumor stasis over three cycles of treatment (FIGS. 7B, 7C and 12B). The percent change in total tumor volume was analyzed at Day 19 (or at the time of death, if sooner) compared to Day 0 in each treatment group by waterfall plot. Despite the initial delay in tumor growth, alisertib alone did not impact overall response compared to untreated animals in this time frame (FIG. 7D). Of animals treated with chemotherapy, 5 of 14 experienced stable disease while the majority of animals (n=9 of 14) progressed during treatment. Remarkably, the majority of animals treated with chemotherapy and alisertib (n=10 of 16) exhibited stable disease including three animals with >30% reduction in tumor volume (FIG. 7D). Although the effect of alisertib treatment was more pronounced in vitro, the combination of alisertib with etoposide, but not cisplatin, further decreased cell viability in MYC-amplified cells (FIG. 12D).

Figure 7E:
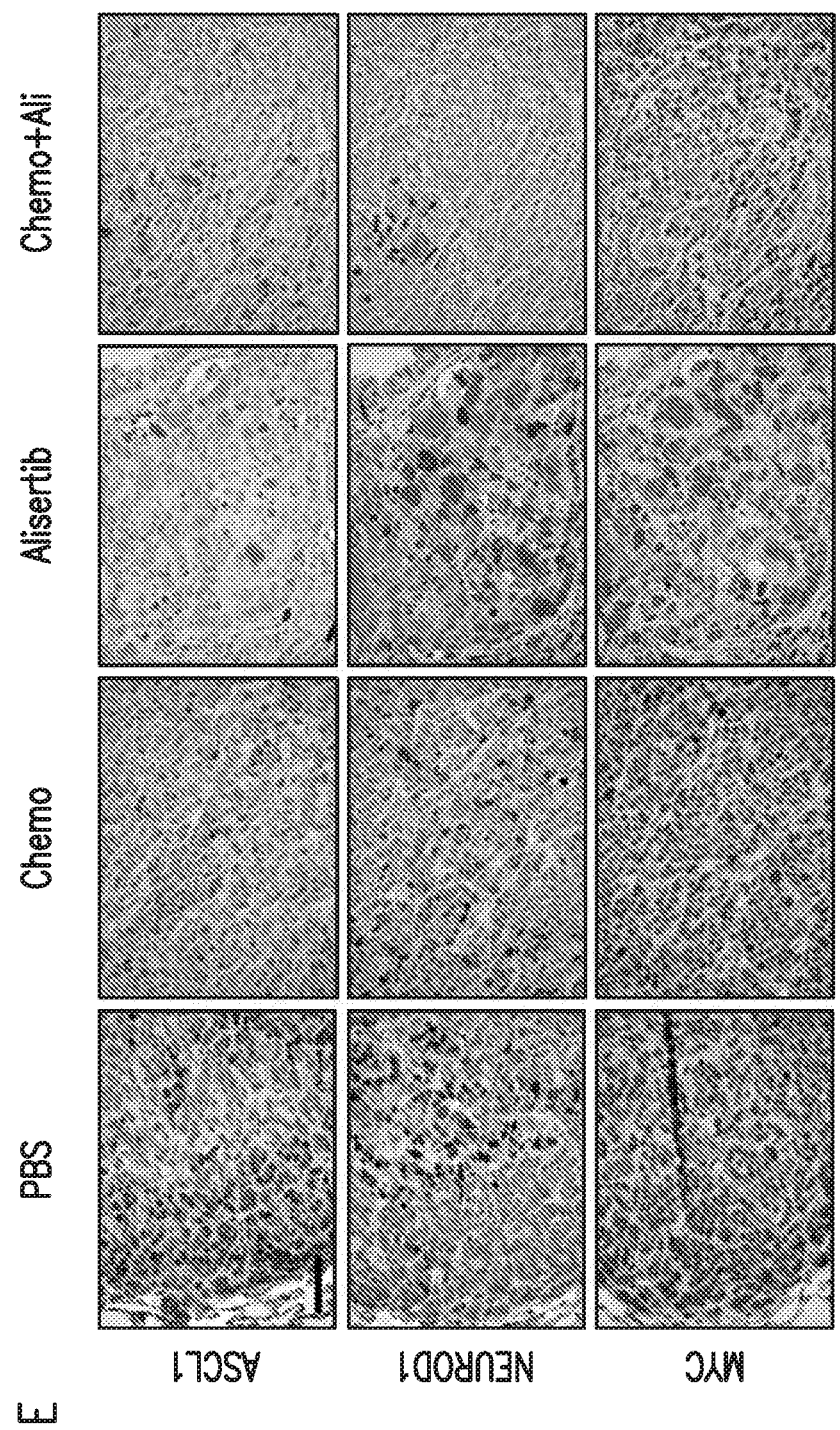
Figure 7F:
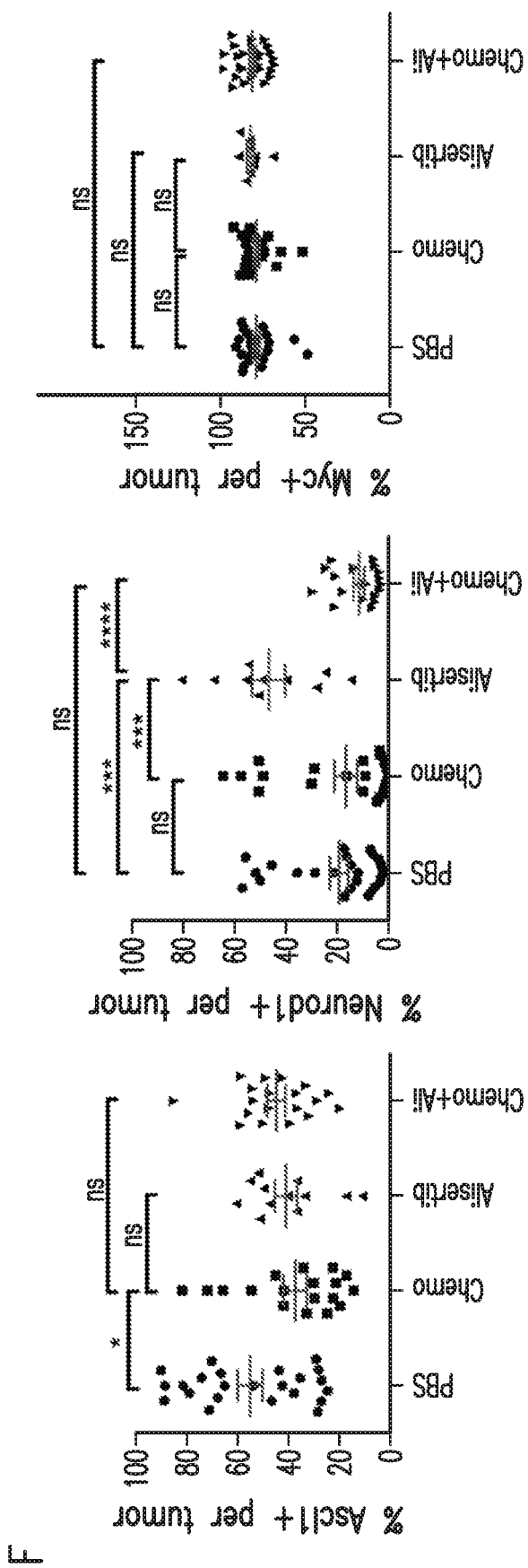

Given the heterogeneity in classic and variant cells in the RPM model, the next set of experiments were carried out to determine whether these treatments impact ASCL1, NEUROD1 or MYC levels in vivo. Interestingly, chemotherapy led to a reduction in ASCL1 levels, suggesting that the classic or early stage lesions may be more chemo-sensitive in this model (FIGS. 7E and F). Most strikingly, alisertib treatment led to a dramatic enrichment of cells with polyploidy and aberrant mitoses (FIG. 12C) consistent with its mechanism of action (Wilkinson et al., 2007). These abnormal cells were NEUROD1+ and significantly enriched in alisertib-treated animals compared to other treatment groups (FIGS. 7E, 7F and 12C). The combination of alisertib with chemotherapy, however, did not lead to an enrichment in NEUROD1+ cells, suggesting that chemotherapy may have contributed to the depletion of these large aberrant cells.

Figure 7G:
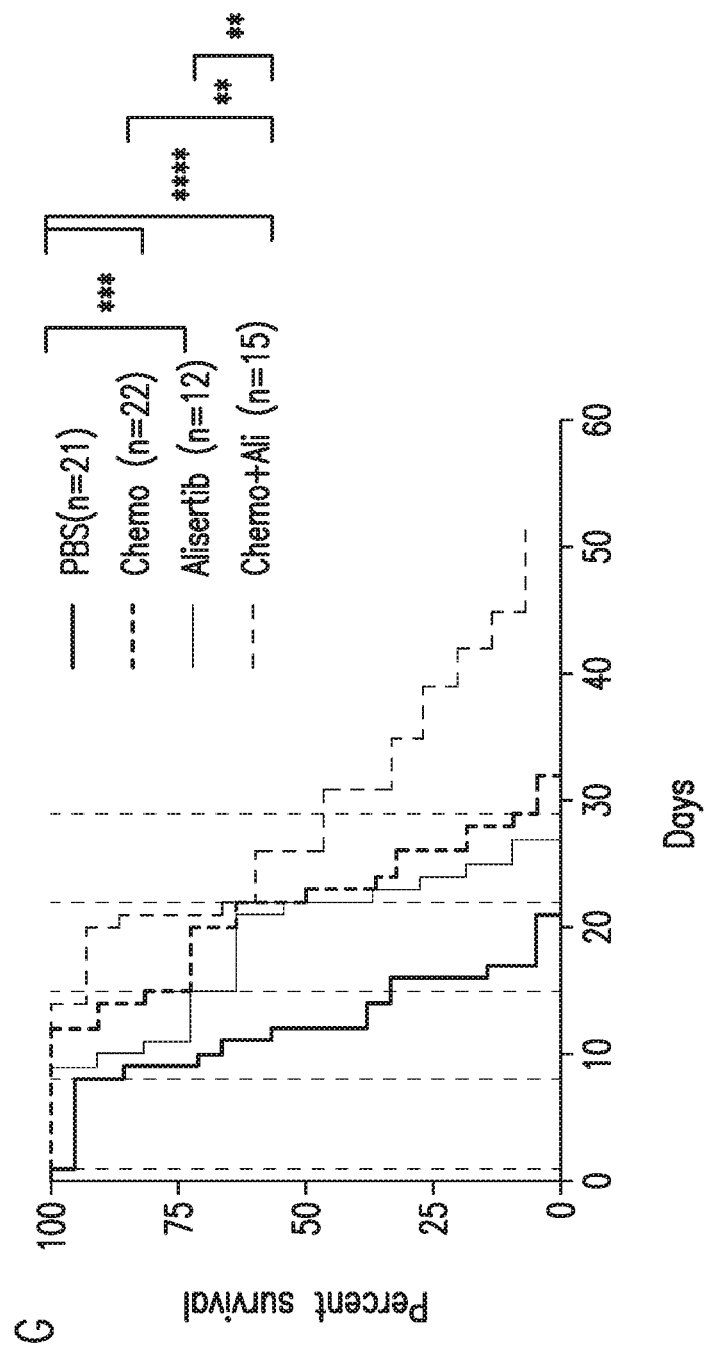

Despite the modest delay in tumor growth, alisertib treatment increased median survival by 10 days compared to untreated animals, comparable to chemotherapy, which increased survival by 11 days (FIG. 7G). The combination of chemotherapy with alisertib increased median survival by 14 days compared to untreated mice, and was significantly more efficacious than either alisertib or chemotherapy alone. Importantly, 47% of combination-treated mice survived 30 days compared to 0%, 5%, and 8% of the PBS, chemo- or alisertib-treated animals (Fisher's exact test p=0.0008, 0.0032, and 0.0433, respectively). Together, these results suggest that alisertib, with chemotherapy, in first-line treatment of MYC-driven SCLC halts tumor growth and significantly extends survival compared to the standard-of-care chemotherapy.

MYC-driven tumors, including SCLCs, exhibit synthetic lethality with Aurora kinase inhibition, but this had not been explored in SCLC GEMMs in vivo (Brockmann et al., 2013; Gustafson et al., 2014; Hook et al., 2012; Otto et al., 2009; Sos et al., 2012; Yang et al., 2010). The data disclosed herein suggest that MYC expression sensitizes SCLC to Aurora kinase inhibition particularly in combination with chemotherapy, which significantly improved tumor control and prolonged survival compared to chemotherapy alone. Alisertib monotherapy had modest impact in vivo, but it remains possible that an optimized dosing regimen could improve this response. Recent clinical trials in relapsed SCLC tested alisertib monotherapy with ~20% of patients exhibiting partial responses (Melichar et al., 2015) while a pan-Aurora kinase inhibitor had no responses in a small number of relapsed patients (Schoffski et al., 2015). Current clinical trials are assessing alisertib in combination with chemotherapy as a second-line therapy (NCT02038647). The data presented herein predict that MYC levels, neuroendocrine-low or variant histopathology may serve as biomarkers for alisertib sensitivity in patients. Finally, these data suggest that Aurora kinase inhibition can improve chemotherapy response in vivo, suggesting that patients with MYC-amplified SCLCs may benefit from first-line Aurora kinase inhibitors in combination with standard chemotherapy. Together these findings challenge the current classification of SCLC as a homogeneous disease and suggest that distinct subtypes of SCLC exist with specific vulnerabilities to targeted therapies that are poised to improve patient outcomes.

Example 8: MYC Expression Inversely Correlates to BCL2 Expression

Figure 13:
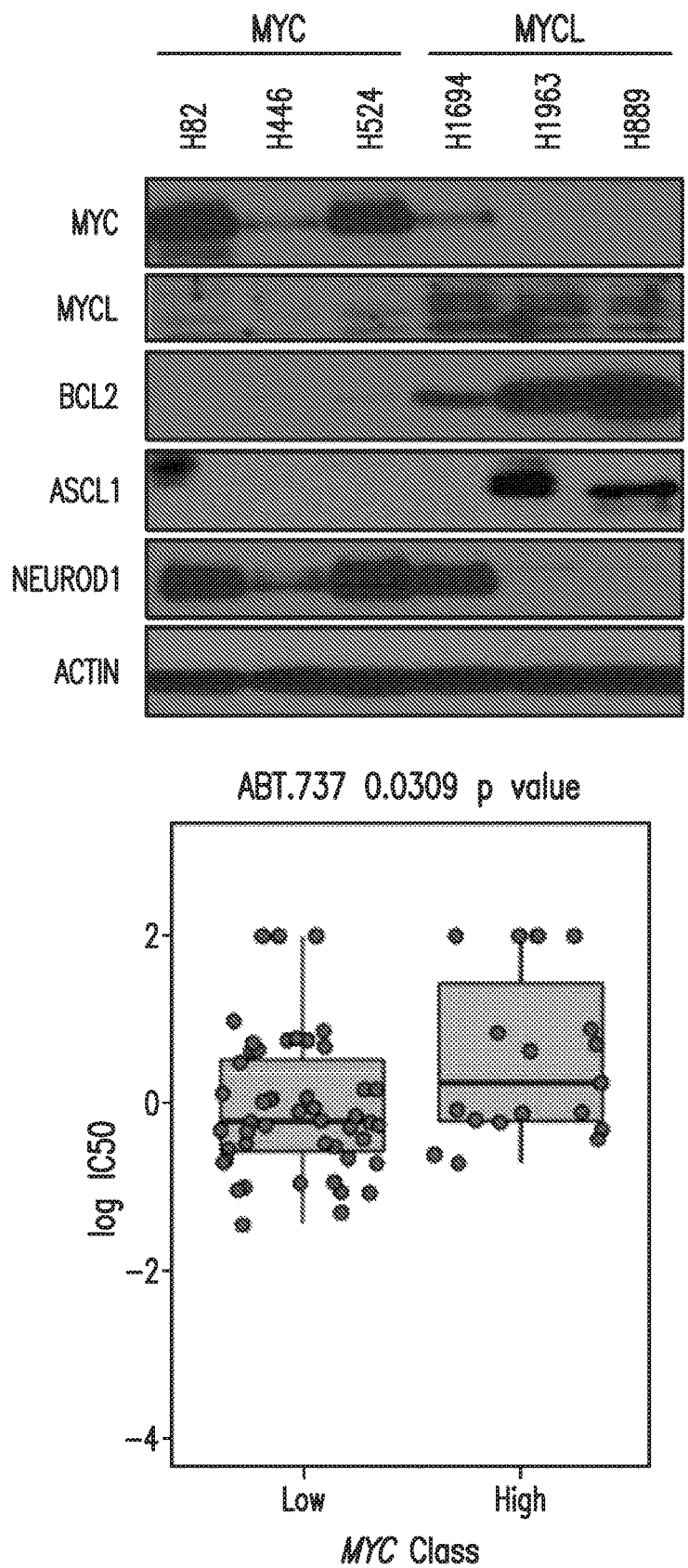
FIG. 13 shows that MYC expression anti-correlates with BCL2 expression and sensitivity to BCL2 inhibition.
Figure 13:
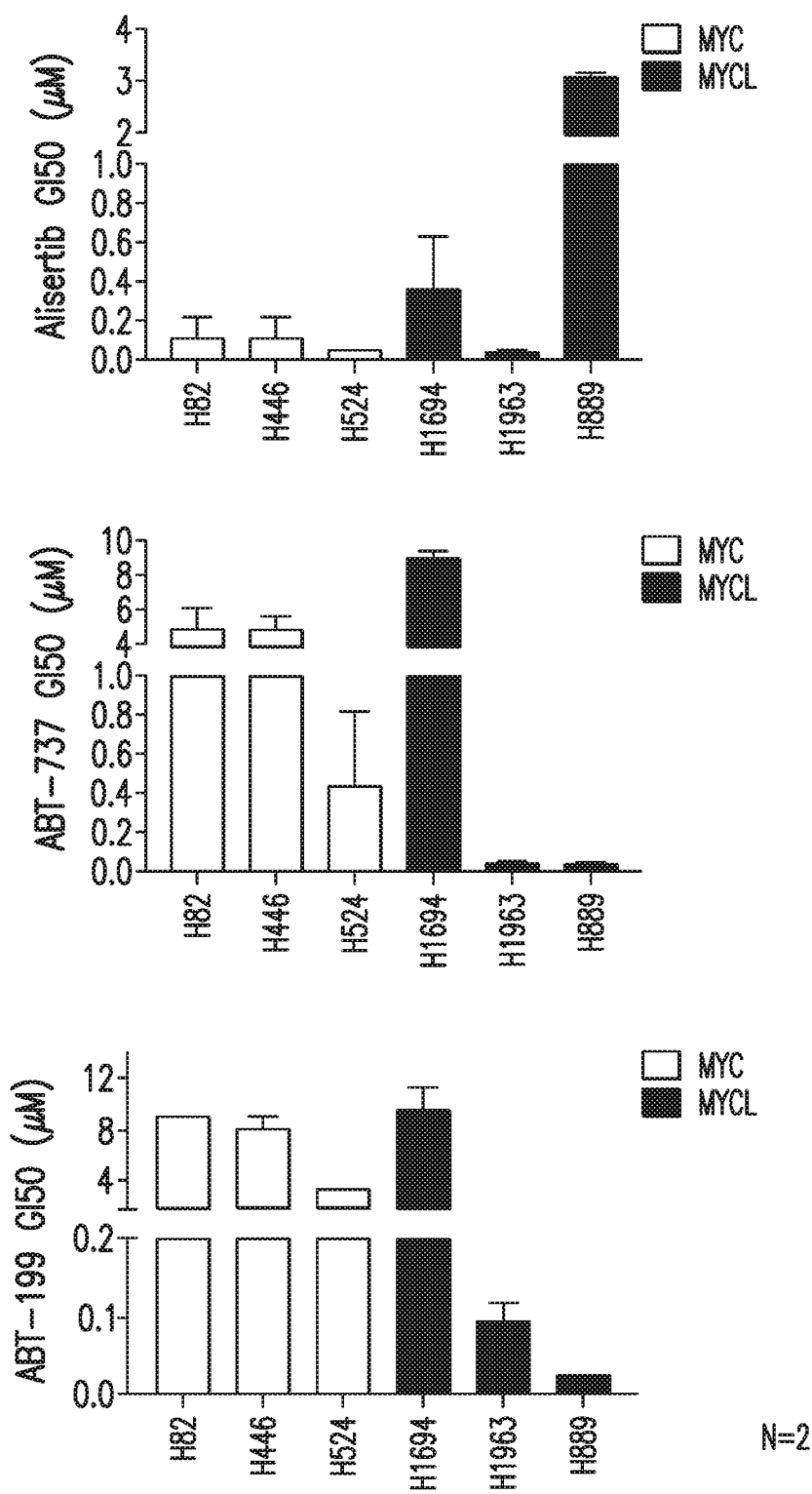

Whole cell lysates from human cell lines were prepared using RIPA buffer supplemented with protease inhibitors (Roche complete mini) and benzonase (Millipore)), separated on Tris-glycine SDS-PAGE gels, and transferred to PVDF membrane (Millipore). Membranes were blocked for 1 hr in 5% milk or 5% BSA in TBS with 0.01% tween 20 (TBS-T), followed by overnight incubation with primary antibodies at 4° C. Membranes were washed for 6×5 min at room temperature in TBS-T. Mouse and rabbit HRP-conjugated secondary antibodies (Jackson ImmunoResearch, 1:10,000) were incubated for 1 hr at room temperature followed by washing 6×5 min at room temperature in TBS-T. For detection (see, FIG. 13), membranes were exposed to WesternBright HRP Quantum substrate (Advansta) and detected on Hyblot CL film (Denville Scientific Inc).

Human cell lines were seeded in triplicate in white, flat-bottomed 96-well plates at 2000 cells/well. The following day, increasing doses of Alisertib (ApexBio), ABT-737 (ApexBio) or ABT-199 (ApexBIo) were added. Drug was added again at 48 h to maintain the desired final concentration. After 96h of treatment, cell viability was measured using Cell Titer Glo (CTG) assay (Promega, Madison, Wis., USA) and plates were read on a luminometer. Normalized, transformed dose response curves were generated and analyzed using GraphPad Prism (GraphPad, La Jolla, Calif., USA) to determine GI50 for each compound (see, FIG. 13). Error bars represent mean+/−SEM. These results indicate that MYC expression anti-correlates with BCL2 expression and sensitivity to BCL2 inhibition.

Figure 14:
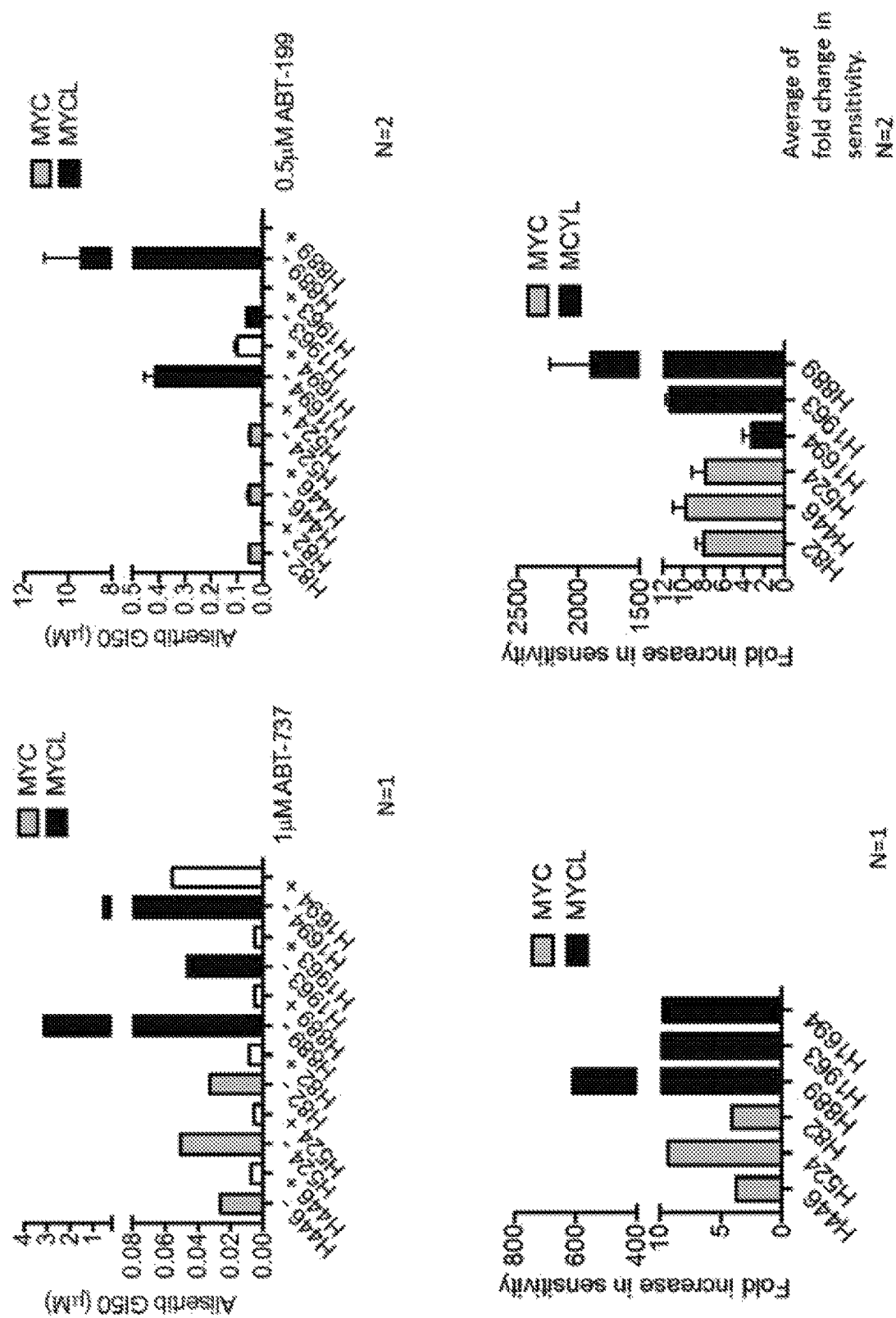
FIG. 14 shows that BCL2 inhibition increases the response to Alisertib irrespective of MYC status.

In a separate experiment, human cell lines were seeded in triplicate in white, flat-bottomed 96-well plates at 2000 cells/well. The following day, increasing doses of Alisertib (ApexBio) was added in the presence or absence of ABT-737 or ABT-199 (ApexBio). Drug was added again at 48h to maintain final concentration. After 96h of treatment, cell viability was measured using Cell Titer Glo (CTG) assay (Promega, Madison, Wis., USA) and plates were read on a luminometer. Normalized, transformed dose response curves were generated and analyzed using GraphPad Prism (GraphPad, La Jolla, Calif., USA) to determine GI50 for each compound (see, FIG. 14). Error bars represent mean+/− SEM. These results show that BCL2 inhibition increases the response to Alisertib irrespective of MYC status.

Figure 15:
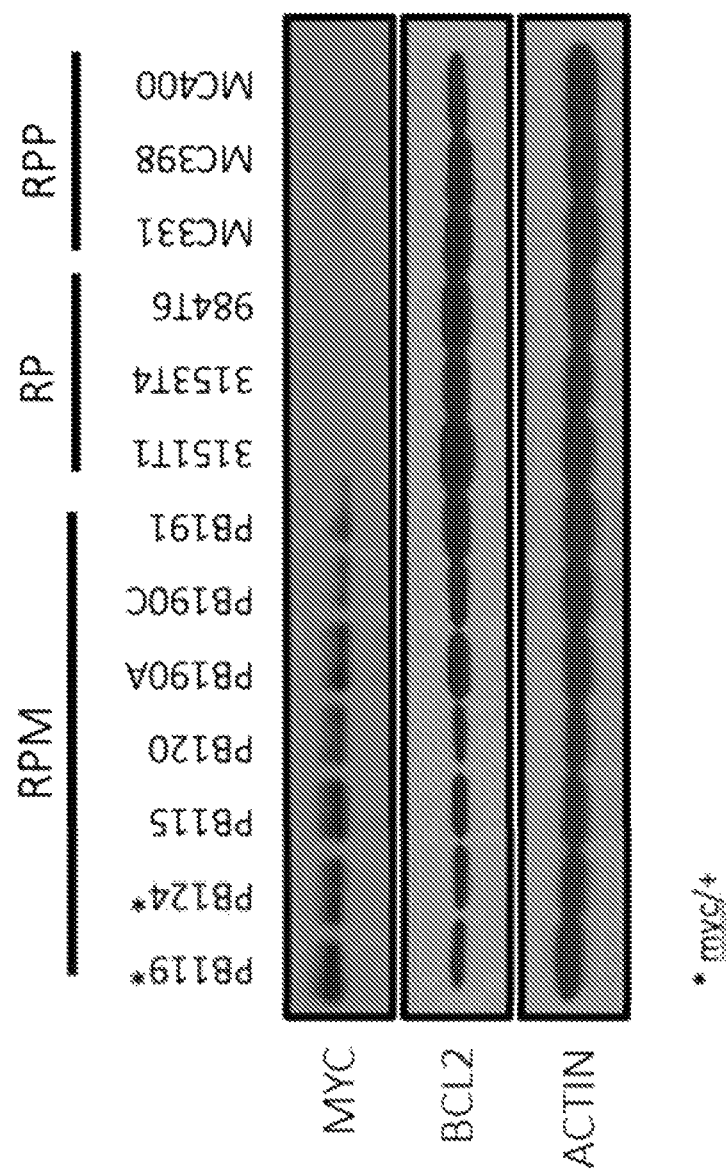
FIG. 15 shows that BCL2 expression inversely correlates with MYC in RPM mouse cell lines.
Figure 16:
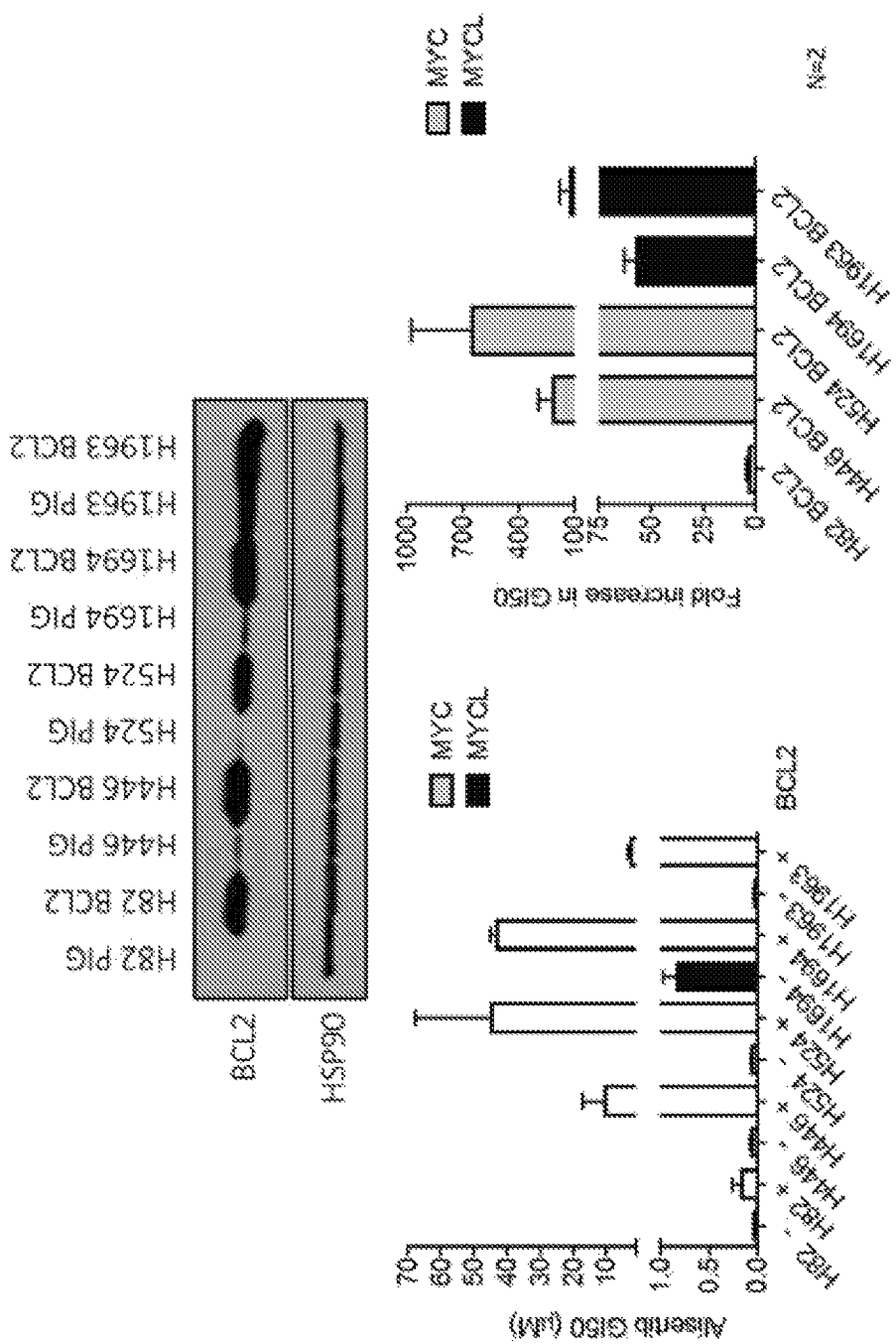
FIG. 16 shows that BCL2 over expression promotes Alisertib resistance.

FIG. 15 shows in RPM mouse cell lines, BCL2 expression inversely correlates with MYC. Mouse cell lines were derived from primary mouse tumors from indicated mouse models: RPM ($Rb^{fl/fl}$;$p53^{fl/fl}$;$Myc^{LSL/LSL}$) RP ($Rb^{fl/fl}$;$p53^{fl/fl}$) RPP ($Rb^{fl/fl}$;$p53^{fl/fl}$; $Pten^{fl/fl}$). Whole cell lysates were analyzed by SDS PAGE for the indicated proteins as previously described. ACTIN served as a loading control.

The experiments also show that BCL2 overexpression promotes Alisertib resistance. HEK293T cells were transfected with pMSCV PIG (Addgene Plasmid #21654) empty vector, or pMSCV PIG with an insert that encodes the human Bcl-2 gene in addition to pCMV-VSVG and pCMV delta R8.2 plasmids using TransIT-LT1 (Minis). Virus was collected at 48 and 72 hr post-transfection. Human SCLC cell lines were infected with viral supernatant. Infected cells were selected with puromycin for several days until all uninfected cells were killed by puromycin. Whole cell lysates were analyzed by SDS PAGE as previously described, and probed for indicated proteins. HSP90 serves as a loading control. Cell viability assays were carried out as previously described, with the addition of Alisertib +/−0.5 uM ABT-199 (ApexBio) using the infected human cell lines described above. Cell viability assays were carried out as previously described, with the addition of Alisertib +/−0.5 uM ABT-199 (ApexBio) using the infected human cell lines described above.

Figure 17:
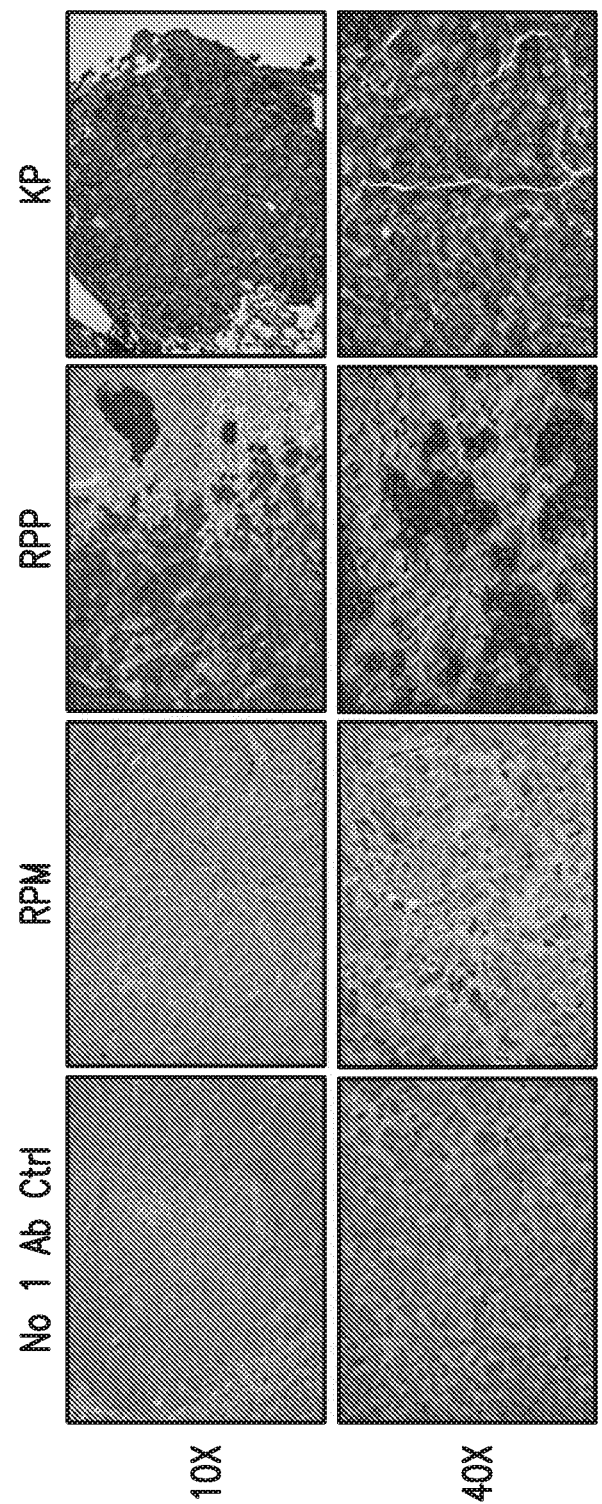
FIG. 17 shows that MYC-driven SCLC has low EPCAM expression.

Example 9: Identification of Biomarkers for Classic and Variant SCLC Using Circulating Tumor Cells and Mouse Models Lungs from RPM ($Rb^{fl/fl}$; $Trp53^{fl/fl}$; $Myc^{T58A}$), RPP ($Rb^{fl/fl}$; $Trp53^{fl/fl}$; $Pten^{fl/fl}$) and KP ($Kras^{G12D}$; $Trp53^{fl/fl}$) mice were harvested from animals when tumor burden necessitated sacrifice. Lungs were fixed in formalin and embedded in paraffin. Four µM unstained sections were dewaxed, rehydrated and subjected to high temperature antigen retrieval, 20 min boiling in a pressure cooker in 0.01 M citrate buffer, pH 6.0. Slides were blocked in 3% H202 for 15 min, blocked in 5% goat serum in PBS/0.1% Tween-20 (PBS-T) for 1 hr, and stained overnight in blocking buffer with primary antibodies. A HRP-conjugated secondary antibody (Vector Laboratories) was used at 1:200 dilution in PBS-T, incubated for 45 min at room temperature, followed by DAB staining (Vector Laboratories). All staining was performed with Sequenza coverplate technology. EPCAM primary antibody: Abcam #71916, 1:100. The results in FIG. 17 show that MYC-driven SCLC has low EPCAM expression by immunocytochemistry.

Figure 18:
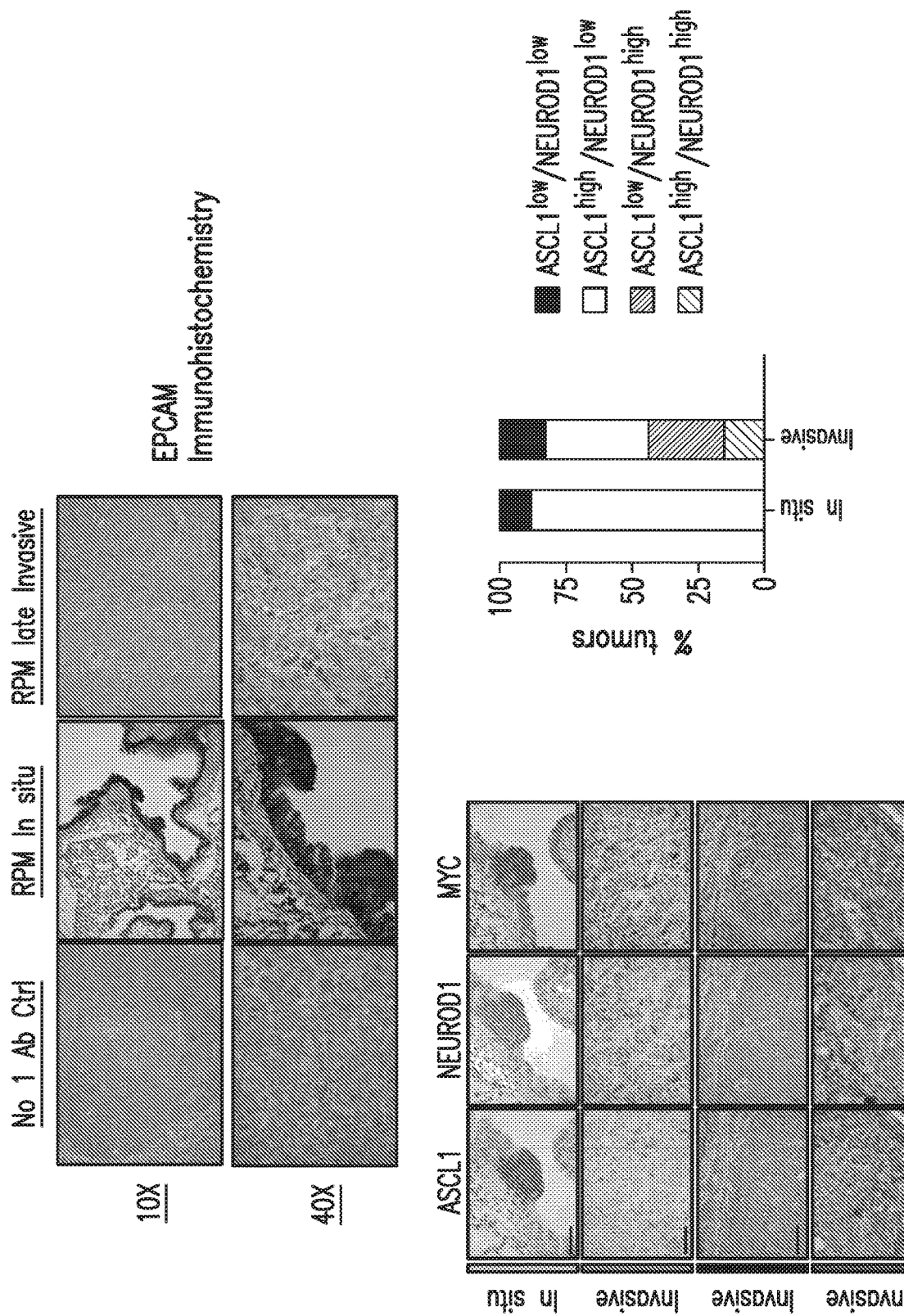
FIG. 18 shows that EPCAM expression correlates with ASCL1+ classic SCLC expression.

FIG. 18 shows that EPCAM expression correlates with ASCL1+ classic SCLC expression, which is lost during tumor progression. For these experiments, unstained lung sections were prepared and stained as described above. Mouse on Mouse (M.O.M.) Basic Kit (Vector Laboratories) was used for staining with ASCL1. Primary antibodies used: EPCAM (Abcam #71916, 1:100), ASCL1 (BD Pharmingen 556604, 1:100), NEUROD1 (Abcam ab109224, 1:150), MYC (Santa Cruz sc-764, 1:150). Serial sections of in situ (early) and invasive (late) tumors were stained as previously described for MYC, ASCL1 and NEUROD1 and tumors were grouped based on automated quantification of immunohistochemistry staining as ASCL1 or NEUROD1 high or low. Proportions of tumors with each pattern (n=26 total in situ lesions; n=41 invasive lesions) are indicated (see, bar graph).

Figure 19:
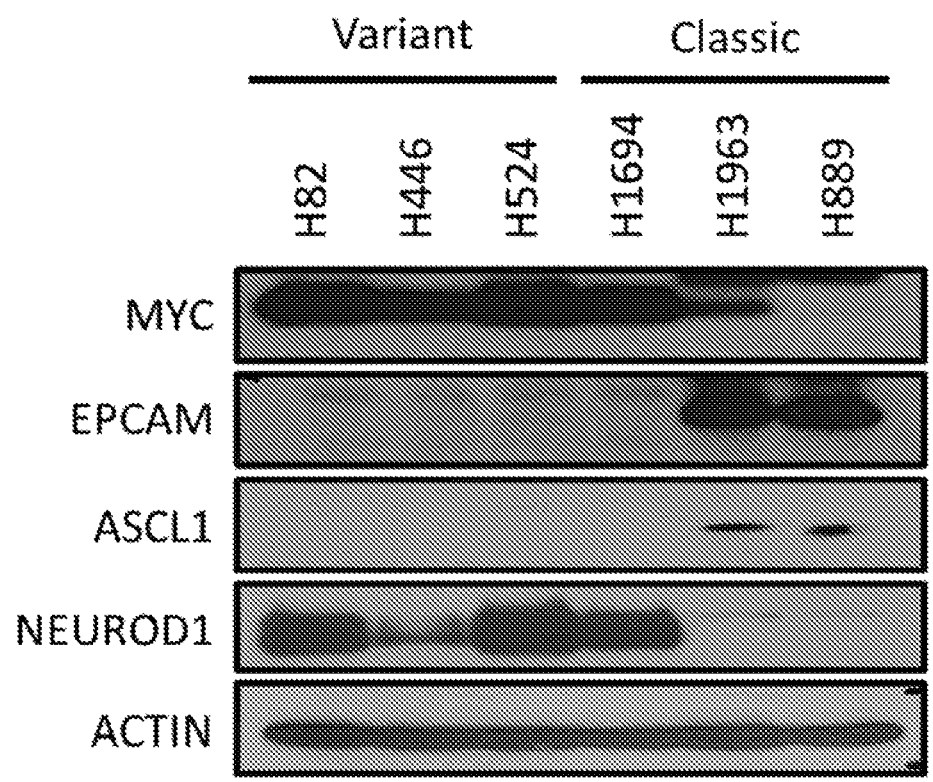
FIG. 19 shows that EPCAM expression correlates with classic cell line phenotype and ASCL1 expression.

Additional experiments were carried out using whole cell lysates from human cell lines prepared using RIPA buffer supplemented with protease inhibitors (Roche complete mini) and sodium orthovanadate (Sigma, St Louis, Mo., USA), separated on Tris-glycine SDS-PAGE gels, and transferred to PVDF membrane (Oliver et al., 2011). Membranes were blocked for 1 hr in 5% milk or 5% BSA in TBS with 0.01% tween 20 (TBS-T), followed by overnight incubation with primary antibodies at 4° C. Membranes were washed for 6×5 min at room temperature in TBS-T. Mouse and rabbit HRP-conjugated secondary antibodies (Jackson ImmunoResearch, 1:10,000) were incubated for 1 hr at room temperature followed by washing 6×5 min at room temperature in TBS-T. For detection, membranes were exposed to WesternBright HRP Quantum substrate (Advansta, Menlo Park, Calif., USA) and detected on Hyblot CL film (Denville Scientific Inc, Holliston, Mass., USA). ACTIN serves as a loading control. The results, shown in FIG. 19, show that EPCAM expression correlates with classic cell line phenotype and ASCL1 expression (n=2).

Figure 20:
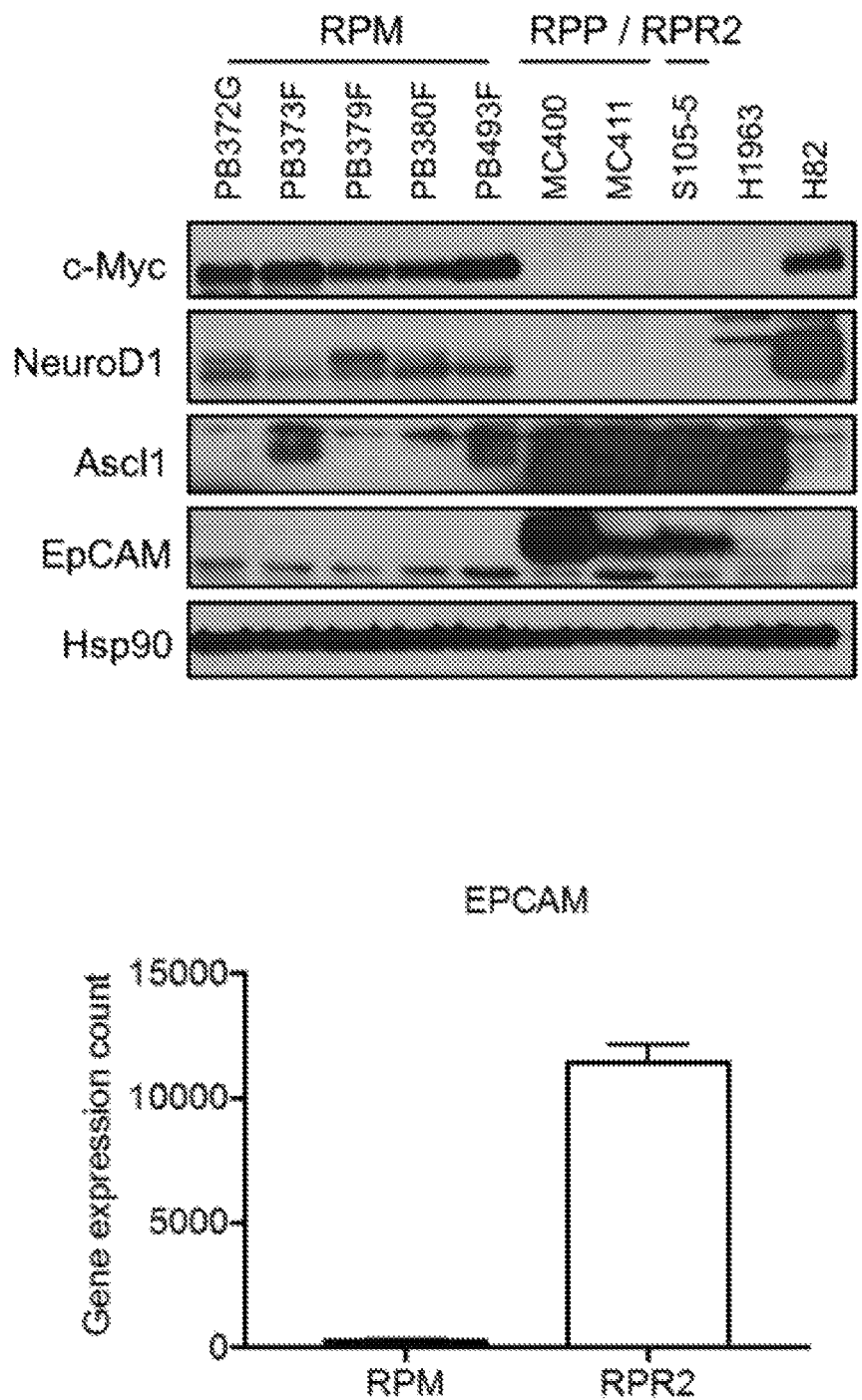
FIG. 20 shows that MYC-driven mouse tumors exhibit low/negative EPCAM expression compared to other models.

EPCAM expression in MYC-driven mouse tumors was evaluated and compared to other models. RPM or RPR2 mouse lungs were harvested when tumor burden necessitated sacrifice. Tumors were dissected from the fresh lung tissue under sterile conditions, snap frozen and stored at −80° C. until use. About 20-40 mg tumor pieces were disrupted and lysed to homogeneity with disposable pestles and cordless motor (VWR, Radnor, Pa., USA) in 200 µl RIPA buffer supplemented with protease inhibitors (Roche complete mini) and sodium orthovanadate (Sigma, St Louis, Mo., USA). Lysates are centrifuged at 13000 rpm for 15 minutes and supernatants are transferred to new tubes. Lysates were separated via SDS-PAGE and transferred to a PVDF membrane (Oliver et al., 2011). Membranes were blocked for 1 hr in 5% milk or 5% BSA, followed by overnight incubation with primary antibodies at 4° C. Membranes were washed for 6×5 min at room temperature in TBS-T. Mouse and rabbit HRP-conjugated secondary antibodies (Jackson ImmunoResearch, 1:10,000) were incubated for 1 hr at room temperature followed by washing 6×5 min at room temperature in TBS-T. For detection (see, FIG. 20; n=2), membranes were exposed to WesternBright HRP Quantum substrate (Advansta, Menlo Park, Calif., USA) and detected on Hyblot CL film (Denville Scientific Inc, Holliston, Mass., USA). HSP90 serves as a loading control.

RPM or mouse tumors were harvested as described above. RNA isolation from primary tumors was performed using RNeasy Mini Kit (Qiagen) with the standard protocol. RNA was subjected to library construction with the Illumina TruSeq Stranded mRNA Sample Preparation Kit (cat # RS-122-2101, RS-122-2102) according to manufacturer's protocol. Chemically denatured sequencing libraries (25 µM) are applied to an Illumina HiSeq v4 single read flow cell using an Illumina cBot. Hybridized molecules were clonally amplified and annealed to sequencing primers with reagents from an Illumina HiSeq SR Cluster Kit v4-cBot (GD-401-4001). Following transfer of the flowcell to an Illumina HiSeq 2500 instrument (HCSv2.2.38 and RTA v1.18.61), a 50 cycle single-read sequence run was performed using HiSeq SBS Kit v4 sequencing reagents (FC-401-4002). Mouse mm10 annotations (Ensembl build 82) were used in the RSEM (v1.2.12) utility rsem-prepare-reference to create bowtie (v1.0.1) indices. Gene expression was determined using the RSEM utility rsem-calculate-expression with the forward strand probability set to zero. Differential expression was determined using EBSeq (v1.4.0) using 'MedianNorm' function to calculate size factors and setting 'maxround' to 10. To adjust for transcript length, fragments per kilobase per million reads (FPKM) were calculated for all genes and log 2-transformed after addition of a small constant (0.01). Gene counts were plotted using Graphpad Prism (GraphPad, La Jolla, Calif., USA; see FIG. 20, n=2). Error bars represent mean+/−SEM.

Together, the results show that MYC-driven mouse tumors exhibit low/negative EPCAM expression compared to other models.

Figure 21:
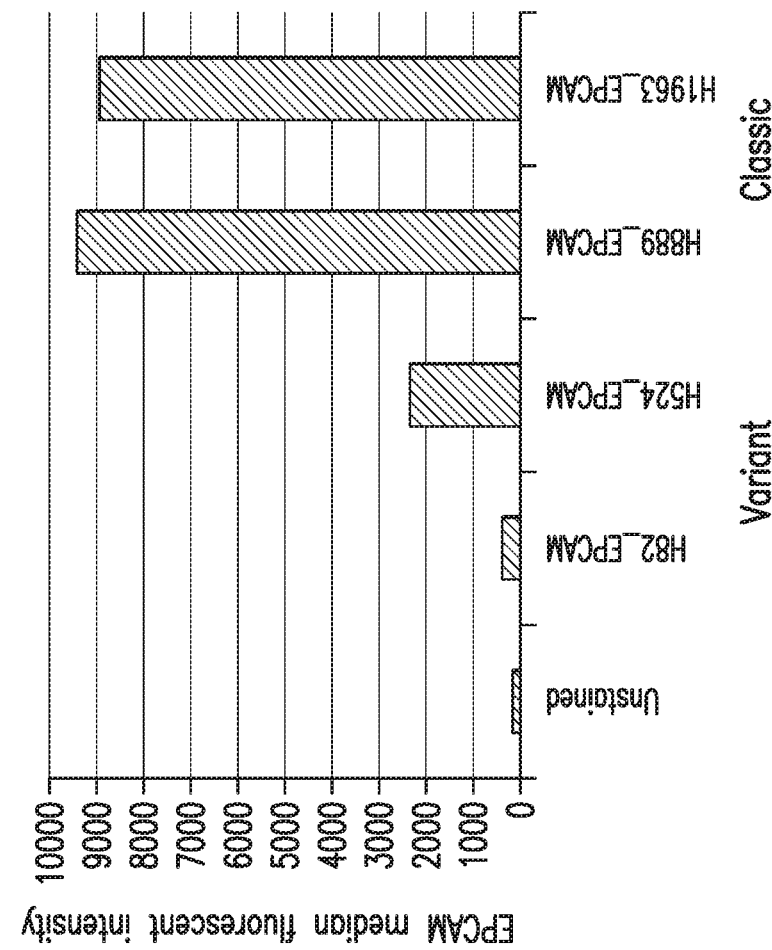
FIG. 21 shows that classic SCLC human cell lines exhibit higher surface expression of EPCAM.
Figure 21:
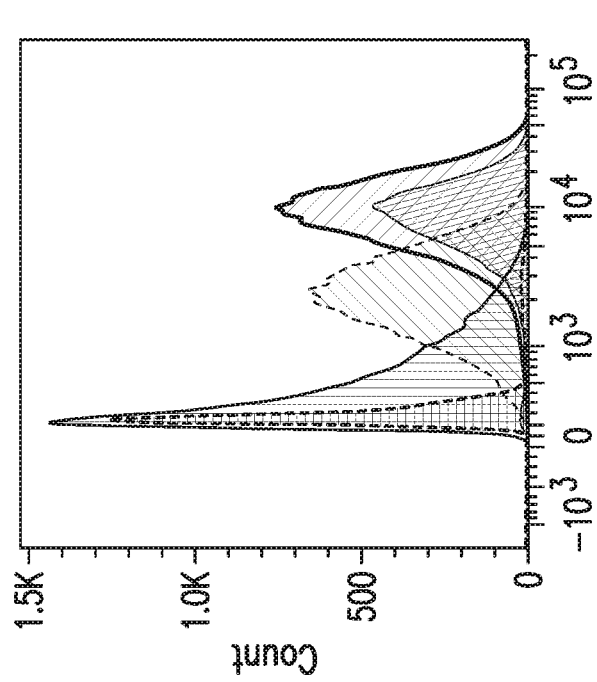

FIG. 21 shows that classic SCLC human cell lines exhibit higher surface expression of EPCAM by flow cytometry. For these experiments, human SCLC cell lines were harvested and $1\times10^4$ cells washed 2× in FACS buffer, stained with APC anti-human CD326 (EPCAM) antibody (Biolegend #324207) at a concentration of 120 ng/ml for 30 min on ice, then washed 2× in FACS buffer. Cells were re-suspended in 300 µl FACS buffer and analyzed on a BD Fortessa flow cytometer. Analysis to calculate median fluorescent intensity was done using FlowJo software. Bar graph of median fluorescent intensity made using Microsoft Excel (Microsoft, Redmond, Wash., USA).

REFERENCES

Borromeo, M. D., Savage, T. K., Kollipara, R. K., He, M., Augustyn, A., Osborne, J. K., Girard, L., Minna, J. D., Gazdar, A. F., Cobb, M. H., et al. (2016). ASCL1 and NEUROD1 Reveal Heterogeneity in Pulmonary Neuroendocrine Tumors and Regulate Distinct Genetic Programs. Cell Reports 16, 1259-1272.

Brennan, J., O'Connor, T., Makuch, R. W., Simmons, A. M., Russell, E., Linnoila, R. I., Phelps, R. M., Gazdar, A. F., Ihde, D. C., and Johnson, B. E. (1991). myc family DNA amplification in 107 tumors and tumor cell lines from patients with small cell lung cancer treated with different combination chemotherapy regimens. Cancer Res 51, 1708-1712.

Brockmann, M., Poon, E., Berry, T., Carstensen, A., Deubzer, H. E., Rycak, L., Jamin, Y., Thway, K., Robinson, S. P., Roels, F., et al. (2013). Small molecule inhibitors of aurora-a induce proteasomal degradation of N-myc in childhood neuroblastoma. Cancer Cell 24, 75-89.

Bunn, P. A., Jr., Minna, J., Augustyn, A., Gazdar, A., Ouadah, Y., Krasnow, M. A., Berns, A., Brambilla, E., Rekhtman, N., Massion, P. P., et al. (2016). Small Cell Lung Cancer: Can recent advances in biology and molecular biology be translated into improved outcomes? Journal of thoracic oncology: official publication of the International Association for the Study of Lung Cancer.

Calbo, J., van Montfort, E., Proost, N., van Drunen, E., Beverloo, H. B., Meuwissen, R., and Berns, A. (2011). A functional role for tumor cell heterogeneity in a mouse model of small cell lung cancer. Cancer Cell 19, 244-256.

Carney, D. N., Gazdar, A. F., Bepler, G., Guccion, J. G., Marangos, P. J., Moody, T. W., Zweig, M. H., and Minna, J. D. (1985). Establishment and identification of small cell lung cancer cell lines having classic and variant features. Cancer Res 45, 2913-2923.

Christensen, C. L., Kwiatkowski, N., Abraham, B. J., Carretero, J., Al-Shahrour, F., Zhang, T., Chipumuro, E., Herter-Sprie, G. S., Akbay, E. A., Altabef, A., et al. (2014). Targeting transcriptional addictions in small cell lung cancer with a covalent CDK7 inhibitor. Cancer Cell 26, 909-922.

Cui, M., Augert, A., Rongione, M., Conkrite, K., Parazzoli, S., Nikitin, A. Y., Ingolia, N., and MacPherson, D. (2014). PTEN is a potent suppressor of small cell lung cancer. Molecular cancer research: MCR 12, 654-659.

Denny, S. K., Yang, D., Chuang, C. H., Brady, J. J., Lim, J. S., Gruner, B. M., Chiou, S. H., Schep, A. N., Baral, J., Hamard, C., et al. (2016). Nfib Promotes Metastasis through a Widespread Increase in Chromatin Accessibility. Cell 166, 328-342.

Dooley, A. L., Winslow, M. M., Chiang, D. Y., Banerji, S., Stransky, N., Dayton, T. L., Snyder, E. L., Senna, S., Whittaker, C. A., Bronson, R. T., et al. (2011). Nuclear factor I/B is an oncogene in small cell lung cancer. Genes Dev 25, 1470-1475.

Elliott, J. A., Osterlind, K., Hirsch, F. R., and Hansen, H. H. (1987). Metastatic patterns in small-cell lung cancer: correlation of autopsy findings with clinical parameters in 537 patients. J Clin Oncol 5, 246-254.

Gazdar, A. F., Carney, D. N., Nau, M. M., and Minna, J. D. (1985). Characterization of variant subclasses of cell lines derived from small cell lung cancer having distinctive biochemical, morphological, and growth properties. Cancer Res 45, 2924-2930.

Gazdar, A. F., Savage, T. K., Johnson, J. E., Berns, A., Sage, J., Linnoila, R. I., MacPherson, D., McFadden, D. G., Farago, A., Jacks, T., et al. (2015). The comparative pathology of genetically engineered mouse models for neuroendocrine carcinomas of the lung. Journal of thoracic oncology: official publication of the International Association for the Study of Lung Cancer 10, 553-564.

Gazzeri, S., Brambilla, E., Jacrot, M., Chauvin, C., Benabid, A. L., and Brambilla, C. (1991). Activation of myc gene family in human lung carcinomas and during heterotransplantation into nude mice. Cancer Res 51, 2566-2571.

George, J., Lim, J. S., Jang, S. J., Cun, Y., Ozretic, L., Kong, G., Leenders, F., Lu, X., Fernandez-Cuesta, L., Bosco, G., et al. (2015). Comprehensive genomic profiles of small cell lung cancer. Nature 524, 47-53.

Gustafson, W. C., Meyerowitz, J. G., Nekritz, E. A., Chen, J., Benes, C., Charron, E., Simonds, E. F., Seeger, R., Matthay, K. K., Hertz, N. T., et al. (2014). Drugging MYCN through an allosteric transition in Aurora kinase A. Cancer Cell 26, 414-427.

Hodgkinson, C. L., Morrow, C. J., Li, Y., Metcalf, R. L., Rothwell, D. G., Trapani, F., Polanski, R., Burt, D. J., Simpson, K. L., Morris, K., et al. (2014). Tumorigenicity and genetic profiling of circulating tumor cells in small-cell lung cancer. Nat Med 20, 897-903.

Hook, K. E., Garza, S. J., Lira, M. E., Ching, K. A., Lee, N. V., Cao, J., Yuan, J., Ye, J., Ozeck, M., Shi, S. T., et al. (2012). An integrated genomic approach to identify predictive biomarkers of response to the aurora kinase inhibitor PF-03814735. Mol Cancer Ther 11, 710-719.

Huijbers, I. J., Bin Ali, R., Pritchard, C., Cozijnsen, M., Kwon, M. C., Proost, N., Song, J. Y., de Vries, H., Badhai, J., Sutherland, K., et al. (2014). Rapid target gene validation in complex cancer mouse models using re-derived embryonic stem cells. EMBO molecular medicine 6, 212-225.

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes Dev 15, 3243-3248.

Johnson, B. E., Brennan, J. F., Ihde, D. C., and Gazdar, A. F. (1992). myc family DNA amplification in tumors and tumor cell lines from patients with small-cell lung cancer. J Natl Cancer Inst Monogr, 39-43.

Johnson, B. E., Ihde, D. C., Makuch, R. W., Gazdar, A. F., Carney, D. N., Oie, H., Russell, E., Nau, M. M., and Minna, J. D. (1987). myc family oncogene amplification in tumor cell lines established from small cell lung cancer patients and its relationship to clinical status and course. The Journal of clinical investigation 79, 1629-1634.

Johnson, B. E., Russell, E., Simmons, A. M., Phelps, R., Steinberg, S. M., Ihde, D. C., and Gazdar, A. F. (1996). MYC family DNA amplification in 126 tumor cell lines from patients with small-cell lung cancer. J Cell Biochem Suppl 24, 210-217.

Kalemkerian, G. P., Akerley, W., Bogner, P., Borghaei, H., Chow, L. Q., Downey, R. J., Gandhi, L., Ganti, A. K., Govindan, R., Grecula, J. C., et al. (2013). Small cell lung cancer. J Natl Compr Canc Netw 11, 78-98.

McFadden, D. G., Papagiannakopoulos, T., Taylor-Weiner, A., Stewart, C., Carter, S. L., Cibulskis, K., Bhutkar, A., McKenna, A., Dooley, A., Vernon, A., et al. (2014). Genetic and clonal dissection of murine small cell lung carcinoma progression by genome sequencing. Cell 156, 1298-1311.

Melichar, B., Adenis, A., Lockhart, A. C., Bennouna, J., Dees, E. C., Kayaleh, O., Obermannova, R., DeMichele, A., Zatloukal, P., Zhang, B., et al. (2015). Safety and activity of alisertib, an investigational aurora kinase A inhibitor, in patients with breast cancer, small-cell lung cancer, non-small-cell lung cancer, head and neck squamous-cell carcinoma, and gastro-oesophageal adenocarcinoma: a five-arm phase 2 study. Lancet Oncol 16, 395-405.

Meuwissen, R., Linn, S. C., Linnoila, R. I., Zevenhoven, J., Mooi, W. J., and Berns, A. (2003). Induction of small cell lung cancer by somatic inactivation of both Trp53 and Rb1 in a conditional mouse model. Cancer Cell 4, 181-189.

Mukhopadhyay, A., Berrett, K. C., Kc, U., Clair, P. M., Pop, S. M., Carr, S. R., Witt, B. L., and Oliver, T. G. (2014). Sox2 cooperates with Lkb1 loss in a mouse model of squamous cell lung cancer. Cell Reports 8, 40-49.

Oliver, T. G., Mercer, K. L., Sayles, L. C., Burke, J. R., Mendus, D., Lovejoy, K. S., Cheng, M. H., Subramanian, A., Mu, D., Powers, S., et al. (2010). Chronic cisplatin treatment promotes enhanced damage repair and tumor progression in a mouse model of lung cancer. Genes Dev 24, 837-852.

Osborne, J. K., Larsen, J. E., Shields, M. D., Gonzales, J. X., Shames, D. S., Sato, M., Kulkarni, A., Wistuba, II, Girard, L., Minna, J. D., et al. (2013). NeuroD1 regulates survival and migration of neuroendocrine lung carcinomas via signaling molecules TrkB and NCAM. Proc Natl Acad Sci USA 110, 6524-6529.

Otto, T., Horn, S., Brockmann, M., Eilers, U., Schuttrumpf, L., Popov, N., Kenney, A. M., Schulte, J. H., Beijersbergen, R., Christiansen, H., et al. (2009). Stabilization of N-Myc is a critical function of Aurora A in human neuroblastoma. Cancer Cell 15, 67-78.

Peifer, M., Fernandez-Cuesta, L., Sos, M. L., George, J., Seidel, D., Kasper, L. H., Plenker, D., Leenders, F., Sun, R., Zander, T., et al. (2012). Integrative genome analyses identify key somatic driver mutations of small-cell lung cancer. Nat Genet 44, 1104-1110.

Pietanza, M. C., Byers, L. A., Minna, J. D., and Rudin, C. M. (2015). Small cell lung cancer: will recent progress lead to improved outcomes? Clin Cancer Res 21, 2244-2255.

Poirier, J. T., Dobromilskaya, I., Moriarty, W. F., Peacock, C. D., Hann, C. L., and Rudin, C. M. (2013). Selective tropism of Seneca Valley virus for variant subtype small cell lung cancer. Journal of the National Cancer Institute 105, 1059-1065.

Poirier, J. T., Gardner, E. E., Connis, N., Moreira, A. L., de Stanchina, E., Hann, C. L., and Rudin, C. M. (2015). DNA methylation in small cell lung cancer defines distinct disease subtypes and correlates with high expression of EZH2. Oncogene 34, 5869-5878.

Polley, E., Kunkel, M., Evans, D., Silvers, T., Delosh, R., Laudeman, J., Ogle, C., Reinhart, R., Selby, M., Connelly, J., et al. (2016). Small Cell Lung Cancer Screen of Oncology Drugs, Investigational Agents, and Gene and microRNA Expression. Journal of the National Cancer Institute 108.

Rekhtman, N. (2010). Neuroendocrine tumors of the lung: an update. Arch Pathol Lab Med 134, 1628-1638.

Rudin, C. M., Durinck, S., Stawiski, E. W., Poirier, J. T., Modrusan, Z., Shames, D. S., Bergbower, E. A., Guan, Y., Shin, J., Guillory, J., et al. (2012). Comprehensive genomic analysis identifies SOX2 as a frequently amplified gene in small-cell lung cancer. Nat Genet 44, 1111-1116.

Sage, J., Mulligan, G. J., Attardi, L. D., Miller, A., Chen, S., Williams, B., Theodorou, E., and Jacks, T. (2000). Targeted disruption of the three Rb-related genes leads to loss of G(1) control and immortalization. Genes Dev 14, 3037-3050.

Saunders, L. R., Bankovich, A. J., Anderson, W. C., Aujay, M. A., Bheddah, S., Black, K., Desai, R., Escarpe, P. A., Hampl, J., Laysang, A., et al. (2015). A DLL3-targeted antibody-drug conjugate eradicates high-grade pulmonary neuroendocrine tumor-initiating cells in vivo. Sci Transl Med 7, 302ra136.

Schaffer, B. E., Park, K. S., Yiu, G., Conklin, J. F., Lin, C., Burkhart, D. L., Karnezis, A. N., Sweet-Cordero, E. A., and Sage, J. (2010). Loss of p130 accelerates tumor development in a mouse model for human small-cell lung carcinoma. Cancer Res 70, 3877-3883.

Schoffski, P., Besse, B., Gauler, T., de Jonge, M. J., Scambia, G., Santoro, A., Davite, C., Jannuzzo, M. G., Petroccione, A., and Delord, J. P. (2015). Efficacy and safety of biweekly i.v. administrations of the Aurora kinase inhibitor danusertib hydrochloride in independent cohorts of patients with advanced or metastatic breast, ovarian, colorectal, pancreatic, small-cell and non-small-cell lung cancer: a multi-tumour, multi-institutional phase II study. Ann Oncol 26, 598-607.

Semenova, E. A., Kwon, M. C., Monkhorst, K., Song, J. Y., Bhaskaran, R., Krijgsman, O., Kuilman, T., Peters, D., Buikhuisen, W. A., Smit, E. F., et al. (2016). Transcription Factor NFIB Is a Driver of Small Cell Lung Cancer Progression in Mice and Marks Metastatic Disease in Patients. Cell Reports 16, 631-643.

Semenova, E. A., Nagel, R., and Berns, A. (2015). Origins, genetic landscape, and emerging therapies of small cell lung cancer. Genes Dev 29, 1447-1462.

Sos, M. L., Dietlein, F., Peifer, M., Schottle, J., Balke-Want, H., Muller, C., Koker, M., Richters, A., Heynck, S., Malchers, F., et al. (2012). A framework for identification of actionable cancer genome dependencies in small cell lung cancer. Proc Natl Acad Sci USA 109, 17034-17039.

Sutherland, K. D., Proost, N., Brouns, I., Adriaensen, D., Song, J. Y., and Berns, A. (2011). Cell of origin of small cell lung cancer: inactivation of Trp53 and Rb1 in distinct cell types of adult mouse lung. Cancer Cell 19, 754-764.

Toyoshima, M., Howie, H. L., Imakura, M., Walsh, R. M., Annis, J. E., Chang, A. N., Frazier, J., Chau, B. N., Loboda, A., Linsley, P. S., et al. (2012). Functional genomics identifies therapeutic targets for MYC-driven cancer. Proc Natl Acad Sci USA 109, 9545-9550.

Travis, W. D. (2009). Lung tumours with neuroendocrine differentiation. Eur J Cancer 45 Suppl 1, 251-266.

Travis, W. D. (2012). Update on small cell carcinoma and its differentiation from squamous cell carcinoma and other non-small cell carcinomas. Modern pathology: an official journal of the United States and Canadian Academy of Pathology, Inc 25 Suppl 1, S18-30.

Travis, W. D., Brambilla, E., Nicholson, A. G., Yatabe, Y., Austin, J. H., Beasley, M. B., Chirieac, L. R., Dacic, S., Duhig, E., Flieder, D. B., et al. (2015). The 2015 World Health Organization Classification of Lung Tumors: Impact of Genetic, Clinical and Radiologic Advances Since the 2004 Classification. Journal of thoracic oncology: official publication of the International Association for the Study of Lung Cancer 10, 1243-1260.

Wilkinson, R. W., Odedra, R., Heaton, S. P., Wedge, S. R., Keen, N. J., Crafter, C., Foster, J. R., Brady, M. C., Bigley, A., Brown, E., et al. (2007). AZD1152, a selective inhibitor of Aurora B kinase, inhibits human tumor xenograft growth by inducing apoptosis. Clin Cancer Res 13, 3682-3688.

Yang, D., Liu, H., Goga, A., Kim, S., Yuneva, M., and Bishop, J. M. (2010). Therapeutic potential of a synthetic lethal interaction between the MYC proto-oncogene and inhibition of aurora-B kinase. Proc Natl Acad Sci USA 107, 13836-13841.

Benaglia, T., Chauveau, D., Hunter, D., and Young, D. (2009). mixtools: An R package for analyzing finite mixture models. Journal of Statistical Software 32, 1-29.

Borromeo, M. D., Savage, T. K., Kollipara, R. K., He, M., Augustyn, A., Osborne, J. K., Girard, L., Minna, J. D., Gazdar, A. F., Cobb, M. H., et al. (2016). ASCL1 and NEUROD1 Reveal Heterogeneity in Pulmonary Neuroendocrine Tumors and Regulate Distinct Genetic Programs. Cell Reports 16, 1259-1272.

Brockmann, M., Poon, E., Berry, T., Carstensen, A., Deubzer, H. E., Rycak, L., Jamin, Y., Thway, K., Robinson, S. P., Roels, F., et al. (2013). Small molecule inhibitors of aurora-a induce proteasomal degradation of N-myc in childhood neuroblastoma. Cancer Cell 24, 75-89.

Fernandez-Cuesta, L., Sun, R., Menon, R., George, J., Lorenz, S., Meza-Zepeda, L. A., Peifer, M., Plenker, D., Heuckmann, J. M., Leenders, F., et al. (2015). Identification of novel fusion genes in lung cancer using breakpoint assembly of transcriptome sequencing data. Genome Biol 16, 7.

George, J., Lim, J. S., Jang, S. J., Cun, Y., Ozretic, L., Kong, G., Leenders, F., Lu, X., Fernandez-Cuesta, L., Bosco, G., et al. (2015). Comprehensive genomic profiles of small cell lung cancer. Nature 524, 47-53.

Kim, D. W., Wu, N., Kim, Y. C., Cheng, P. F., Basom, R., Kim, D., Dunn, C. T., Lee, A. Y., Kim, K., Lee, C. S., et al. (2016). Genetic requirement for Mycl and efficacy of RNA Pol I inhibition in mouse models of small cell lung cancer. Genes Dev 30, 1289-1299.

Langmead, B., Trapnell, C., Pop, M., and Salzberg, S. L. (2009). Ultrafast and memory-efficient alignment of short DNA sequences to the human genome. Genome Biol 10, R25.

Peifer, M., Fernandez-Cuesta, L., Sos, M. L., George, J., Seidel, D., Kasper, L. H., Plenker, D., Leenders, F., Sun, R., Zander, T., et al. (2012). Integrative genome analyses identify key somatic driver mutations of small-cell lung cancer. Nat Genet 44, 1104-1110.

Polley, E., Kunkel, M., Evans, D., Silvers, T., Delosh, R., Laudeman, J., Ogle, C., Reinhart, R., Selby, M., Connelly, J., et al. (2016). Small Cell Lung Cancer Screen of Oncology Drugs, Investigational Agents, and Gene and microRNA Expression. Journal of the National Cancer Institute 108.

Reddy, T. E., Pauli, F., Sprouse, R. O., Neff, N. F., Newberry, K. M., Garabedian, M. J., and Myers, R. M. (2009). Genomic determination of the glucocorticoid response reveals unexpected mechanisms of gene regulation. Genome Res 19, 2163-2171.

Rudin, C. M., Durinck, S., Stawiski, E. W., Poirier, J. T., Modrusan, Z., Shames, D. S., Bergbower, E. A., Guan, Y., Shin, J., Guillory, J., et al. (2012). Comprehensive genomic analysis identifies SOX2 as a frequently amplified gene in small-cell lung cancer. Nat Genet 44, 1111-1116.

Schaffer, B. E., Park, K. S., Yiu, G., Conklin, J. F., Lin, C., Burkhart, D. L., Karnezis, A. N., Sweet-Cordero, E. A., and Sage, J. (2010). Loss of p130 accelerates tumor development in a mouse model for human small-cell lung carcinoma. Cancer Res 70, 3877-3883.

Sos, M. L., Dietlein, F., Peifer, M., Schottle, J., Balke-Want, H., Muller, C., Koker, M., Richters, A., Heynck, S., Malchers, F., et al. (2012). A framework for identification of actionable cancer genome dependencies in small cell lung cancer. Proc Natl Acad Sci USA 109, 17034-17039.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.

Talevich, E., Shain, A. H., Botton, T., and Bastian, B. C. (2016). CNVkit: Genome-Wide Copy Number Detection and Visualization from Targeted DNA Sequencing. PLoS computational biology 12, e1004873.

Team, R. C. (2014). R: A language and environment for statistical computing. R Foundation for Statistical Computing, Vienna, Austria http://www.R-project.org/.

Trapnell, C., Williams, B. A., Pertea, G., Mortazavi, A., Kwan, G., van Baren, M. J., Salzberg, S. L., Wold, B. J., and Pachter, L. (2010). Transcript assembly and quantification by RNA-Seq reveals unannotated transcripts and isoform switching during cell differentiation. Nat Biotechnol 28, 511-515.

Ward, J. H. (1963). Hierarchical Grouping to Optimize an Objective Function. Journal of the American Statistical Association 58, 236-244.

Wu, T. D., and Nacu, S. (2010). Fast and SNP-tolerant detection of complex variants and splicing in short reads. Bioinformatics 26, 873-881.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome Biol 9, R137.

What is claimed is:

1. A method of detecting a variant subtype of small cell lung cancer in a subject and treating the subject, the method comprising:
 a. obtaining or having obtained a sample from a human subject;
 b. determining the level of (i) NEUROD1, (ii) Myc or Mycl, and (iii) ASCL1 in the subject's sample;
 c. detecting an increased level of NEUROD1, an increased level of Myc or a decreased level of Mycl and a decreased level of ASCL1 in the subject's sample as compared to a sample from a human subject that does not have small cell lung cancer, thereby detecting a variant subtype of small cell lung cancer in the subject; and
 d. administering to the subject determined to have the variant subtype of small cell lung cancer an aurora kinase inhibitor.

2. The method of claim 1, wherein the level of (i) NEUROD1, (ii) Myc or Mycl, and (iii) ASCL1 is determined using RNA-sequence data analysis or polymerase chain reaction.

3. The method of claim 2, wherein the sample is a blood or lung tissue sample.

4. A method of predicting a small cell lung cancer patient's responsiveness to an aurora kinase inhibitor and treating the patient, the method comprising:
 a. obtaining or having obtained a sample from the patient;
 b. determining the level of (i) NEUROD1, (ii) Myc or Mycl, and (iii) ASCL1 in the patient's sample,
 c. detecting an increased level of NEUROD1, an increased level of Myc or a decreased level of Mycl and a decreased level of ASCL1 in the patient's sample as compared to a sample from a human subject that does not have small cell lung cancer, thereby indicating that the patient is likely to respond to an aurora kinase inhibitor, and
 d. following step c., administering to the patient an aurora kinase inhibitor.

5. A method of predicting a small cell lung cancer patient's responsiveness to a BCL-2 inhibitor and treating the patient, the method comprising:
 a. obtaining or having obtained a sample from the patient;
 b. determining the level of (i) NEUROD1, (ii) Myc or Mycl, and (iii) ASCL1 in the patient's sample,
 c. detecting a decreased level of NEUROD1, an increased level of Mycl or a decreased level of Myc, and an increased level of ASCL1 in the patient's sample as compared to a sample from a human subject that does not have small cell lung cancer, thereby indicating that the patient is likely to respond to a BCL-2 inhibitor; and
 d. following step c., administering to the patient a BCL-2 inhibitor.

6. The method of claim 1, wherein the aurora kinase inhibitor is alisertib.

7. The method of claim 4, wherein the aurora kinase inhibitor is alisertib.

* * * * *